United States Patent
Rodgers et al.

(10) Patent No.: US 6,969,721 B2
(45) Date of Patent: Nov. 29, 2005

(54) TRICYCLIC-2-PYRIDONE COMPOUNDS USEFUL AS HIV REVERSE TRANSCRIPTASE INHIBITORS

(75) Inventors: James D. Rodgers, Landenberg, PA (US); Haisheng Wang, Wilmington, DE (US); Mona Patel, Belle Mead, NJ (US); Argyrios Arvanitis, Kennett Square, PA (US); Anthony J. Cocuzza, Wilmington, DE (US)

(73) Assignee: Bristol-Myers Squibb Pharma, Princeton, NJ (US)

( * ) Notice: Subject to any disclaimer, the term of this patent is extended or adjusted under 35 U.S.C. 154(b) by 110 days.

(21) Appl. No.: 10/457,902

(22) Filed: Jun. 10, 2003

(65) Prior Publication Data

US 2004/0023955 A1 Feb. 5, 2004

Related U.S. Application Data

(62) Division of application No. 09/908,995, filed on Jul. 19, 2001, now Pat. No. 6,596,729.
(60) Provisional application No. 60/264,856, filed on Apr. 19, 2001, and provisional application No. 60/219,532, filed on Jul. 20, 2000.

(51) Int. Cl.[7] ............... A61K 31/4375; C07D 471/04
(52) U.S. Cl. ............... 514/291; 546/81; 514/291; 514/292
(58) Field of Search ............ 546/81; 514/291, 514/292

(56) References Cited

U.S. PATENT DOCUMENTS 6,030,967 A  2/2000  Marui et al.

FOREIGN PATENT DOCUMENTS

| DE | 2206674 | * 8/1972 | ........... C07D/39/10 |
|---|---|---|---|
| DE | 4320347 | 12/1994 | |
| DE | 4344452 | 6/1995 | |
| EP | 0530994 | 3/1993 | |
| WO | WO 92/06971 | 4/1992 | |
| WO | 9207468 | 5/1992 | |
| WO | 9512583 | 5/1995 | |
| WO | 9814436 | 4/1998 | |
| WO | WO 98/20867 | 5/1998 | |
| WO | 9845276 | 10/1998 | |
| WO | WO 00/29577 | 5/2000 | |
| WO | 0129037 | 4/2001 | |

OTHER PUBLICATIONS

CAPLUS AN 2003:204695, abstract of Grivel et al, "Bystander CD4+ T lymphocytes survive in HIV–infected human lymphoid tissue." AIDS Research and Human Retroviruses (2003), vol. 19(3), pp. 211–216.*

Package insert for "Sustiva™ (efavirenz capsules) Rx Only", Sep. 22, 1998, http://www.fda.gov/cder/foi/label/1998/20972lbl.pdf.

U.S. Department of Health and Human Services, For Immediate Release, Sep. 28, 1998, FDA Approves New Drug to Treat HIV, AIDS, http://www.fda.gov/bbs/topics/NEWS/NEW00654.html.

Meisel et al, "Synthese von 10–Substituierten 5,5–dimethyl–5,10–dihydro–benzo(B)(1,8)Naphthyridinen" vol. 39, No. 10, 1984, pp. 671–672, XP000986134.

* cited by examiner

*Primary Examiner*—Joseph K. McKane
*Assistant Examiner*—Janet L. Coppins
(74) *Attorney, Agent, or Firm*—Mary VanAtten

(57) ABSTRACT

The present invention relates to tricyclic 2-pyridone compounds of formula (I):

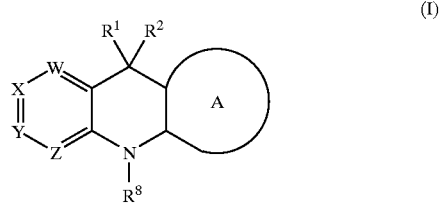

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

12 Claims, No Drawings

SEQUENCE LISTING

<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: synthetic

<400> SEQUENCE: 1
ctagctccct gcttgcccat acta                                              24

<210> SEQ ID NO 2
<211> LENGTH: 22

-continued

```
<212> TYPE: DNA
<213> ORGANISM: Artificial
<220> FEATURE:
<223> OTHER INFORMATION: synthetic

<400> SEQUENCE: 2
ccctatcatt tttggtttcc at                                               22

<210> SEQ ID NO 3
<211> LENGTH: 23
<212> TYPE: DNA
<213> ORGANISM: Artificial
<220> FEATURE:
<223> OTHER INFORMATION: synthetic

<400> SEQUENCE: 3
ctgtcttact ttgataaaac ctc                                              23

<210> SEQ ID NO 4
<211> LENGTH: 24
<212> TYPE: DNA
<213> ORGANISM: Artificial
<220> FEATURE:
<223> OTHER INFORMATION: synthetic

<400> SEQUENCE: 4
cccagtattt gtctacagcc ttct                                             24
```

TRICYCLIC-2-PYRIDONE COMPOUNDS USEFUL AS HIV REVERSE TRANSCRIPTASE INHIBITORS

CROSS-REFERENCE TO RELATED APPLICATIONS

This application is a Divisional of Ser. No. 09/908,995 filed Jul. 19, 2001 now U.S. Pat. No. 6,596,729, and claims the priority benefits of U.S. Provisional Application No. 60/284,856 filed Apr. 19, 2001 and U.S. Provisional Application No. 60/219,532 filed Jul. 20, 2000, which are expressly incorporated fully herein by reference.

FIELD OF THE INVENTION

This invention relates generally to tricyclic pyridone compounds which are useful as inhibitors of HIV reverse transcriptase, pharmaceutical compositions and diagnostic kits comprising the same, methods of using the same for treating viral infection or as assay standards or reagents, and intermediates and processes for making such tricyclic compounds.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the consequence of HIV-1 or HIV-2 virus following its complex viral life cycle. The virion life cycle involves the virion attaching itself to the host human T-4 lymphocyte immune cell through the binding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

RNA polymerase transcribes the integrated viral DNA into viral mRNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. In most cases, without therapeutic intervention, HIV causes the host's immune system to be debilitated, allowing opportunistic infections to set in. Without the administration of antiviral agents, immunomodulators, or both, death may result.

There are at least three critical points in the HIV life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treating AIDS. This transcription must occur for the virion to reproduce because the virion's genes are encoded in RNA and the host cell transcribes only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in certain cases in halting HIV replication at the reverse transcriptase (RT) stage.

An active area of research is in the discovery of non-nucleoside HIV reverse transcriptase inhibitors (NNRTIs). As an example, it has been found that certain benzoxazinones and quinazolinones are active in the inhibition of HIV reverse transcriptase, the prevention or treatment of infection by HIV and the treatment of AIDS.

U.S. Pat. No. 5,874,430 describes benzoxazinone non-nucleoside reverse transcriptase inhibitors for the treatment of HIV. U.S. Pat. No. 5,519,021 describe non-nucleoside reverse transcriptase inhibitors which are benzoxazinones of the formula:

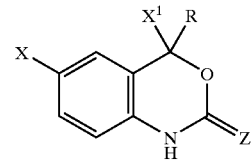

wherein X is a halogen, Z may be O.

EP 0,530,994 and WO 93/04047 describe HIV reverse transcriptase inhibitors which are quinazolinones of the formula (A):

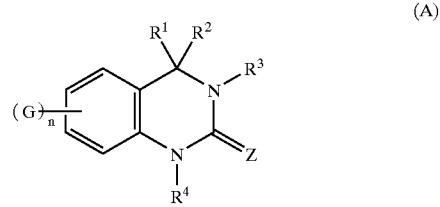

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4-((2-pyridy) ethynyl)-2(1H)-quinazolinone.

Synthetic procedures for making quinazolinones like those described above are detailed in the following references: Houpis et al., *Tetr. Lett.* 1994, 35(37), 6811–6814; Tucker et al., *J. Med. Chem.* 1994, 37, 2437–2444; and, Huffman et al., *J. Org. Chem.* 1995, 60, 1590–1594.

DE 4,320,347 illustrates quinazolinones of the formula:

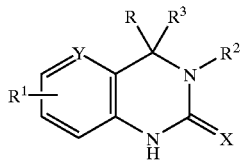

wherein R is a phenyl, carbocyclic ring, or a heterocyclic ring. Compounds of this sort are not considered to be part of the present invention.

Even with the current success of reverse transcriptase inhibitors, it has been found that HIV patients can become resistant to a given inhibitor. Thus, there is an important need to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention, including a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected from the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide novel tricyclic 2-pyridone compounds for use in therapy.

It is another object of the present invention to provide the use of novel tricyclic 2-pyridone compounds for the manufacture of a medicament for the treatment of HIV infection.

These and other objects, which will become apparent during the following detailed description, have been achieved by the inventors' discovery that compounds of formula (I):

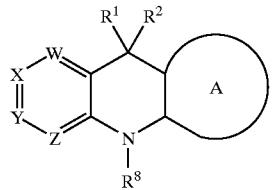

wherein $R^1$, $R^2$, $R^8$, A, W, X, Y, and Z are defined below, including any stereoisomeric form, mixtures of stereoisomeric forms, complexes, prodrug forms or pharmaceutically acceptable salt forms thereof, are effective reverse transcriptase inhibitors.

DETAILED DESCRIPTION OF PREFERRED EMBODIMENTS

[1] Thus, in an embodiment, the present invention provides a novel compound of formula (I):

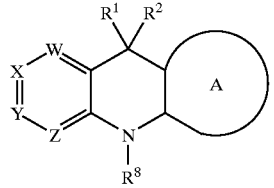

or a stereoisomeric form or mixture of stereoisomeric forms or a pharmaceutically acceptable salt form thereof, wherein:
A is a ring selected from:

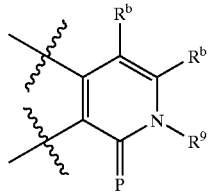 and 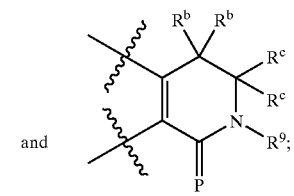

P is O or S;
$R^b$, at each occurrence, is independently selected from H, F, Cl, Br, I, CN, $C_{1-4}$ alkyl, $C_{1-4}$ alkenyl, $C_{1-4}$ alkynyl, $C_{1-4}$ alkyl-O—, or $C_{1-4}$ alkyl-NH—, $NH_2$;
$R^c$, at each occurrence, is independently selected from H, $C_{1-4}$ alkyl, $C_{1-4}$ alkenyl, and $C_{1-4}$ alkynyl;
W is N or $CR^3$;
X is N or $CR^{3a}$;
Y is N or $CR^{3b}$;
Z is N or $CR^{3c}$;
provided that if two of W, X, Y, and Z are N, then the remaining are other than N;
$R^1$ is selected from the group $C_{1-4}$ alkyl substituted with 0–9 halogen, cyclopropyl, hydroxymethyl, and CN;
$R^2$ is selected from the group methyl substituted with 0–3 $R^{3f}$, $C_{1-6}$ alkyl substituted with 0–2 $R^4$, $C_{2-6}$haloalkyl, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;
$R^3$ is selected from the group H, $C_{1-4}$ alkyl, —OH, $C_{1-4}$ alkoxy, $OCF_3$, $CF_3$, F, Cl, Br, I, —$(CH_2)_rNR^5R^{5a}$, —$NO_2$, —CN, —$C(O)R^6$, —$(CH_2)_rNHC(O)R^7$, —$(CH_2)_rNHC (O)NR$^5$R$^{5a}$, —NHSO$_2$R$^{10}$, —S—C$_{1-4}$alkyl, —S(O)C$_{1-4}$ alkyl, —S(O)$_2$C$_{1-4}$alkyl, —SO$_2$NR$^5$R$^{5a}$, and a 5–6 membered heteroaromatic ring containing 1–4 heteroatoms selected from the group O, N, and S;

R$^{3a}$ is selected from the group H, C$_{1-4}$ alkyl, —OH, C$_{1-4}$ alkoxy, OCF$_3$, CF$_3$, F, Cl, Br, I, —(CH$_2$)$_r$NR$^5$R$^{5a}$, —NO$_2$, —CN, —C(O)R$^6$, —(CH$_2$)$_r$NHC(O)R$^7$, —(CH$_2$)$_r$NHC(O)NR$^5$R$^{5a}$, —NHSO$_2$R$^{10}$, —S—C$_{1-4}$alkyl, —S(O)C$_{1-4}$ alkyl, —S(O)$_2$C$_{1-4}$alkyl, —SO$_2$NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, F, Cl, Br, I, C$_{1-4}$ alkyl, CN, —OH, —O—R$^{11}$, OCF$_3$, —O(CO)—R$^{13}$, —OS(O)$_2$C$_{1-4}$alkyl, —NR$^{12}$R$^{12a}$, —C(O)R$^{13}$, —NHC(O)R$^{13}$, —SR$^{11}$, —S(O)R$^{11}$, —S(O)$_2$R$^{11}$, —NHSO$_2$R$^{10}$, and —SO$_2$NR$^{12}$R$^{12a}$;

R$^4$ is selected from the group H, F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic system containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group H, C$_{1-3}$ alkyl and C$_{1-3}$ alkoxy;

R$^8$ is selected from the group H, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl) oxycarbonyl, (C$_{6-10}$ aryl)methylcarbonyl, (C$_{1-4}$ alkyl) carbonyloxy(C$_{14}$ alkoxy)carbonyl, C$_{6-10}$ arylcarbonyloxy (C$_{1-4}$ alkoxy)carbonyl, C$_{1-6}$ alkylaminocarbonyl, phenylaminocarbonyl, phenyl(C$_{1-4}$ alkoxy)carbonyl, and NR$^5$R$^{5a}$(C$_{1-6}$ alkyl)carbonyl;

R$^9$ is selected from H, C$_{1-4}$ alkyl, C$_{1-4}$ alkenyl, C$_{1-4}$ alkynyl, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl)oxycarbonyl, (C$_{6-10}$ aryl) methylcarbonyl, (C$_{1-4}$ alkyl)carbonyloxy(C$_{1-4}$ alkoxy) carbonyl, C$_{6-10}$ arylcarbonyloxy (C$_{1-4}$ alkoxy)carbonyl, C$_{1-6}$ alkylaminocarbonyl, phenylaminocarbonyl, phenyl (C$_{1-4}$ alkoxy)carbonyl, and NR$^5$R$^{5a}$(C$_{1-6}$ alkyl)carbonyl;

R$^{10}$ is selected from the group C$_{1-4}$ alkyl and phenyl;

R$^{11}$ is selected from C$_{1-6}$ alkyl, C$_{1-6}$ haloalkyl, C$_{1-6}$ alkyl substituted with C$_{3-6}$cycloalkyl substituted with 0–2 R$^{3e}$, C$_{2-6}$ alkenyl, C$_{2-6}$ alkynyl, C$_{3-6}$ carbocycle substituted with 0–2 R$^{3e}$;

R$^{12}$ and R$^{12a}$ are independently selected from H, C$_{1-6}$ alkyl, C$_{1-6}$ alkyl substituted with C$_{3-6}$cycloalkyl substituted with 0–2 R$^{3e}$, and C$_{3-6}$ carbocycle substituted with 0–2 R$^{3e}$;

alternatively, R$^{12}$ and R$^{12a}$ can join to form 4–7 membered heterocyclic ring;

R$^{13}$ is selected from the group H, C$_{1-6}$ alkyl, C$_{1-6}$ haloalkyl, C$_{1-6}$ alkoxy, C$_{2-6}$ alkenyl, C$_{2-6}$ alkynyl, —O—C$_{2-6}$ alkenyl, —O—C$_{2-6}$ alkynyl, NR$^{12}$R$^{12a}$, C$_{3-6}$carbocycle, and —O—C$_{3-6}$carbocycle; and t is selected from 0 and 1.

[2] In a preferred embodiment, the present invention provides compounds of formula (I), wherein:

R$^2$ is selected from the group methyl substituted with 0–3 R$^{3f}$, C$_{1-5}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$, and 3–6 membered heterocyclic system containing 1–3 heteroatoms selected from the group O, N, and S, substituted with 0–2 R$^{3d}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;

R$^3$ and R$^{3a}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ and R$^{3c}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group H, Cl, F, C$_{1-4}$ alkyl substituted with 0–2 R$^{3e}$, C$_{3-6}$ carbocycle substituted with 0–2 R$^{3e}$, phenyl substituted with 0–5 R$^{3e}$, and a 5–6 membered heterocyclic system containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, CH(CH$_3$)$_2$, OCH$_3$, OC$_2$H$_5$, and OCH(CH$_3$)$_2$.

[3] In another preferred embodiment, the present invention provides compounds of formula (I), wherein:

P is O;

Ring A is:

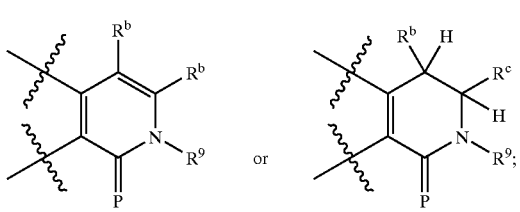

R$^b$, at each occurrence, is selected from H, F, Cl, and Br, C$_{1-4}$ alkyl, CN, C$_{1-4}$ alkyl-NH—, NH$_2$;

R$^c$ is selected from H and methyl;

W is CR$^3$;

X is CR$^{3a}$;

Y is CR$^{3b}$;

Z is CR$^{3c}$;

R$^2$ is selected from the group methyl substituted with 0–3 R$^{3f}$, C$_{1-3}$ alkyl substituted with 0–2 R$^4$, C$_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3e}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;

$R^{3f}$, at each occurrence, is independently selected from the group H, F, Cl, Br, I, $C_{1-4}$ alkyl, CN, —OH, —O—$R^{11}$, —$O(CO)$—$R^{13}$, —$SR^{11}$, —$S(O)R^{11}$, —$S(O)_2R^{11}$, and —$NR^{12}R^{12a}$;

$R^4$ is selected from the group H, Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H;

$R^9$ is H, methyl, ethyl, propyl, and i-propyl;

$R^{11}$ is selected from methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl; and $R^{12}$ and $R^{12a}$ are independently selected from H, methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

[4] In another preferred embodiment, the present invention provides compounds of formula (I), wherein:

$R^2$ is selected from the group methyl substituted with 0–3 $R^{3f}$, $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3e}$, at each occurrence, is independently selected from the group $CH_3$, —OH, $OCH_3$, $OCF_3$, F, Cl, and —$NR^5R^{5a}$;

$R^{3f}$, at each occurrence, is independently selected from the group H, F, Cl, Br, I, $C_{1-4}$ alkyl, —OH, CN, —O—$R^{11}$, —$O(CO)$—$R^{13}$, and —$NR^{12}R^{12a}$, —$SR^{11}$, —$S(O)R^{11}$, —$S(O)_2R^{11}$, and —$OS(O)_2$methyl;

$R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and $R^9$ is selected from H and methyl.

[5] In another preferred embodiment, the present invention provides compounds of formula (I), wherein:

$R^2$ is selected from the group methyl substituted with 0–2 $R^{3f}$, methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;

$R^{3e}$, at each occurrence, is independently selected from the group $CH_3$, —OH, $OCH_3$, $OCF_3$, F, Cl, and —$NR^5R^{5a}$;

$R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H.

[6] In another preferred embodiment, the present invention provides compounds of formula (I), wherein:

$R^1$ is selected from methyl, ethyl, propyl, i-propyl, butyl, cyclopropyl, $CF_3$, $CF_2CH_3$, CN, and hydroxymethyl;

$R^2$ is selected from the group methyl substituted with 0–2 $R^{3f}$, methyl substituted with 0–2 $R^4$, ethyl substituted with 0–2 $R^4$, propyl substituted with 0–1 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$;

$R^3$, $R^{3b}$, and $R^{3c}$ are H;

$R^{3e}$ is $CH_3$;

$R^{3f}$, at each occurrence, is independently selected from the group H, F, Cl, Br, I, $C_{1-4}$ alkyl, CN, —OH, —O—$R^{11}$, —$SR^{11}$, —$S(O)R^{11}$, —$S(O)_2R^{11}$, and —$NR^{12}R^{12a}$;

$R^4$ is selected from the group H, cyclopropyl substituted with 0–1 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^{12}$ and $R^{12a}$ are independently selected from H, methyl, ethyl, propyl, and i-propyl, and $C_{3-6}$ carbocycle substituted with 0–2 $R^{3e}$ wherein the $C_{3-6}$ carbocycle is selected from cyclopropyl.

[7] Preferred compounds of the present invention are those compounds wherein the compound is of formula (Ic):

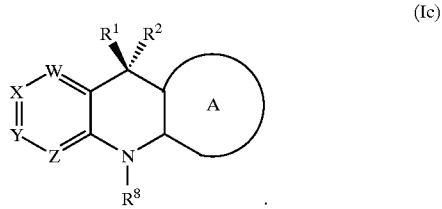

(Ic)

[8] Preferred compounds of the present invention include compounds of formula (I) wherein the compound of formula (I) is selected from the compounds shown in Table 1.

7-fluoro-2-methyl-5-[(6-methyl-2-pyridinyl)methyl]-5-(trifluoromethyl)-5,10-dihydrobenzo[b]-1,7-naphthyridin-1(2H)-one;
5-(2-cyclopropylethynyl)-7-fluoro-5-(trifluoromethyl)-5,10-dihydrobenzo[b]-1,7-naphthyridin-1(2H)-one;
7-fluoro-5-propyl-5-(trifluoromethyl)-5,10-dihydrobenzo[b]-1,7-naphthyridin-1(2H)-one;
5-butyl-7-fluoro-5-(trifluoromethyl)-5,10-dihydrobenzo[b]-1,7-naphthyridin-1(2H)-one;
7-fluoro-5-(4-fluorophenylmethyl)-5-(trifluoromethyl)-5,10-dihydrobenzo[b]-1,7-naphthyridin-1(2H)-one;
7-fluoro-5-(2-pyridylmethyl)-5-(trifluoromethyl)-5,10-dihydrobenzo[b]-1,7-naphthyridin-1(2H)-one;
7-fluoro-5-(isopropyl)-5-(trifluoromethyl)-5,10-dihydrobenzo[b]-1,7-naphthyridin-1(2H)-one;
7-fluoro-5-(3-pyridylmethyl)-5-(trifluoromethyl)-5,10-dihydrobenzo[b]-1,7-naphthyridin-1(2H)-one;
7-fluoro-5-(4-pyridylmethyl)-5-(trifluoromethyl)-5,10-dihydrobenzo[b]-1,7-naphthyridin-1(2H)-one;
7-fluoro-5-(3-propynyl)-5-(trifluoromethyl)-5,10-dihydrobenzo[b]-1,7-naphthyridin-1(2H)-one;
7-fluoro-5-(2-pyridylethynyl)-5-(trifluoromethyl)-5,10-dihydrobenzo[b]-1,7-naphthyridin-1(2H)-one;
7-fluoro-5-(2-(2-pyridyl)ethyl)-5-(trifluoromethyl)-5,10-dihydrobenzo[b]-1,7-naphthyridin-1(2H)-one;
3-chloro-7-fluoro-5-propyl-5-(trifluoromethyl)-5,10-dihydrobenzo[b]-1,7-naphthyridin-1(2H)-one;
7-fluoro-5-(3-propenyl)-5-(trifluoromethyl)-5,10-dihydrobenzo[b]-1,7-naphthyridin-1(2H)-one;
5-(2-cyclopropylethyl)-7-fluoro-5-(trifluoromethyl)-5,10-dihydrobenzo[b]-1,7-naphthyridin-1(2H)-one;
7-fluoro-5-(ethynyl)-5-(trifluoromethyl)-5,10-dihydrobenzo[b]-1,7-naphthyridin-1(2H)-one;
7-fluoro-5-(2-ethoxyethyl)-5-(trifluoromethyl)-5,10-dihydrobenzo[b]-1,7-naphthyridin-1(2H)-one;
5-Butyl-7-chloro-5-trifluoromethyl-5,10-dihydrobenzo[b]-1,7-naphthyridin-1(2H)-one;
7-Chloro-5-(2-pyridylmethyl)-5-trifluoromethyl-5,10-dihydrobenzo[b]-1,7-naphthyridin-1(2H)-one;
7-Chloro-5-(2-cyclopropylethyl)-5-trifluoromethyl-5,10-dihydrobenzo[b]-1,7-naphthyridin-1(2H)-one;
7-Chloro-5-cyclopropylethynyl-5-trifluoromethyl-5,10-dihydrobenzo[b]-1,7-naphthyridin-1(2H)-one;
7-Chloro-5-(N-cyclopropylaminomethyl)-5-trifluoromethyl-5,10-dihydrobenzo[b]-1,7-naphthyridin-1(2H)-one;
7-Chloro-5-hydroxymethyl-5-trifluoromethyl-5,10-dihydrobenzo[b]-1,7-naphthyridin-1(2H)-one;
7-Chloro-3-methyl-5-(2-pyridylmethyl)-5-trifluoromethyl-5,10-dihydrobenzo[b]-1,7-naphthyridin-1(2H)-one;
7-Chloro-5-(2-cyclopropylethyl)-3-methyl-5-trifluoromethyl-5,10-dihydrobenzo[b]-1,7-naphthyridin-1(2H)-one;
7-Chloro-5-(n-propoxymethyl)-5-trifluoromethyl-5,10-dihydrobenzo[b]-1,7-naphthyridin-1(2H)-one;
7-Chloro-5-(i-propoxymethyl)-5-trifluoromethyl-5,10-dihydrobenzo[b]-1,7-naphthyridin-1(2H)-one;
7-Chloro-5-(2-methoxyethyl)-5-trifluoromethyl-5,10-dihydrobenzo[b]-1,7-naphthyridin-1(2H)-one;
7-Chloro-5-(i-propylaminomethyl)-5-trifluoromethyl-5,10-dihydrobenzo[b]-1,7-naphthyridin-1(2H)-one;
7-Chloro-5-(N-methyl-N-i-propylaminomethyl)-5-trifluoromethyl-5,10-dihydrobenzo[b]-1,7-naphthyridin-1(2H)-one;
7-Chloro-5-(cyclopropylaminomethyl)-5-trifluoromethyl-5,10-dihydrobenzo[b]-1,7-naphthyridin-1(2H)-one;
7-Chloro-5-(n-propylaminomethyl)-5-trifluoromethyl-5,10-dihydrobenzo[b]-1,7-naphthyridin-1(2H)-one;
7-Chloro-5-(cyclobutylaminomethyl)-5-trifluoromethyl-5,10-dihydrobenzo[b]-1,7-naphthyridin-1(2H)-one;
7-Chloro-5-(i-butylaminomethyl)-5-trifluoromethyl-5,10-dihydrobenzo[b]-1,7-naphthyridin-1(2H)-one;
7-Chloro-5-(i-propoxymethyl)-5-trifluoromethyl-5,10-dihydrobenzo[b]-1,7-naphthyridin-1(2H)-one;
7-Cyano-5-(n-butyl)-5-trifluoromethyl-5,10-dihydrobenzo[b]-1,7-naphthyridin-1(2H)-one;
7-Cyano-5-(i-propoxymethyl)-5-trifluoromethyl-5,10-dihydrobenzo[b]-1,7-naphthyridin-1(2H)-one;
7-Chloro-5-(cyclopropylsulfanylmethyl)-5-trifluoromethyl-5,10-dihydrobenzo[b]-1,7-naphthyridin-1(2H)-one;
7-Chloro-5-(cyclopropanesulfinylmethyl)-5-trifluoromethyl-5,10-dihydrobenzo[b]-1,7-naphthyridin-1(2H)-one;
7-Chloro-5-(t-butylsulfinylmethyl)-5-trifluoromethyl-5,10-dihydrobenzo[b]-1,7-naphthyridin-1(2H)-one;
7-Chloro-5-(methylsulfanylmethyl)-5-trifluoromethyl-5,10-dihydrobenzo[b]-1,7-naphthyridin-1(2H)-one;
7-Chloro-5-(ethylsulfanylmethyl)-5-trifluoromethyl-5,10-dihydrobenzo[b]-1,7-naphthyridin-1(2H)-one;
7-Chloro-5-(i-propylsulfanylmethyl)-5-trifluoromethyl-5,10-dihydrobenzo[b]-1,7-naphthyridin-1(2H)-one;
7-Fluoro-5-(i-propylsulfanylmethyl)-5-trifluoromethyl-5,10-dihydrobenzo[b]-1,7-naphthyridin-1(2H)-one;
7-Chloro-5-(t-butylsulfanylmethyl)-5-trifluoromethyl-5,10-dihydrobenzo[b]-1,7-naphthyridin-1(2H)-one;
7-Chloro-5-(cyclopropylmethoxymethyl)-5-trifluoromethyl-5,10-dihydrobenzo[b]-1,7-naphthyridin-1(2H)-one;
7-Chloro-5-(cyclobutoxymethyl)-5-trifluoromethyl-5,10-dihydrobenzo[b]-1,7-naphthyridin-1(2H)-one;
5-(Cyclobutoxymethyl)-7-fluoro-5-trifluoromethyl-5,10-dihydrobenzo[b]-1,7-naphthyridin-1(2H)-one;
5-(Cyclopropylmethoxymethyl)-7-fluoro-5-trifluoromethyl-5,10-dihydrobenzo[b]-1,7-naphthyridin-1(2H)-one;
7-Chloro-3-methyl-5-(i-propoxymethyl)-5-trifluoromethyl-5,10-dihydrobenzo[b]-1,7-naphthyridin-1(2H)-one;
7-Chloro-3-methyl-5-(n-butyl)-5-trifluoromethyl-5,10-dihydrobenzo[b]-1,7-naphthyridin-1(2H)-one;
7-Cyano-3-methyl-5-(n-butyl)-5-trifluoromethyl-5,10-dihydrobenzo[b]-1,7-naphthyridin-1(2H)-one;
7-Chloro-2-methyl-5-(i-propoxymethyl)-5-trifluoromethyl-5,10-dihydrobenzo[b]-1,7-naphthyridin-1(2H)-one;
3,7-Dichloro-5-(n-butyl)-5-trifluoromethyl-5,10-dihydrobenzo[b]-1,7-naphthyridin-1(2H)-one;
4,7-Dichloro-5-(n-butyl)-5-trifluoromethyl-5,10-dihydrobenzo[b]-1,7-naphthyridin-1(2H)-one;
7-Chloro-5-(ethoxyethyl)-5-trifluoromethyl-5,10-dihydrobenzo[b]-1,7-naphthyridin-1(2H)-one;
7-Chloro-5-(n-butyl)-5-methyl-5,10-dihydrobenzo[b]-1,7-naphthyridin-1(2H)-one;

7-Chloro-5-(i-propoxymethyl)-5-methyl-5,10-dihydrobenzo[b]-1,7-naphthyridin-1(2H)-one;
7-Chloro-5-(n-butyl)-5-cyano-5,10-dihydrobenzo[b]-1,7-naphthyridin-1(2H)-one;
7-Chloro-5-(n-butyl)-5-(hydroxymethyl)-5,10-dihydrobenzo[b]-1,7-naphthyridin-1(2H)-one;
7-Chloro-5-(n-butyl)-5-difluoromethyl-5,10-dihydrobenzo[b]-1,7-naphthyridin-1(2H)-one;
7-Chloro-5-(i-propoxymethyl)-5-difluoromethyl-5,10-dihydrobenzo[b]-1,7-naphthyridin-1(2H)-one;
5-(n-Butyl)-5-(1,1-difluoroethyl)-7-Fluoro-5,10-dihydrobenzo[b]-1,7-naphthyridin-1(2H)-one;
7-Chloro-5-(n-butyl)-5-(1,1-difluoroethyl)-5,10-dihydrobenzo[b]-1,7-naphthyridin-1(2H)-one;
7-Cyano-5-(n-butyl)-5-(1,1-difluoroethyl)-5,10-dihydrobenzo[b]-1,7-naphthyridin-1(2H)-one;
7-Chloro-5-(ethoxymethyl)-5-(1,1-difluoroethyl)-5,10-dihydrobenzo[b]-1,7-naphthyridin-1(2H)-one;
5-(allyl)-7-fluoro-5-trifluoromethyl-5,10-dihydrobenzo[b]-1,7-naphthyridin-1(2H)-one;
5-(2-methyl-1-propenyl)-7-fluoro-5-trifluoromethyl-5,10-dihydrobenzo[b]-1,7-naphthyridin-1(2H)-one;
5-(1-propynyl)-7-fluoro-5-trifluoromethyl-5,10-dihydrobenzo[b]-1,7-naphthyridin-1(2H)-one;
5-(cyanomethyl)-7-fluoro-5-trifluoromethyl-5,10-dihydrobenzo[b]-1,7-naphthyridin-1(2H)-one;
5-(2-(ethylamino)ethyl)-7-fluoro-5-trifluoromethyl-5,10-dihydrobenzo[b]-1,7-naphthyridin-1(2H)-one;
5-(2-(dimethylamino)ethyl)-7-fluoro-5-trifluoromethyl-5,10-dihydrobenzo[b]-1,7-naphthyridin-1(2H)-one;
5-(2-(methylamino)ethyl)-7-fluoro-5-trifluoromethyl-5,10-dihydrobenzo[b]-1,7-naphthyridin-1(2H)-one;
5-(2-ethoxyethyl)-7-fluoro-5-trifluoromethyl-5,10-dihydrobenzo[b]-1,7-naphthyridin-1(2H)-one;
5-(2-(i-propylamino)ethyl)-7-fluoro-5-trifluoromethyl-5,10-dihydrobenzo[b]-1,7-naphthyridin-1(2H)-one;
5-(2-(diethylamino)ethyl)-7-fluoro-5-trifluoromethyl-5,10-dihydrobenzo[b]-1,7-naphthyridin-1(2H)-one;
5-(2-(cyclopropylamino)ethyl)-7-fluoro-5-trifluoromethyl-5,10-dihydrobenzo[b]-1,7-naphthyridin-1(2H)-one;
5-(pentyl)-7-fluoro-5-trifluoromethyl-5,10-dihydrobenzo[b]-1,7-naphthyridin-1(2H)-one;
5-(i-butyl)-7-fluoro-5-trifluoromethyl-5,10-dihydrobenzo[b]-1,7-naphthyridin-1(2H)-one;
5-(vinyl)-7-fluoro-5-trifluoromethyl-5,10-dihydrobenzo[b]-1,7-naphthyridin-1(2H)-one;
5-(imidazolylethyl)-7-fluoro-5-trifluoromethyl-5,10-dihydrobenzo[b]-1,7-naphthyridin-1(2H)-one;
5-(pyrazolylethyl)-7-fluoro-5-trifluoromethyl-5,10-dihydrobenzo[b]-1,7-naphthyridin-1(2H)-one;
5-(1,2,4-triazolylethyl)-7-fluoro-5-trifluoromethyl-5,10-dihydrobenzo[b]-1,7-naphthyridin-1(2H)-one;
5-(i-propylaminomethyl)-7-fluoro-5-trifluoromethyl-5,10-dihydrobenzo[b]-1,7-naphthyridin-1(2H)-one;
5-(i-propoxymethyl)-7-fluoro-5-trifluoromethyl-5,10-dihydrobenzo[b]-1,7-naphthyridin-1(2H)-one;
5-(2-(methylethylamino)ethyl)-7-fluoro-5-trifluoromethyl-5,10-dihydrobenzo[b]-1,7-naphthyridin-1(2H)-one;
5-(2-(i-propylethylamino)ethyl)-7-fluoro-5-trifluoromethyl-5,10-dihydrobenzo[b]-1,7-naphthyridin-1(2H)-one;
5-(2-(pyrrolidinyl)ethyl)-7-fluoro-5-trifluoromethyl-5,10-dihydrobenzo[b]-1,7-naphthyridin-1(2H)-one;
5-(2-(methoxy)ethyl)-7-fluoro-5-trifluoromethyl-5,10-dihydrobenzo[b]-1,7-naphthyridin-1(2H)-one;
5-(i-propoxymethyl)-7-fluoro-5-trifluoromethyl-5,10-dihydrobenzo[b]-1,7-naphthyridin-1(2H)-one;
5-(3-pentanylaminomethyl)-7-fluoro-5-trifluoromethyl-5,10-dihydrobenzo[b]-1,7-naphthyridin-1(2H)-one;
5-(dimethoxymethyl)-7-fluoro-5-trifluoromethyl-5,10-dihydrobenzo[b]-1,7-naphthyridin-1(2H)-one;
5-(i-butylaminomethyl)-7-fluoro-5-trifluoromethyl-5,10-dihydrobenzo[b]-1,7-naphthyridin-1(2H)-one;
5-(cyclopropylmethylaminomethyl)-7-fluoro-5-trifluoromethyl-5,10-dihydrobenzo[b]-1,7-naphthyridin-1(2H)-one;
5-(allylaminomethyl)-7-fluoro-5-trifluoromethyl-5,10-dihydrobenzo[b]-1,7-naphthyridin-1(2H)-one;
5-((R)-sec-butylaminomethyl)-7-fluoro-5-trifluoromethyl-5,10-dihydrobenzo[b]-1,7-naphthyridin-1(2H)-one;
5-((S)-sec-butylaminomethyl)-7-fluoro-5-trifluoromethyl-5,10-dihydrobenzo[b]-1,7-naphthyridin-1(2H)-one;
5-(diethoxymethyl)-7-fluoro-5-trifluoromethyl-5,10-dihydrobenzo[b]-1,7-naphthyridin-1(2H)-one;
3-chloro-5-(propyl)-7-fluoro-5-trifluoromethyl-5,10-dihydrobenzo[b]-1,7-naphthyridin-1(2H)-one;
5-(butyl)-7-fluoro-2-methyl-5-trifluoromethyl-5,10-dihydrobenzo[b]-1,7-naphthyridin-1(2H)-one;
5-(2-(i-propoxy)ethyl)-7-fluoro-2-methyl-5-trifluoromethyl-5,10-dihydrobenzo[b]-1,7-naphthyridin-1(2H)-one;
5-(i-propylaminomethyl)-7-fluoro-2-methyl-5-trifluoromethyl-5,10-dihydrobenzo[b]-1,7-naphthyridin-1(2H)-one;
5-(i-propoxymethyl)-7-fluoro-2-methyl-5-trifluoromethyl-5,10-dihydrobenzo[b]-1,7-naphthyridin-1(2H)-one;
5-(2-ethoxyethyl)-7-fluoro-2-methyl-5-trifluoromethyl-5,10-dihydrobenzo[b]-1,7-naphthyridin-1(2H)-one;
5-(sec-butylaminomethyl)-7-fluoro-2-methyl-5-trifluoromethyl-5,10-dihydrobenzo[b]-1,7-naphthyridin-1(2H)-one;
5-(cyclopentylaminomethyl)-7-fluoro-5-trifluoromethyl-5,10-dihydrobenzo[b]-1,7-naphthyridin-1(2H)-one;
5-(cyclobutylaminomethyl)-7-fluoro-5-trifluoromethyl-5,10-dihydrobenzo[b]-1,7-naphthyridin-1(2H)-one;
5-(dimethylaminomethyl)-7-fluoro-5-trifluoromethyl-5,10-dihydrobenzo[b]-1,7-naphthyridin-1(2H)-one;
5-(pyrrolidinylmethyl)-7-fluoro-5-trifluoromethyl-5,10-dihydrobenzo[b]-1,7-naphthyridin-1(2H)-one;
5-(cyclopropylaminomethyl)-7-fluoro-5-trifluoromethyl-5,10-dihydrobenzo[b]-1,7-naphthyridin-1(2H)-one;
5-(2-(dimethoxy)ethyl)-7-fluoro-5-trifluoromethyl-5,10-dihydrobenzo[b]-1,7-naphthyridin-1(2H)-one;
5-(2-(diethoxy)ethyl)-7-fluoro-5-trifluoromethyl-5,10-dihydrobenzo[b]-1,7-naphthyridin-1(2H)-one;
5-(2-(1,3-dioxolanyl)methyl)-7-fluoro-5-trifluoromethyl-5,10-dihydrobenzo[b]-1,7-naphthyridin-1(2H)-one; and
5-(2-(methoxy)ethyl)-7-fluoro-5-trifluoromethyl-5,10-dihydrobenzo[b]-1,7-naphthyridin-1(2H)-one.

The present invention also provides a novel pharmaceutical composition comprising a pharmaceutically acceptable carrier and a therapeutically effective amount of a compound of formula (I) or a pharmaceutically acceptable salt form thereof The compositions and methods of use comprising the compounds of the present invention include compositions and methods of use comprising the compounds of the present invention and stereoisomeric forms thereof, mixtures of stereoisomeric forms thereof, complexes thereof, crystalline forms thereof, prodrug forms thereof and pharmaceutically acceptable salt forms thereof In another embodiment, the present invention provides a novel method for treating HIV infection which comprises administering to a host in need of such treatment a therapeutically effective amount of a compound of formula (I) or a pharmaceutically acceptable salt form thereof In another embodiment, the present invention provides a novel method of treating HIV infection which comprises administering, in combination, to a host in need thereof a therapeutically effective amount of:

(a) a compound of formula (I); and
(b) at least one compound selected from the group consisting of HIV reverse transcriptase inhibitors and HIV protease inhibitors.

In another embodiment, the present invention provides a novel method of treating HIV infection which comprises administering, in combination, to a host in need thereof a therapeutically effective amount of:

(a) a compound of formula (I); and
(b) at least one compound selected from the group consisting of HIV reverse transcriptase inhibitors, HIV protease inhibitors, CCR-5 inhibitors, and fusion inhibitors.

Preferred reverse transcriptase inhibitors useful in the above method of treating HIV infection are selected from the group AZT, ddC, ddI, d4T, 3TC, delavirdine, efavirenz, nevirapine, Ro 18,893, trovirdine, MKC-442, HBY 097, HBY1293, GW867, ACT, UC-781, UC-782, RD4-2025, MEN 10979, AG1549 (S1153), TMC-120, TMC-125, Calanolide A, and PMPA. Preferred protease inhibitors useful in the above method of treating HIV infection are selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, ABT-378, DMP-450, AG-1776, VX-175, MK-944, and VX-478, the CCR-5 inhibitor is selected from TAK-779 (Takeda), SC-351125 (SCH-C, Schering) and SCH-D (Schering), and the fusion inhibitor is selected from T-20 amd T1249.

In an even more preferred embodiment, the reverse transcriptase inhibitor is selected from the group AZT, efavirenz, and 3TC and the protease inhibitor is selected from the group saquinavir, ritonavir, nelfinavir, and indinavir.

In a still further preferred embodiment, the reverse transcriptase inhibitor is AZT.

In another still further preferred embodiment, the protease inhibitor is indinavir.

In another embodiment, the present invention provides a pharmaceutical kit useful for the treatment of HIV infection, which comprises a therapeutically effective amount of:

(a) a compound of formula (I); and,
(b) at least one compound selected from the group consisting of HIV reverse transcriptase inhibitors and HIV protease inhibitors, in one or more sterile containers.

In another embodiment, the present invention provides novel tricyclic 2-pyridone compounds for use in therapy.

In another embodiment, the present invention provides the use of novel tricyclic 2-pyridone compounds for the manufacture of a medicament for the treatment of HIV infection.

In another embodiment, the present invention provides that Ring A is

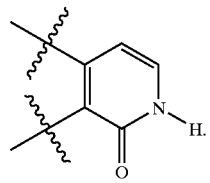

In another embodiment, the present invention provides that Ring A is

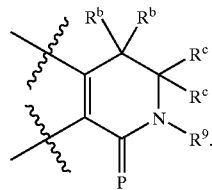

In another embodiment, the present invention provides that $R^1$ is $CF_3$, $CF_2CH_3$, and $CHF_2$.

In another embodiment, the present invention provides that $R^1$ is selected from the group $CF_3$, $C_2F_5$, $CF_2CH_3$, $CHF_2$, $CH_2F$ and cyclopropyl.

In another embodiment, the present invention provides that $R^1$ is methyl, ethyl, propyl, i-propyl and butyl.

In another embodiment, the present invention provides that $R^1$ is CN and hydroxymethyl.

In another embodiment, the present invention provides that $R^2$ is selected from the group methyl substituted with 0–3 $R^{3f}$, $C_{1-5}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$, and 3–6 membered heterocyclic system containing 1–3 heteroatoms selected from the group O, N, and S, substituted with 0–2 $R^{3d}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl.

In another embodiment, the present invention provides that $R^2$ is selected from the group methyl substituted with 0–3 $R^{3f}$, $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$.

In another embodiment, the present invention provides that $R^2$ is selected from the group methyl substituted with 0–3 $R^{3f}$, $C_{1-3}$ alkyl substituted with 1 $R^4$, $C_{2-3}$ alkenyl substituted with 1 $R^4$, and $C_{2-3}$ alkynyl substituted with 1 $R^4$.

In another embodiment, the present invention provides that $R^2$ is selected from the group methyl substituted with 0–2 $R^{3f}$, methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$.

In another embodiment, the present invention provides that $R^2$ is selected from the group methyl substituted with 0–2 $R^{3f}$, methyl substituted with 0–2 $R^4$, ethyl substituted with 0–2 $R^4$, propyl substituted with 0–1 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$.

In another embodiment, $R^2$ is selected from the group methyl substituted with 0–2 $R^{3f}$, methyl substituted with 0–2 $R^4$, and ethyl substituted with 0–2 $R^4$.

In another embodiment, $R^2$ is $R^{2c}$.

In another embodiment, the present invention provides that $R^{3f}$, at each occurrence, is independently selected from the group H, F, Cl, Br, I, $C_{1-4}$ alkyl, CN, —OH, —O—$R^{11}$, —O(CO)—$R^{13}$, —S$R^{11}$, —S(O)$R^{11}$, —S(O)$_2R^{11}$, and —N$R^{12}R^{12a}$.

In another embodiment, the present invention provides that $R^{3f}$, at each occurrence, is independently selected from the group H, F, Cl, Br, I, $C_{1-4}$ alkyl, —OH, CN, —O—$R^{11}$, —O(CO)—$R^{13}$, and —$NR^{12}R^{12a}$, —$SR^{11}$, —S(O)$R^{11}$, —S(O)$_2R^{11}$, and —OS(O)$_2$methyl.

In another embodiment, the present invention provides that $R^{3f}$, at each occurrence, is independently selected from the group H, F, Cl, Br, I, $C_{1-4}$ alkyl, CN, —OH, —O—$R^{11}$, —$SR^{11}$, —S(O)$R^{11}$, —S(O)$_2R^{11}$, and —$NR^{12}R^{12a}$.

In another embodiment, the present invention provides that $R^4$ is selected from the group H, Cl, F, $C_{1-4}$ alkyl substituted with 0–2 $R^{3e}$, $C_{3-6}$ carbocycle substituted with 0–2 $R^{3e}$, phenyl substituted with 0–5 $R^{3e}$, and a 5–6 membered heterocyclic system containing 1–3 heteroatoms selected from the group O, N, and S, substituted with 0–2 $R^{3e}$.

In another embodiment, the present invention provides that $R^4$ is selected from the group H, Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl.

In another embodiment, the present invention provides that $R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl.

In another embodiment, the present invention provides that $R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl.

In another embodiment, the present invention provides that $R^8$ is H.

In another embodiment, the present invention provides that $R^9$ is H, methyl, ethyl, propyl, and i-propyl.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated. All tautomers of shown or described compounds are also considered to be part of the present invention.

As used herein, the term "tricyclic 2-pyridones" is intended to include the compounds 5,10-Dihydro-2H-benzo[b][1,7]naphthyridin-1-one which are represented by the compounds of Formula I.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbonyl group or double bond be part (i.e., within) of the ring.

When any variable (e.g., $R^b$) occurs more than one time in any constituent or formula for a compound, its definition at each occurrence is independent of its definition at every other occurrence. Thus, for example, if a group is shown to be substituted with 0–2 $R^4$, then said group may optionally be substituted with up to two $R^4$ groups and $R^4$ at each occurrence is selected independently from the definition of $R^4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, the following terms and expressions have the indicated meanings.

As used herein, "alkyl" is intended to include both branched and straight-chain saturated aliphatic hydrocarbon groups having the specified number of carbon atoms. By way of illustration, the term "$C_{1-10}$ alkyl" or "$C_1$–$C_{10}$ alkyl" is intended to include $C_1$, $C_2$, $C_3$, $C_4$, $C_5$, $C_6$, $C_7$, $C_8$, $C_9$, and $C_{10}$ alkyl groups. "$C_{1-4}$ alkyl" is intended to include $C_1$, $C_2$, $C_3$, and $C_4$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon-carbon bonds which may occur in any stable point along the chain, such as ethenyl, propenyl and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl, propynyl and the like. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3, 4, 5, 6, or 7-membered monocyclic or bicyclic or 7, 8, 9, 10, 11, 12 or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, or tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. An oxo group may be a substituent on a nitrogen heteroatom to form an N-oxide. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 1,3-dioxolanyl, 1,3-dioxanyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, PMPA, and 3TC. Examples of non-nucleoside RT inhibitors include, but are no limited to, delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), HBY1293 (Hoechst), GW867 (Glaxo Wellcome), ACT (Korean Research Institute), UC-781 (Rega Institute), UC-782 (Rega Institute), RD4-2025 (Tosoh Co. Ltd.), MEN 10979 (Menarini Farmaceutici) AG1549 (S1153; Agouron), TMC-120, TMC-125, and Calanolide A.

As used herein, "HIV protease inhibitor" is intended to refer to compounds that inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), tipranavir (Pharmacia and Upjohn, U-140690), DMP-450 (DuPont), AG-1776, VX-175, MK-944, VX-478 and ABT-378. Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Examples of prodrugs at $R^8$ and at $R^9$ are $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention alone or an amount of the combination of compounds claimed or an amount of a compound of the present invention in combination with other active ingredients effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Other features of the invention will become apparent in the course of the following descriptions of exemplary embodiments that are given for illustration of the invention and are not intended to be limiting thereof.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

SCHEME 1

SCHEME 3

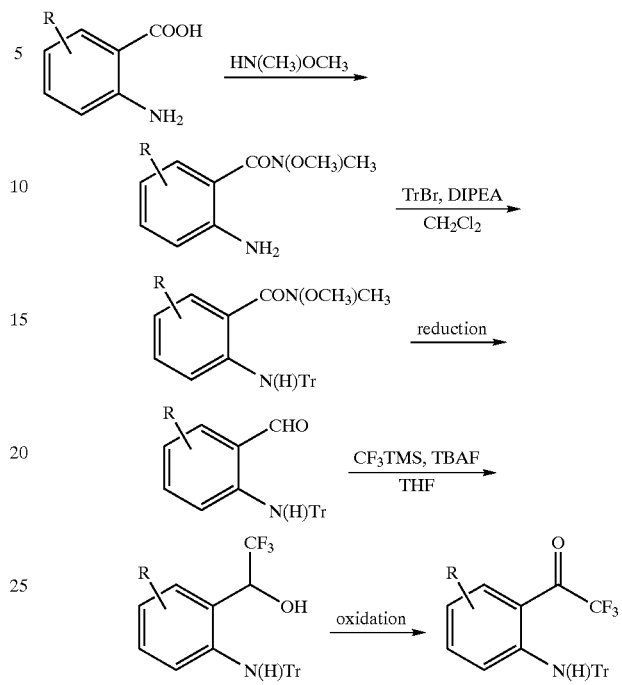

Scheme 1 illustrates a method of preparing keto-anilines from an appropriately substituted 2-aminobenzoic acid (wherein R represents $R^3$, $R^{3a}$, $R^{3b}$, and $R^{3c}$). The acid is converted to its N-methoxy-N-methyl amide derivative which can then be displaced to obtain the $R^1$-substituted ketone. The keto-anilines are useful intermediates for the presently claimed compounds.

SCHEME 2

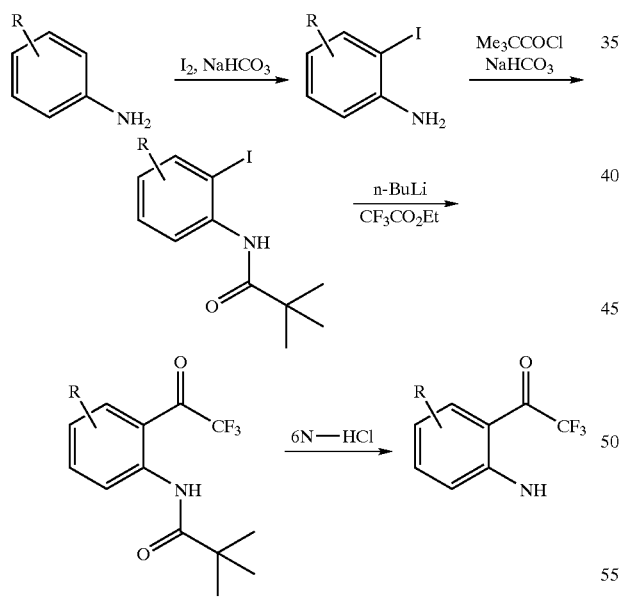

Scheme 2 describes another method of preparing keto-anilines, this time from an appropriately substituted aniline. After iodination and amine protection, a group such as trifluoromethyl can be introduced using a strong base and ethyl trifluoroacetate. Deprotection provides the keto-aniline. Additional means of preparing keto-anilines are known to one of skill in the art, e.g, Houpis et al, *Tetr. Lett.* 1994, 35(37), 6811–6814, the contents of which are hereby incorporated herein by reference.

Another method of making 2-trifluoroacetylanilines is shown in Scheme 3. After forming the protected aniline, the amide is then reduced and the trifluoromethyl group added. Oxidation with an oxidant, such as $MnO_2$, provides the useful intermediate.

Scheme 4

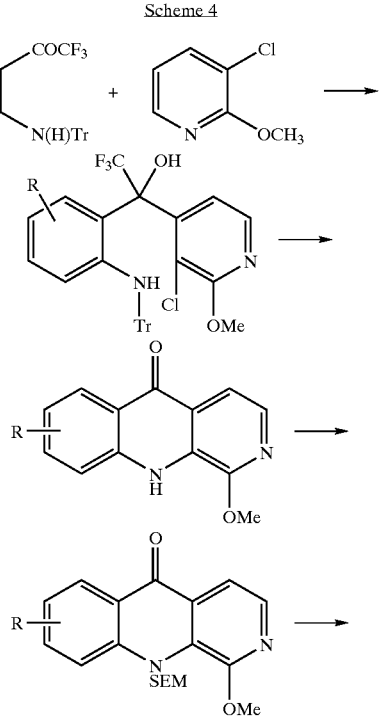

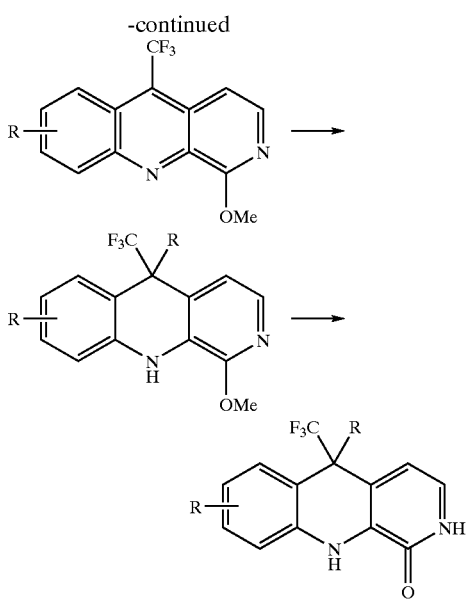

Scheme 4 describes a method of converting the protected aniline to the tricyclic structure. Metallation of the chloropyridine with LDA followed by condensation with the trifluoromethylketone gave the tertiary alcohol. Cyclization to the azaacridone was accomplished by heating in DMF with K2CO3 for base. After protection with SEM-Cl, the acridone was condensed with CF3TMS and Bu4NF to give the fully aromatic tricycle. Addition of nucleophiles such as cyanide and organometallics generated the quaternary addition products. Conversion of the methoxypyridine to the pyridone products was accomplished by heating with HCl or HBr.

While the above schemes describe methods of preparing the benzo analogs (i.e. wherein W, X, Y, and Z are all carbon), they can be modified by one skilled in the art to prepare the heterocyclic varieties wherein W, X, Y, or Z are equal to nitrogen.

SCHEME 5

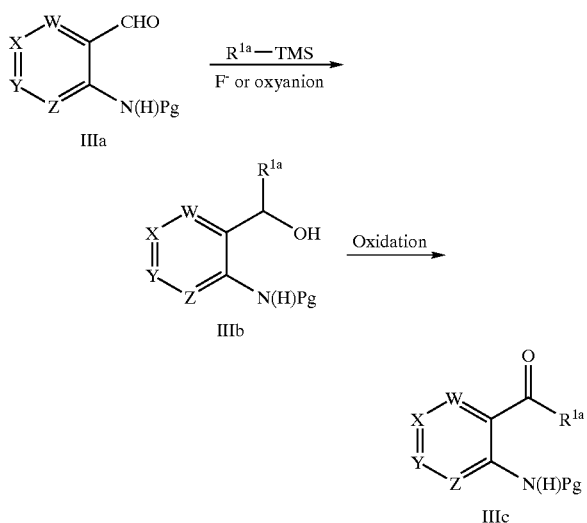

Scheme 5 illustrates specific steps for forming the aminoketone IIIc. Intermediate IIIb ($R^{1a}$ is selected from $CF_3$, $CF_3CF_2$, and $CF_3CF_2CF_2$) is useful for making some of the presently claimed compounds. Pg is an amine protecting group as defined previously, preferably trityl (triphenylmethyl). The protected or unprotected aminobenzaldehyde, preferably protected, is treated with a perfluoroalkyl trimethylsilane, preferably trifluoromethyl trimethylsilane, followed by fluoride anion, preferably tetrabutylammonium fluoride. In the same fashion, $CF_3CF_2TMS$, $CF_3CF_2CF_2TMS$ can also be used to prepare the appropriately substituted ketones. Other sources of fluoride anion such as sodium fluoride, potassium fluoride, lithium fluoride, cesium fluoride as well as oxyanionic species such as potassium tert-butoxide, sodium methoxide, sodium ethoxide and sodium trimethylsilanolate can also be used. Aprotic solvents such as DMF and THF can be used, preferably THF. The amount of perfluoroalkyl trimethylsilane used can be from about 1 to about 3 equivalents with an equivalent amount of fluoride anion or oxyanionic species. The reaction can be typically carried out at temperatures between about −20° C. to about 50° C., preferably about −10 to about 10° C., more preferably about 0° C.

Conversion of IIIb to IIIc can be achieved by using an oxidizing agent well known to one of skill in the art such as $MnO_2$, PDC, PCC, $K_2Cr_2O_7$, $CrO_3$, $KMnO_4$, $BaMNO_4$, $Pb(OAc)_4$, and $RuO_4$. A preferred oxidant is $MnO_2$. Such conversion can be performed in an aprotic solvent like THF, DMF, dichloromethane dichloroethane, or tetrachloroethane, preferably dichloromethane.

SCHEME 6

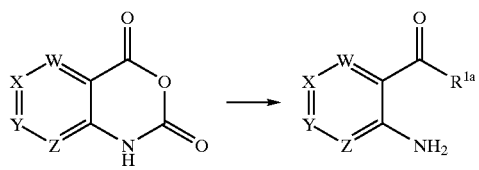

In addition to the methods of obtaining keto-anilines described in Schemes 1 and 2, nucleophilic opening of isatoic anhydrides can also be used as shown in Scheme 6. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

It is preferred that the stoichiometry of the isatoic anhydride reagent to nucleophile is about 1.0 to 2.1 molar equivalents. The use of 1.0 eq. or more (e.g., 1.1, 1.2, 1.3, 1.4, 1.5, 1.6, 1.7, 1.8, 1.9, or 2.0) of anion (or anion precursor) is preferred to force the conversion and improve the isolated yield. Preferably, the temperature used is from −20 to +35° C., with temperatures below 0° C. being more preferred and −20° C. being even more preferred. Reactions are run to about completion with time dependent upon inter alia nucleophile, solvent, and temperature. Preferably this nucleophilic addition is run in THF, but any aprotic solvent would be suitable. Reaction with the active nucleophilic anion is the only criterion for exclusion of a solvent.

Patent Publications WO98/14436, WO98/45276, and WO01/29037 describe other methods of preparing the appropriately substituted anilines and are hereby incorporated by reference.

The keto-anilines can alsobe converted to the tricyclic compounds using procedures described in the examples.

One enantiomer of a compound of Formula I may display superior activity compared with the other. Thus, both of the following stereochemistries are considered to be a part of the present invention.

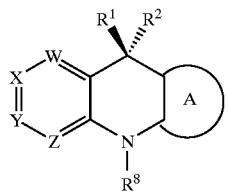 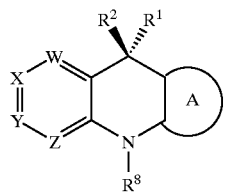

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605.

Other features of the invention will become apparent in the course of the following descriptions of exemplary embodiments that are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "ACN" for acetic anhydride, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "TBAF" for tetrabutylammonium fluoride, "TBS-Cl" for t-butyldimethylsilyl chloride, and "TEA" for triethylamine.

All reactions were run under a nitrogen atmosphere at room temperature and most were not optimized. The reactions were followed by TLC. Reactions run over night were done so for adequate time. Reagents were used as received. Dimethylformamide, tetrahydrofuran and acetonitrile were dried over molecular sieves. All other solvents were reagent grade. Ethanol and methanol were absolute and water was deionized. Melting points were determined in open capillary tubes on a Mel-Temp apparatus and are uncorrected. Column chromatographies were done on flash silica gel. Exceptions to any of the conditions above are noted in the text. Ciral HPLC separations were done using chiral columns which gave the enantiomers in >99% EE.

The following methods are illustrated in the synthethic schemes that follow the methods. While the schemes are described for specific compounds, the same methods were employed to synthesize the other compounds that are listed in the table of examples.

Example 1

Compound VIII, wherein R=(6-methylpyrid-2-yl) methyl

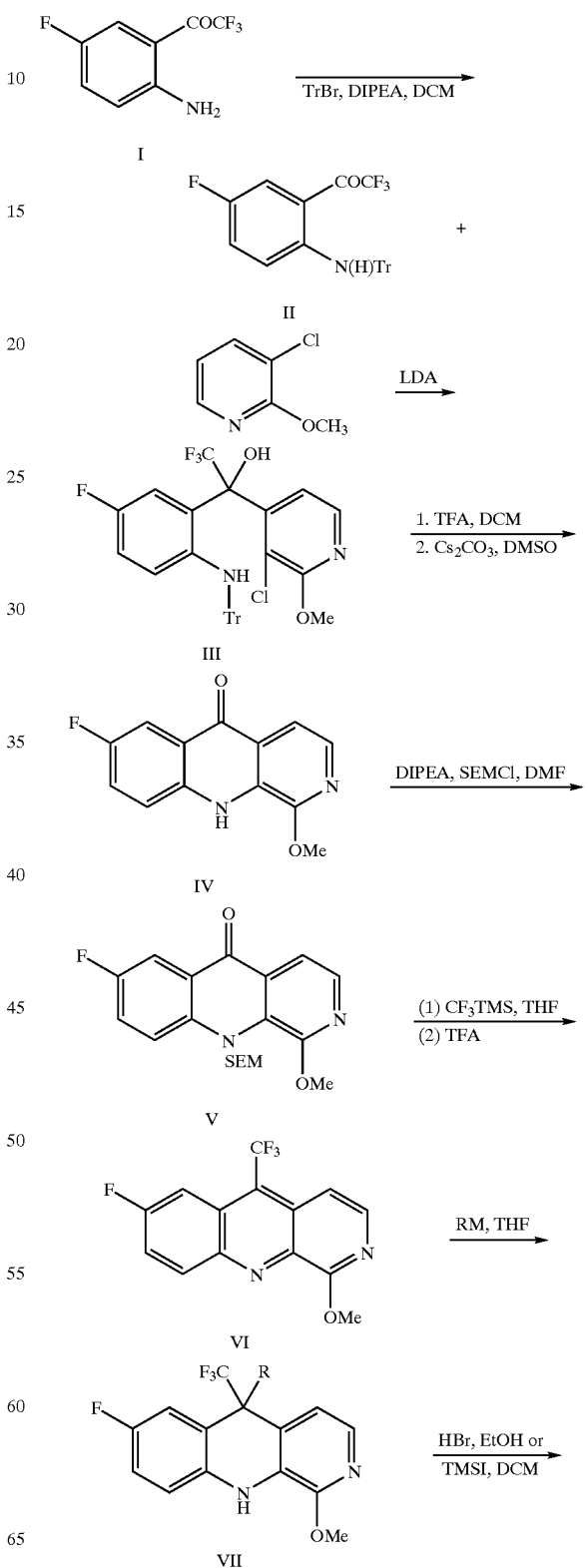

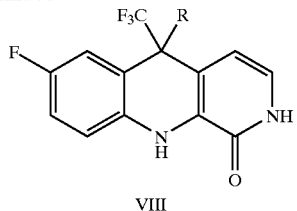

VIII

Step A: Preparation of Compound II.

To a solution of amino ketone I (19.4 g, 281 mmol) in dichloromethane (400 mL) at room temperature was added DIPEA (49 mL, 843 mmol) followed by trityl bromide (30.3 g, 281 mmol) and the resulting reaction mixture was allowed to stir at room temperature for 15 minutes. The reaction mixture was poured onto 3N HCl and extracted with dichloromethane (4×200 mL). The combined dichloromethane extracts were dried over anhydrous $Na_2SO_4$ and concentrated in vacuo to provide 85 g of compound II, (126 g theoretical, 67%). $^1H$ NMR (300 MHz, $CDCl_3$) δ 10.29(br s, 1H), 7.43(d, 1H, J=6 Hz), 7.3(m, 15H), 6.78(m, 1H), 6.29(m, 1H). $^{19}F$ NMR (282 MHz, $CDCl_3$) δ −69.34(s, 3F), −128.28(s, 1F). Anal. ($C_{27}H_{19}NOF_4$) C, H, N.

Step B: Preparation of Compound III.

To a solution of 2-methoxy-3-chloropyridine (11.9 g, 83.1 mmol) in THF (600 mL) at −78° C. was added a 2M solution of LDA in THF (45.6 mL, 91.4 mmol) followed by compound II (37.35 g, 83.1 mmol), and the resulting reaction mixture was allowed to stir while warming to room temperature for 30 minutes. The reaction mixture was poured onto saturated ammonium chloride and extracted with ethyl acetate (3×200 mL). The combined extracts were dried over anhydrous $MgSO_4$ and concentrated in vacuo. Chromatography ($SiO_2$, 10% EtOAc-hexanes eluant) provided 25.9 g of compound III (74.1 g theoretical, 35%). $^1H$ NMR (300 MHz, $CDCl_3$) δ 7.91(d, 1H, J=6 Hz), 7.4–6.9(m, 17H), 6.51(m, 1H), 6.08(m, 1H), 4.01 (s, 3H). $^{16}F$ NMR (282 MHz, $CDCl_3$) δ −76.81(br s, 3F), −128.36(s, 1F). Anal. ($C_{33}H_{25}N_2O_2ClF_4$) C, H, N.

Step C: Preparation of Compound IV.

To a solution of compound III (25.89 g, 43.65 mmol) in dichloromethane (225 mL) at room temperature was added TFA (225 mL) and the resulting reaction mixture was allowed to stir at room temperature for one hour. The reaction mixture was poured onto saturated sodium bicarbonate and extracted with ethyl acetate (3×200 mL). The combined ethyl acetate extracts were dried over anhydrous $NaSO_4$ and concentrated in vacuo. Chromatography ($SiO_2$, 20% EtOAc-hexanes eluant) provided 14.28 g of the deprotected compound (15.31 g theoretical, 93%). $^1H$ NMR (300 MHz, DMSO-$d_6$) δ 8.10(d, 1H, J=6 Hz), 7.27(m, 1H), 6.9(m, 1H), 6.75(m, 1H), 6.65(m, 1H), 3.99(s, 3H). $^{19}F$ NMR (282 MHz, DMSO-$d_6$) δ −74.95(br s, 3F), −122.01(s, 1F). Anal. ($C_{14}H_{11}N_2O_2ClF_4$) C, H, N.

To a solution of the above deprotected compound (2.0 g, 5.70 mmol) in DMSO (40 mL) at room temperature was added cesium carbonate (9.29 g, 28.5 mmol) and the resulting reaction mixture was allowed to stir at 120° C. for 8 hours. The reaction mixture was poured onto 1N HCl and the solids were filtered off. The residue was washed sequentially with water and ethanol and ether and dried in vacuo to provide 1.12 g of compound IV (1.39 g theoretical, 81%). $^1H$ NMR (300 MHz, $CDCl_3$) δ 11.88 (br s, 1H), 8.10(m, 1H), 7.95(m, 1H), 7.85(m, 1H), 7.75(m, 1H), 7.60(m, 1H). $^{19}F$ NMR (282 MHz, $CDCl_3$) δ −119.46(s, 3F), −145.79(s, 1F). Anal. ($C_{13}H_9N_2O_2F$) C, H, N.

Step D: Preparation of Compound V.

To a solution of compound IV (2.31 g, 9.45 mmol) in DMF (40 mL) at room temperature was added DIPEA (8.24 mL, 47.3 mmol) followed by SEMCl (3.35 mL, 18.9 mmol), and the resulting reaction mixture was allowed to stir at room temperature overnight. The reaction mixture was poured onto water and extracted with ethyl acetate (2×50 mL). The combined ethyl acetate extracts were dried over anhydrous $NaSO_4$ and concentrated in vacuo. Chromatography ($SiO_2$, 20% acetone-hexanes eluant) provided 5.04 g of compound V (5.21 g theoretical, 96%). $^1H$ NMR (300 MHz, $CDCl_3$) δ 8.1–8.0(m, 2H), 7.9–7.8(m, 2H), 7.5–7.4(m, 1H), 5.83(s, 2H), 4.15(s, 3H), 3.6 m, 2H), (1.0(m, 2H), 0.01(s, 9H). $^{19}F$ NMR (282 MHz, $CDCl_3$) δ −119.02(s, 1F). Anal. ($C_{19}H_{23}N_2O_3SiF_4$) C, H, N.

Step E: Preparation of Compound VI.

To a solution of compound V (5.04 g, 13.46 mmol), in THF (60 mL) at room temperature was added $CF_3TMS$ (6.0 mL, 40.4 mmol) followed by TBAF (4.04 mL, 4.04 mmol) and the resulting reaction mixture was allowed to stir at 0° C. for 30 minutes. The reaction mixture was poured onto water and extracted with ethyl acetate (2×100 mL). The combined ethyl acetate extracts were dried over anhydrous $MgSO_4$ and concentrated in vacuo to give a brown oil which was used in the next step without further purification.

A solution of the above brown oil (crude product, 13.46 mmol) in TFA (70 mL) was allowed to stir at room temperature for 30 minutes. The reaction mixture was concentrated in vacuo. The residue was taken up in THF (70 mL), methanol (70 mL), and saturated sodium bicarbonate (70 mL), and the resulting reaction mixture was allowed to stir at room temperature for 5 minutes. The reaction mixture was poured onto water and extracted with ethyl acetate (2×100 mL). The combined ethyl acetate extracts were dried over $MgSO_4$ and concentrated in vacuo. Chromatography ($SiO_2$, 20–30% EtOAc-hexanes eluant) provided 3.52 g of compound VI (3.99 g theoretical, 93%). $^1H$ NMR (300 MHz, $CDCl_3$) δ 8.6–8.5(m, 1H), 8.1–8.0(m, 2H), 7.8–7.6(m, 1H), 4.32(s, 3H). $^{19}F$ NMR (282 MHz, $CDCl_3$) δ −52.42(s, 3F), −104.57(s, 1F). Anal. ($C_{14}H_8N_2OF_4$) C, H, N.

Step F: Preparation of Compound VII (R=(6-methylpyrid-2-yl)methyl).

To a solution of lutidine (275 μl, 2.36 mmol) in THF (3 mL) at −78° C. was added a 2M solution of LDA in THF (1.18 mL, 2.36 mmol) and the resulting reaction mixture was allowed to stir at −78° C. for 15 minutes. Thereafter, compound VI (175 mg, 0.59 mmol) was added and the resulting reaction mixture was allowed to stir at −78° C. for 30 minutes. The reaction mixture was poured onto saturated $NH_4Cl$ and thereafter partitioned between ethyl acetate and water. The combined ethyl acetate extracts were dried over anhydrous $MgSO_4$ and concentrated in vacuo. Chromatography ($SiO_2$, 50% EtOAc-hexanes eluant) provided 30 mg of compound VIIa (238 g theoretical, 13%). $^1H$ NMR (300 MHz, $CDCl_3$) δ 7.63(d, 1H, J=6 Hz), 7.3(m, 1H), 7.1–7.0(m, 2H), 6.95(s, 1H), 6.8–6.6(m, 2H), 6.4(d, 1H, J=8 Hz), 4.03(s, 3H), 2.38 (s, 3H). $^{19}F$ NMR (282 MHz, $CDCl_3$) δ −76.02(s, 3F), −122.84(s, 1F). Anal. ($C_{21}H_{17}N_3OF_4$) C, H, N.

Step G: Preparation of Compound of Formula VIII (R=(6-methylpyrid-2-yl)methyl).

To a solution of VII (R=(6-methylpyrid-2-yl)methyl) (30 mg, 0.074 mmol) in ethanol (1 mL) was added a 48% aqueous solution of HBr (1 mL) and the resulting reaction mixture was allowed to stir at reflux for 1.5 hours. The reaction mixture is poured onto saturated $NaHCO_3$ and extracted with ethyl acetate (3×25 mL). The combined ethyl acetate extracts were dried over anhydrous MgSO$_4$ and concentrated in vacuo. Chromatography (SiO$_2$, EtOAc eluant) provided 23 mg of compound VIII (R=(6-methylpyrid-2-yl)methyl)(29 mg theoretical, 79%). $^1$H NMR (300 MHz, acetone-d$_6$) δ 8.15 (br s, 1H), 7.4(m, 1H), 7.35(m, 2H), 7.0–6.85(m, 2H), 6.8–6.75(m, 1H), 6.5–6.6(m, 1H), 4.03(m, 2H), 2.23(s, 3H). $^{19}$F NMR (282 MHz, acetone-d$_6$) δ −76.08(s, 3F), −124.98(s, 1F). Anal. (C$_{20}$H$_{15}$N$_3$O$_1$F$_4$) C, H, N.

Example 2

Compound VIII, wherein R=cyclopropylacetylenyl

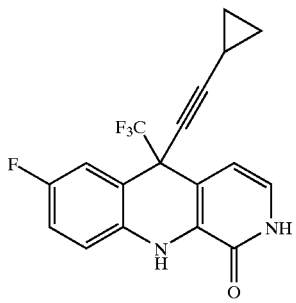

Step F: Preparation of Compound VII (R=cyclopropylacetylenyl).

To a solution of cyclopropylacetylene (167 μl, 1.52 mmol) in THF (2 mL) at 0° C. was added a 1.6M solution of nBuLi in THF (0.85 mL, 1.36 mmol) and the resulting reaction mixture was allowed to stir at 0° C. for 20 minutes. Thereafter, the reaction mixture was cooled to −78° C. and compound VI (100 mg, 0.34 mmol) was added and the resulting reaction mixture was warmed to 0° C. and allowed to stir with warming to room temperature over a period of several hours. The reaction mixture was quenched with saturated NH$_4$Cl and poured onto water and extracted with ethyl acetate (2×25 mL). The combined ethyl acetate extracts were dried over anhydrous MgSO$_4$ and dried in vacuo. Chromatography (SiO$_2$, 50% EtOAc-hexanes eluant) provided 30 mg of the title compound (238 g theoretical, 13%). $^1$H NMR (300 MHz, CDCl$_3$) δ 7.8(d, 1H, J=6 Hz), 7.5(m, 1H), 7.25(m, 1H), 7.1(m, 1H), 6.85–6.8(m, 1H), 6.75(br s, 1H), 4.06(s, 3H), 1.48(s, 3H), 1.4(m, 1H), 0.9(m, 2H), 0.8(m, 2H). $^{19}$F NMR (282 MHz, CDCl$_3$) δ −77.30(s, 3F), −122.50(s, 1F). High resolution mass spec: calculated for C$_{19}$H$_{15}$N$_2$OF$_4$ (M+H)$^+$: 363.1121, found 363.1128.

Step G: Preparation of Compound of Formula VIII (R=cyclopropylacetylenyl).

To a solution of compound VII (R=cyclopropylacetylenyl)(18 mg, 0.05 mmol) in dichloromethane (1 mL) at room temperature was added TMSI (100 μl of a 1M solution in dichloromethane, 0.01 mmol) and the resulting reaction mixture was allowed to stir at room temperature overnight. The reaction mixture was poured onto water and extracted with ethyl acetate (2×25 mL). The combined ethyl acetate extracts were dried over anhydrous MgSO$_4$ and concentrated in vacuo. Chromatography (SiO$_2$, 20% EtOAc-hexanes eluant) provided 3 mg of the title compound (17 mg theoretical, 18%). $^1$H NMR (300 MHz, CDCl$_3$) δ 7.5(m, 1H), 7.35(br s, 1H), 7.05–7.0(m, 1H), 6.95–6.85 (m, 2H), 6.85–6.8(m, 1H), 4.06(s, 3H), 1.57(s, 3H), 1.4 (m, 1H), 0.9(m, 2H), 0.8(m, 2H). $^{19}$F NMR (282 MHz, CDCl$_3$) δ −77.26(s, 3F), −121.64(s, 1F). High resolution mass spec: calculated for C$_{18}$H$_{13}$N$_2$OF$_4$ (M+H)$^+$: 349.0964, found 349.0939.

Example 3

Compound VIII, wherein R=N-propyl

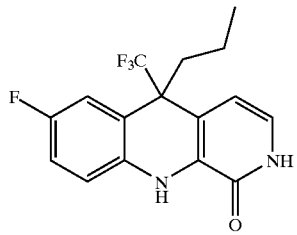

Step F: Preparation of Compound of Formula VII (R=n-propyl).

To a solution of VI (175 mg, 0.59 mmol) in THF (2 mL) at −78° C. was added a 2M solution of n-propyl magnesium chloride in ether (1.48 mL, 2.95 mmol) and the resulting reaction mixture was allowed to stir at −78° C. for 15 minutes. The reaction mixture was quenched with saturated NH$_4$Cl and poured onto water and extracted with ethyl acetate (2×50 mL). Chromatography (SiO$_2$, 20% EtOAc-hexanes eluant) provided 144 mg of compound VIIc (201 g theoretical, 72%). $^1$H NMR (300 MHz, CDCl$_3$) δ 7.8(d, 1H, J=6 Hz), 7.5(m, 1H), 7.25(m, 1H), 7.1(m, 1H), 6.85–6.8(m, 1H), 6.75(br s, 1H), 4.06(s, 3H), 1.48(s, 3H), 1.4(m, 1H), 0.9(m, 2H), 0.8(m, 2H). $^{19}$F NMR (282 MHz, CDCl$_3$) δ −76.15(s, 3F), −122.88(s, 1F). High resolution mass spec: calculated for C$_{17}$H$_{17}$N$_2$OF$_4$ (M+H)$^+$: 341.1277, found 341.1282.

Step G: Preparation of Compound of Formula VIII (R=n-propyl).

To a solution of VII (R=n-propyl)(144 mg, 0.42 mmol) in ethanol (2 mL) at room temperature was added a 48% aqueous solution of HBr (2 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 50% EtOAc-hexanes eluant) provided 84 mg of the title compound (137 mg theoretical, 61%). $^1$H NMR (300 MHz, acetone-d$_6$) δ 11.56 (br s, 1H), 8.74(br s, 1H), 7.44(m, 1H), 7.2(m, 1H), 7.05–6.95(m, 2H), 6.42(m, 1H), 6.5–6.6(m, 1H), 4.03(m, 2H), 2.4(m, 2H), 1.05(m, 3H). $^{19}$F NMR (282 MHz, acetone-d$_6$) δ −76.48(s, 3F), −124.44(s, 1F). Anal. (C$_{16}$H$_{14}$N$_2$OF$_4$) C, H, N.

Example 4

Compound VIII, wherein R=N-butyl

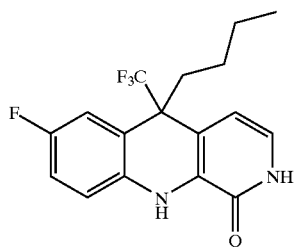

Step F: Preparation of Compound of Formula VII (R=n-butyl)

To a solution of VI (500 mg, 1.69 mmol) in THF (8 mL) at −78° C. was added a 2M solution of n-butyl magnesium chloride in ether (4.22 mL, 8.44 mmol) and the resulting reaction mixture was allowed to stir at −78° C. for 15 minutes. The reaction mixture was quenched with saturated NH$_4$Cl and poured onto water and extracted with ethyl acetate (2×50 mL). Chromatography (SiO$_2$, 10% EtOAc-hexanes eluant) provided 337 mg of compound VII (R=n-butyl)(599 mg theoretical, 56%). $^1$H NMR (300 MHz, CDCl$_3$) δ 7.70(d, 1H, J=6 Hz), 7.1(m, 1H), 7.0–6.95(m, 1H), 6.85(m, 1H), 6.8(m, 1H), 6.7(br s, 1H), 4.06(s, 3H), 2.4(m, 2H), 1.35(m, 2H), 1.1 (m, 2H), 0.8(t, 3H, J=7 Hz)), 0.8(m, 2H). $^{19}$F NMR (282 MHz, CDCl$_3$) δ −76.12(s, 3F), −122.86 (s, 1F). Anal. (C$_{18}$H$_{18}$N$_2$OF$_4$) C, H, N.

Step G: Preparation of Compound of Formula VIII (R=n-butyl).

To a solution of VII (R=n-butyl)(64 mg, 0.18 mmol) in ethanol (2 mL) at room temperature was added a 48% aqueous solution of HBr (2 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 50% EtOAc-hexanes eluant) provided 36 mg of the title compound (61 mg theoretical, 59%). $^1$H NMR (300 MHz, CDCl$_3$) δ 12.5(br s, 1H), 7.55(br s, 1H), 7.1(m, 1H), 7.0–6.8(m, 3H), 6.35(m, 1H), 2.3(m, 2H), 1.35 (m, 2H), 1.05(m, 2H), 0.8(t, 3H, J=7 Hz). $^{19}$F NMR (282 MHz, CDCl$_3$) δ −75.84(s, 3F), −122.14 (s, 1F). Anal. (C$_{17}$H$_{16}$N$_2$OF$_4$) C, H, N.

Example 5

Compound VIII, wherein R=4-fluorophenylmethyl

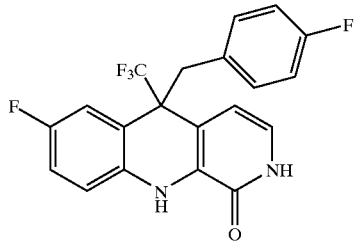

Step F: Preparation of Compound of Formula VII(R=4-fluorophenylmethyl).

To a solution of VI (196 mg, 0.66 mmol) in THF (2 mL) at −78° C. was added a 0.25M solution of p-fluorophenylmagnesium chloride in ether (13.2 mL, 3.3 mmol) and the resulting reaction mixture was allowed to stir at −78° C. for 45 minutes. The reaction mixture was quenched with saturated NH$_4$Cl and poured onto water and extracted with ethyl acetate (2×50 mL). Chromatography (SiO$_2$, 20% EtOAc-hexanes eluant) provided 153 mg of compound VII (R=4-fluorophenylmethyl)(268 mg theoretical, 57%). $^1$H NMR (300 MHz, CDCl$_3$) δ 7.73(d, 1H, J=6 Hz), 7.3(m, 1H), 7.1(m, 1H), 6.95(m, 1H), 6.8–6.6 (m, 5H), 6.55(br s, 1H), 3.99(s, 3H), 3.7(m, 2H). $^{19}$F NMR (282 MHz, CDCl$_3$) δ −74.25(s, 3F), −116.27(s, 1F), −122.53 (s, 1F). Anal. (C$_{21}$H$_{15}$N$_2$OF$_5$) C, H, N.

Step G: Preparation of Compound of Formula VIII(R=4-fluorophenylmethyl).

To a solution of VII (R=4-fluorophenylmethyl)(153 mg, 0.38 mmol) in ethanol (4 mL) at room temperature was added a 48% aqueous solution of HBr (4 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 50% EtOAc-hexanes eluant) provided 89 mg of the title compound (149 mg theoretical, 60%). $^1$H NMR (300 MHz, CDCl$_3$) δ 12.0(br s, 1H), 7.3(m, 1H), 7.0(m, 1H), 6.9(m, 1H), 6.85–6.7(m, 5H), 6.55(m, 1H). $^{19}$F NMR (282 MHz, CDCl$_3$) δ −73.89(s, 3F), −116.01(s, 1F), −121.68(s, 1F). Anal. (C$_{20}$H$_{13}$N$_2$OF$_5$) C, H, N.

Example 6

Compound VIII, wherein R=2-pyridylmethyl

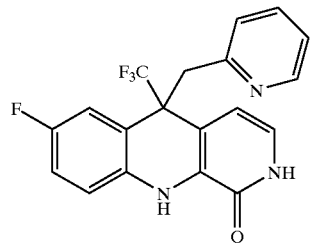

Step F: Preparation of Compound of Formula VII (R=2-pyridylmethyl).

To a solution of 2-picoline (134 µl, 1.36 mmol) in THF (2 mL) at −78° C. was added a 2M solution of LDA in THF (0.76 mL, 1.52 mmol) and the resulting reaction mixture was allowed to stir at −78° C. for 15 minutes. Thereafter, compound VI (100 mg, 0.34 mmol) was added and the resulting reaction mixture was allowed to stir at −78° C. for 30 minutes. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, 50% EtOAc-hexanes eluant) provided 111 mg of compound VII (R=2-pyridylmethyl)(132 mg theoretical, 84%). $^1$H NMR (300 MHz, CDCl$_3$) δ 8.3(d, 1H, J=5 Hz), 7.64(d, 1H, J=6 Hz), 7.3(m, 2H), 7.1(m, 1H), 6.95(m, 1H), 6.8–6.6(m, 2H), 4.1(m, 2H), 4.02(s, 3H). $^{19}$F NMR (282 MHz, CDCl$_3$) δ −75.99(s, 3F), −122.57(s, 1F). Anal. (C$_{20}$H$_{15}$N$_3$OF$_4$) C, H, N.

Step G: Preparation of Compound of Formula VIII (R=2-pyridylmethyl).

To a solution of VII (R=2-pyridylmethyl)(111 mg, 0.28 mmol) in ethanol (2 mL) was added a 48% aqueous solution of HBr (2 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, EtOAc eluant) provided 77 mg of the title compound (105 mg theoretical, 73%). $^1$H NMR (300 MHz, DMSO-d$_6$) δ 11.7(br s, 1H), 9.0 (br s, 1H), 8.3(d, 1H, J=4 Hz), 7.5(m, 1H), 7.45(m, 1H), 7.25(m, 1H), 7.05–6.95(m, 3H), 6.8(d, 1H, J=7 Hz), 6.45(d, 1H, J=7 Hz), 4.0(m, 2H). $^{19}$F NMR (282 MHz, DMSO-d$_6$) δ −74.98(s, 3F), −123.69(s, 1F). Anal. (C$_{19}$H$_{13}$N$_3$OF$_4$) C, H, N.

Example 7

Compound VIII, wherein R=i-propyl

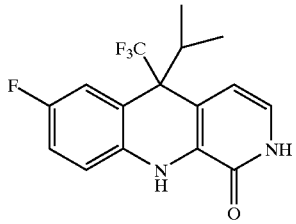

Step F: Preparation of Compound of Formula VII(R=i-propyl).

To a solution of VI (175 mg, 0.59 mmol) in THF (2 mL) at −78° C. was added a 2M solution of isopropyl magnesium chloride in ether (1.48 mL, 2.95 mmol) and the resulting reaction mixture was allowed to stir at −78° C. for 15 minutes. The reaction mixture was quenched with saturated NH$_4$Cl and poured onto water and extracted with ethyl acetate (2×50 mL). The combined ethyl acetate extracts were dried over anhydrous MgSO$_4$ and concentrated in vacuo. Chromatography (SiO$_2$, 20% EtOAc-hexanes eluant) provided 144 mg of compound VII (R=i-propyl)(201 mg theoretical, 72%). $^1$H NMR (300 MHz, CDCl$_3$) δ 7.6(d, 1H, J=6 Hz), 7.3(m, 1H), 7.05(m, 1H), 6.95(m, 1H), 6.65(m, 1H), 4.04(s, 3H), 2.6(m, 1H), 1.05(m, 6H). $^{19}$F NMR (282 MHz, CDCl$_3$) δ −64.80(s, 3F), −122.85(s, 1F). High resolution mass spec: calculated for C$_{17}$H$_{17}$N$_2$OF$_4$ (M+H)$^+$: 341.1277, found 341.1276.

Step G: Preparation of Compound of Formula VIII(R=i-propyl).

To a solution of VII (R=i-propyl)(144 mg, 0.42 mmol) in ethanol (2 mL) at room temperature was added a 48% aqueous solution of HBr (2 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 50% EtOAc-hexanes eluant) provided 63 mg of the title compound (137 mg theoretical, 46%). $^1$H NMR (300 MHz, acetone-d$_6$) δ 11.0 (br s, 1H), 8.3 (br s, 1H), 7.4–7.2(m, 2H), 7.1(m, 1H), 6.95(d, 1H, J=7 Hz), 6.4(m, 1H), 2.7(m, 1H), 1.0(m, 6H). $^{19}$F NMR (282 MHz, acetone-d$_6$) δ −65.46(s, 3F), −124.43 (s, 1F). Anal. (C$_{16}$H$_{14}$N$_2$OF$_4$) C, H, N.

Example 8

Compound VIII, wherein R=3-pyridylmethyl

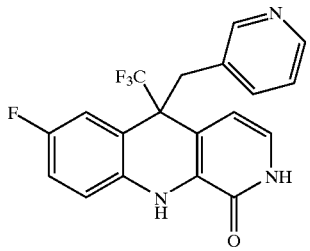

Step F: Preparation of Compound of Formula VII (3-pyridylmethyl).

To a solution of 3-picoline (230 μl, 2.36 mmol) in THF (3 mL) at −78° C. was added a 2M solution of LDA in THF (1.33 mL, 2.66 mmol) and the resulting reaction mixture was allowed to stir at −78° C. for 15 minutes. Thereafter, compound VI (175 mg, 0.59 mmol) was added and the resulting reaction mixture was allowed to stir at −78° C. for 30 minutes. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, 50% EtOAc-hexanes eluant) provided 8 mg of compound VII (3-pyridylmethyl)(230 mg theoretical, 3%). $^1$H NMR (300 MHz, CDCl$_3$) δ 8.25(d, 1H, J=6 Hz), 8.1(m, 1H0, 7.69(d, 1H, J=6 Hz), 7.3(m, 1H), 7.1(m, 2H), 6.9(m, 2H), 6.7(m, 1H), 6.55(br s, 1H), 4.01(s, 3H), 3.75(m, 2H). $^{19}$F NMR (282 MHz, CDCl$_3$) δ −74.42(s, 3F), −122.07(s, 1F). High resolution mass spec: calculated for C$_{20}$H$_{16}$N$_3$OF$_4$ (M+H)$^+$: 390.1230, found 390.1248.

Step G: Preparation of Compound of Formula VIII (3-pyridylmethyl).

To a solution of VII (3-pyridylmethyl)(8 mg, 0.02 mmol) in ethanol (1 mL) was added a 48% aqueous solution of HBr (1 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 5% MeOH-dichloromethane eluant) provided 4 mg of the title compound (7.5 mg theoretical, 53%). $^1$H NMR (300 MHz, acetone-d$_6$) δ 11.0(br s, 1H), 8.4 (br s, 1H), 8.2(m, 2H), 7.6(m, 1H), 7.4–7.2(m, 2H), 7.15–7.0(m, 3H), 6.65(m, 1H), 3.95(m, 2H). $^{19}$F NMR (282 MHz, acetone-d$_6$) δ −74.81(s, 3F), −124.05(s, 1F). High resolution mass spec: calculated for C$_{19}$H$_{14}$N$_3$OF$_4$ (M+H)$^+$: 376.1073, found 376.1060.

Example 9

Compound VIII, wherein R=4-pyridylmethyl

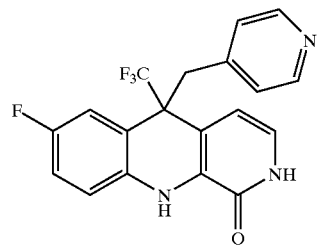

Step F: Preparation of Compound of Formula VII (R=4-pyridylmethyl).

To a solution of 4-picoline (230 μl, 2.36 mmol) in THF (3 mL) at −78° C. was added a 2M solution of LDA in THF (1.33 mL, 2.66 mmol) and the resulting reaction mixture was allowed to stir at −78° C. for 15 minutes. Thereafter, compound VI (175 mg, 0.59 mmol) was added and the resulting reaction mixture was allowed to stir at −78° C. for 30 minutes. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, 50% EtOAc-hexanes eluant) provided 116 mg of compound VII (R=4-pyridylmethyl)(230 g theoretical, 50%). $^1$H NMR (300 MHz, CDCl$_3$) δ 8.25(m, 1H), 7.68(d, 1H, J=6 Hz), 7.25(m, 1H), 7.05–6.95(m, 2H), 6.8–6.65(m, 3H), 4.0(s, 3H), 3.75(m, 2H). $^{19}$F NMR (282 MHz, CDCl$_3$) δ −74.83(s, 3F), −122.13(s, 1F). Anal. (C$_{20}$H$_{15}$N$_3$OF$_4$) C, H, N.

Step G: Preparation of Compound of Formula VIII (R=4-pyridylmethyl).

To a solution of VII (R=4-pyridylmethyl)(116 mg, 0.30 mmol) in ethanol (2 mL) was added a 48% aqueous solution of HBr (2 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, EtOAc eluant) provided 93 mg of the title compound (113 mg theoretical, 82%). $^1$H NMR (300 MHz, acetone-d$_6$) δ 10.65(br s, 1H), 8.2 (m, 3H), 7.5(m, 1H), 7.3 (m, 1H), 7.1–6.9(m, 4H), 6.6(m, 1H), 3.95(m, 2H). $^{19}$F NMR (282 MHz, acetone-d$_6$) δ −75.45(s, 3F), −124.13(s, 1F). Anal. (C$_{19}$H$_{13}$N$_3$OF$_4$) C, H, N.

Example 10

Compound VIII, wherein R=3-propynyl

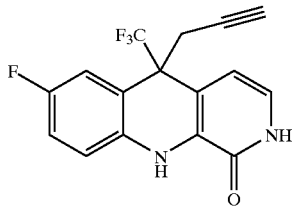

Step F: Preparation of Compound of Formula VII (R=3-propynyl).

To a solution of 1-TMS-1-propyne (300 μl, 2.02 mmol) in THF (3 mL) at −78° C. was added a 2M solution of LDA in THF (1.14 mL, 2.28 mmol) and the resulting reaction mixture was allowed to stir at −78° C. for 20 minutes. Thereafter, compound VI (150 mg, 0.51 mmol) was added and the resulting reaction mixture was allowed to stir at −78° C. 30 minutes. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, 20% EtOAc-hexanes eluant) provided 102 mg of compound VII (R=3-propynyl)(207 mg theoretical, 49%). $^1$H NMR (300 MHz, CDCl$_3$) δ 7.72(d, 1H, J=6 Hz), 7.2(m, 1H), 7.0(m, 1H), 6.9(m, 1H), 6.8(m, 1H), 6.75(br s, 1H), 4.07(s, 3H), 3.35(m, 2H). $^{19}$F NMR (282 MHz, CDCl$_3$) δ −75.68(s, 3F), −123.05(s, 1F). High resolution mass spec: calculated for C$_{20}$H$_{21}$N$_2$OSiF$_4$ (M+H)$^+$: 409.1359, found 409.11365.

Step G: Preparation of Compound of Formula VIII (R=3-propynyl).

To a solution of compound VII (R=3-propynyl)(102 mg, 0.25 mmol) in dichloromethane (5 mL) at room temperature was added TMSI (2 ml of a 1M solution in dichloromethane, 2 mmol) and the resulting reaction mixture was allowed to stir at room temperature for 4 hours. The reaction mixture was poured onto water and extracted with dichloromethane (2×25 mL). The combined dichloromethane extracts were dried over anhydrous MgSO$_4$ and concentrated in vacuo. Chromatography (SiO$_2$, 20% EtOAc-hexanes eluant) provided 66 mg of the trimethylsilyl protected compound (99 mg theoretical, 67%). $^1$H NMR (300 MHz, CDCl$_3$) δ 12.4(br s, 1H), 7.5(br s, 1H), 7.15(m, 1H), 7.05(m, 1H), 7.0–6.85 (m, 2H), 6.4(d, 1H, J=7 Hz), 3.3(m, 2H), 0.05(s, 9H). $^{19}$F NMR (282 MHz, CDCl$_3$) δ −75.37(s, 3F), −122.19(s, 1F). Anal. (C$_{19}$H$_{18}$N$_2$OSiF$_4$) C, H, N.

To a solution of the above trimethylsilyl protected compound (66 mg, 0.17 mmol) in methanol (1 mL) at room temperature was added potassium carbonate (117 mg, 0.85 mmol) and the resulting reaction mixture was allowed to stir for one hour. The reaction mixture was poured onto water and extracted with ethyl acetate (2×50 mL). The combined ethyl acetate extracts were dried over anhydrous MgSO$_4$ and in vacuo. Chromatography (SiO$_2$, 50% EtOAc-hexanes eluant) provided 34 mg of the title compound (55 mg theoretical, 82%). $^1$H NMR (300 MHz, CDCl$_3$) δ 12.4(br s, 1H), 7.6(br s, 1H), 7.2(m, 1H), 7.05(m, 1H), 7.0–6.9(m, 2H), 6.4(d, 1H, J=7 Hz), 3.3(m, 2H), 1.8(m, 1H). $^{19}$F NMR (282 MHz, CDCl$_3$) δ −76.19 (s, 3F), −121.68(s, 1F). Anal. (C$_{16}$H$_{10}$N$_2$OF$_4$) C, H, N.

Example 11

Compound VIII, wherein R=2-pyridylethynyl

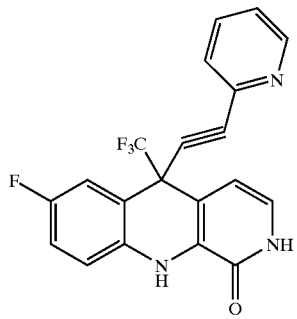

Step F: Preparation of Compound of Formula VII (R=2-pyridylethynyl).

To a solution of 2-ethynylpyridine (157 μl, 1.52 mmol) in THF (1.5 mL) at −78° C. was added a 1.6M solution of nBuLi in THF (0.85 mL, 1.36 mmol) and the resulting reaction mixture was allowed to stir at −78° C. for 15 minutes. Thereafter, compound VI (175 mg, 0.59 mmol) was added and the resulting reaction mixture was allowed to stir with warming to room temperature for 30 minutes. The reaction mixture was poured onto saturated NH$_4$Cl and thereafter partitioned between ethyl acetate and 0.1N HCl. The combined ethyl acetate extracts were dried over anhydrous MgSO$_4$ and concentrated in vacuo. Chromatography (SiO$_2$, 50% EtOAc-hexanes eluant) provided 39 mg of compound VII (R=2-pyridylethynyl)(136 mg theoretical, 29%). $^1$H NMR (300 MHz, CDCl$_3$) δ 8.65(m, 1H), 7.8–7.7 (m, 2H), 7.65–7.55(m, 2H), 7.4–7.25(m, 2H), 7.1(m, 1H), 6.9(m, 1H), 6.85(br s, 1H), 4.08(s, 3H). $^{19}$F NMR (282 MHz, CDCl$_3$) δ −76.62(s, 3F), −121.98(s, 1F). Anal. (C$_{21}$H$_{13}$N$_3$OF$_4$) C, H, N.

Step G: Preparation of Compound of Formula VIII (R=2-pyridylethynyl).

To a solution of compound VII (R=2-pyridylethynyl)(26 mg, 0.065 mmol) in dichloromethane (2.5 mL) at room temperature was added TMSI (1 ml of a 1M solution in dichloromethane, 0.01 mmol) and the resulting reaction mixture was allowed to stir at room temperature overnight. The reaction mixture was poured onto water and extracted with ethyl acetate (2×25 mL). The combined ethyl acetate extracts were dried over anhydrous MgSO$_4$ and concentrated in vacuo. Chromatography (SiO$_2$, EtOAc eluant) provided 9 mg of the title compound (25 mg theoretical, 36%). $^1$H NMR (300 MHz, acetone-d$_6$) δ 11.45(br s, 1H), 8.6 (m, 1H), 7.95(m, 1H), 7.75(m, 1H), 7.6–7.4(m, 3H), 7.25(m, 1H), 7.12(d, 1H, J=7 Hz), 6.67(d, 1H, J=7 Hz). $^{19}$F NMR (282 MHz, acetone-d$_6$) δ −77.54(s, 3F), −123.67(s, 1F). Anal. (C$_{20}$H$_{11}$N$_3$OF$_4$) C, H, N.

Example 12

Compound VIII, wherein R=2-(2-pyridyl)ethyl

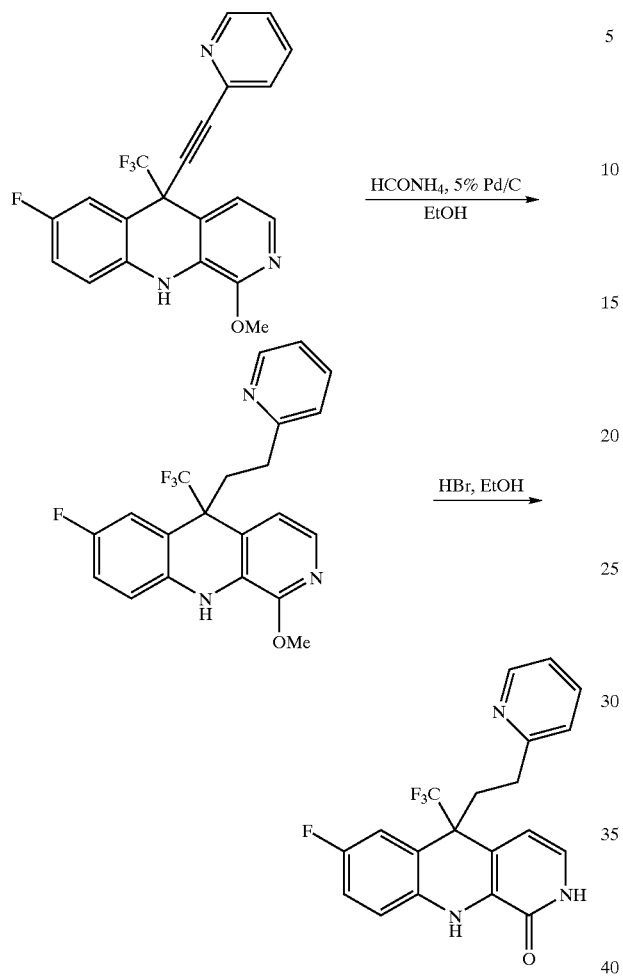

Step A: Preparation of Compound VII (R=2-pyridylethynyl).

To a solution of VII (R=2-pyridylethynyl)(20 mg, 0.05 mmol) in ethanol (1 mL) at room temperature was added ammonium formate (20 mg) and 5% Pd/C (20 mg) and the resulting reaction mixture was allowed to stir at reflux for 1.5 hours. The reaction mixture was filtered through Celite and the filtrate concentrated in vacuo. Chromatography (SiO$_2$, 40% EtOAc-hexanes eluant) provided 15 mg of compound VII (R=2-pyridylethyl)(20 mg theoretical, 75%). $^1$H NMR (300 MHz, CDCl$_3$) δ 8.5(m, 1H), 7.7(d, 1H, J=6 Hz), 7.5(m, 1H), 7.2(m, 1H), 7.15(m, 1H), 7.05–6.95(m, 3H), 6.8(m, 1H), 6.75(br s, 1H), 4.07(s, 3H), 2.8(m, 2H), 2.6(m, 2H). $^{19}$F NMR (282 MHz, CDCl$_3$) δ −75.96(s, 3F), −122.34(s, 1F). High resolution mass spec: calculated for C$_{21}$H$_{18}$N$_3$OF$_4$ (M+H)$^+$: 404.1386, found 404.1385.

Step B: Preparation of Compound VIII(R=(2-pyridyl)ethyl).

To a solution of VII (R=2-pyridylethyl)(15 mg, 0.037 mmol) in ethanol (1 mL) was added a 48% aqueous solution of HBr (1 mL) and the resulting reaction mixture was allowed to stir at reflux for 5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, EtOAc eluant) provided 5 mg of the title compound (15 mg theoretical, 36%). $^1$H NMR (300 MHz, acetone-d$_6$) δ 10.9(br s, 1H), 8.5(m, 1H), 8.3 (br s, 1H), 7.6(m, 1H), 7.4(m, 2H), 7.2–7.05(m, 3H), 7.0(d, 1H, J=7 Hz), 6.4(d, 1H, J=7 Hz), 2.95(m, 2H), 2.6(m, 2H). $^{19}$F NMR (282 MHz, acetone-d$_6$) δ −76.49(s, 3F), −124.17 (s, 1F). High resolution mass spec: calculated for C$_{20}$H$_{16}$N$_3$OF$_4$ (M+H)$^+$: 390.1221, found 390.1221.

Example 13

Compound VIIIa

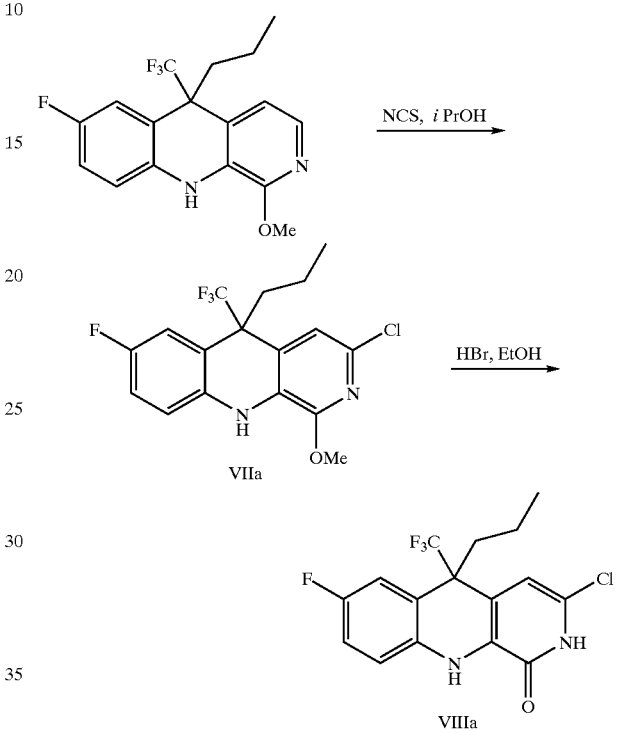

Step A: Preparation of Compound VIIa.

To a solution of compound VII (R=n-propyl)(75 mg, 0.22 mmol) in iPrOH (2 mL) at room temperature was added NCS (30 mg, 0.22 mmol) and the resulting reaction mixture was allowed to stir at reflux for 2 hours. The reaction mixture was poured onto water and extracted with ethyl acetate (2×50 mL). The combined ethyl acetate extracts were dried over anhydrous NaSO$_4$ and concentrated in vacuo. Chromatography (SiO$_2$, 10% EtOAc-hexanes eluant) provided 48 mg of compound VIIa (82 mg theoretical, 59%). $^1$H NMR (300 MHz, CDCl$_3$) δ 7.15(m, 1H), 7.0(m, 1H), 6.95(m, 1H), 6.8(m, 1H), 6.6(br s, 1H), 2.3(m, 2H), 1.1(m, 2H), 0.95(m, 3H). $^{19}$F NMR (282 MHz, CDCl$_3$) δ −76.05(s, 3F), −122.31 (s, 1F). High resolution mass spec: calculated for C$_{17}$H$_{16}$ClN$_3$OF$_4$ (M+H)$^+$: 375.0887, found 375.0883.

Step B: Preparation of Compound of Formula VIIa.

To a solution of VIIa (48 mg, 0.13 mmol) in ethanol (1 mL) was added a 48% aqueous solution of HBr (1 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 20% acetone-hexanes eluant) provided 14 mg of the title compound (47 mg theoretical, 30%). $^1$H NMR (300 MHz, acetone-d$_6$) δ 8.4(br s, 1H), 7.4(m, 1H), 7.3(m, 1H), 7.1(m, 1H), 6.6(m, 1H), 2.4(m, 2H), 1.1(m, 1H), 0.95(m, 1H). $^{19}$F NMR (282 MHz, acetone-d$_6$) δ −76.58(s, 3F), −124.11(s, 1F). Anal. (C$_{16}$H$_{13}$N$_2$OClF$_4$) C, H, N.

Example 14

Compound VIII, wherein R=3-propenyl

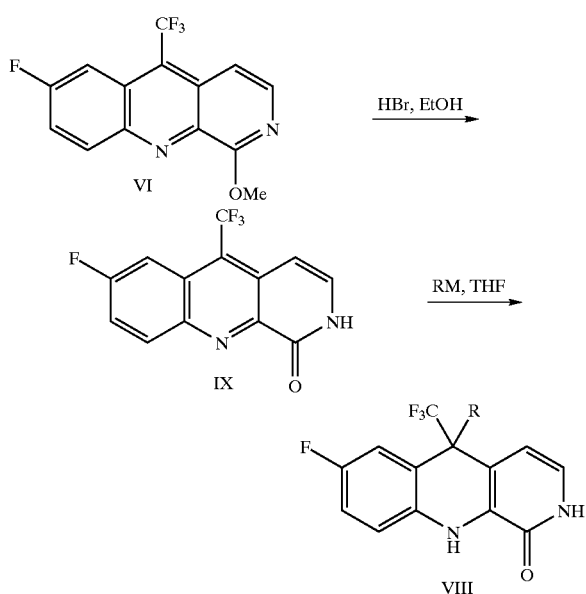

Step A: Preparation of Compound IX.

To a solution of compound VI (100 mg, 0.34 mmol) in ethanol (1 mL) at room temperature was added a 48% aqueous solution of HBr (1 mL) and the resulting reaction mixture was allowed to stir at reflux for 1.5 hours. The reaction mixture was diluted with water and filtered and the solids were washed with water and dried in vacuo to give a yellow solid. Toluene was added to the solids and dried in vacuo to azeotrope traces of water to provide 89 mg of compound IX (96 mg theoretical, 93%). $^1$H NMR (300 MHz, DMSO-d$_6$) δ 11.95(br s, 1H), 8.4(m, 1H), 7.95(m, 2H), 7.4(m, 1H), 6.8(m, 1H). $^{19}$F NMR (282 MHz, DMSO-d$_6$) δ -52.44(s, 3F), -105.16 (s, 1F). High resolution mass spec: calculated for $C_{13}H_7N_2OF_4$ (M+H)$^+$: 283.0495, found 283.0492.

Step B: Preparation of Compound of Formula VIII (R=3-propenyl).

To a solution of IX (170 mg, 0.60 mmol) in THF (3 mL) at -78° C. was added a 1M solution of allyl magnesium bromide in ether (3.6 mL, 3.6 mmol) and the resulting reaction mixture was allowed to stir at -78° C. for 15 minutes. The reaction mixture was quenched with saturated NH$_4$Cl and poured onto water and extracted with ethyl acetate (2×50 mL). The combined ethyl acetate extracts were dried over anhydrous MgSO$_4$ and concentrated in vacuo. Chromatography (SiO$_2$, 20% EtOAc-hexanes eluant) provided 37 mg of the title compound (195 mg theoretical, 19%). $^1$H NMR (300 MHz, acetone-d$_6$) δ 12.4(br s, 1H), 7.6(br s, 1H), 7.1(m, 1H), 7.0–6.8(m, 3H), 6.4(d, 1H, J=7 Hz), 5.4(m, 1H), 5.0(m, 2H), 3.1(m, 2H). $^{19}$F NMR (282 MHz, acetone-d$_6$) δ -75.83(s, 3F), -121.86(s, 1F). Anal. ($C_{16}H_{12}N_2OF_4$) C, H, N.

Example 15

Compound VIII, wherein R=2-cyclopropyl-1-ethyl

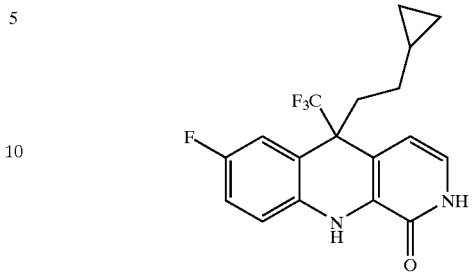

Step B: Preparation of Compound of Formula VIII(R=2-cyclopropyl-1-ethyl).

To a solution of 2-cyclopropylethyliodide (614 mg, 3.15 mmol) in hexanes (8 mL) at -78° C. was added a 1.7M solution of t-BuLi in THF (3.7 mL, 6.3 mmol) and the resulting reaction mixture was allowed to stir at -78° C. for 10 minutes. Ether (8 mL) was added and the reaction mixture was allowed to stir at room temperature for an hour. The reaction mixture was cooled back down to -78° C. and THF (8 mL) was added followed by compound IX (178 mg, 0.63 mmol) and the resulting reaction mixture was allowed to stir at -78° C. for 30 minutes. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, 50% EtOAc-hexanes eluant) provided 45 mg of the title compound (222 g theoretical, 20%). $^1$H NMR (300 MHz, CDCl$_3$) δ 12.55(br s, 1H), 7.6(br s, 1H), 7.2(m, 1H), 7.1–6.9(m, 3H), 6.45(d, 1H, J=7 Hz), 2.5(m, 2H), 1.1(m, 2H), 0.7(m, 1H), 0.5(m, 2H), 0.05(m, 2H). $^{19}$F NMR (282 MHz, CDCl$_3$) δ -75.80(s, 3F), -122.05(s, 1F). Anal. ($C_{18}H_{16}N_2OF_4$) C, H, N.

Example 16

Compound VIII, wherein R=ethynyl

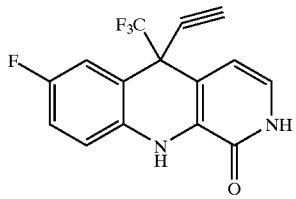

Step B: Preparation of Compound of Formula VIII (R=ethynyl).

To a solution of trimethylsilylacetylene (432 µl, 3.06 mmol) in THF (5 mL) at 0° C. was added a 1.6M solution of n-BuLi in THF (1.7 mL, 2.72 mmol) and the resulting reaction mixture was allowed to stir at 0° C. for 30 minutes. Thereafter, compound IX (192 mg, 0.68 mmol) was added as a suspension in THF (2 mL) and the resulting reaction mixture was allowed to stir with warming to room temperature overnight. The reaction mixture was poured onto saturated NH$_4$Cl and thereafter partitioned between ethyl acetate and water. The combined ethyl acetate extracts were dried over anhydrous MgSO$_4$ and concentrated in vacuo. Chromatography (SiO$_2$, EtOAc eluant) provided 74 mg of the trimethylsilyl protected compound (258 mg theoretical, 29%). $^1$H NMR (300 MHz, acetone-d$_6$) δ 11.2(br s, 1H), 8.8(br s, 1H), 7.45(m, 1H), 7.4(m, 1H), 7.1(m, 1H), 7.05(m, 1H), 6.55(m, 1H), 0.05(s, 9H). $^{19}$F NMR (282 MHz, acetone-$d_6$) δ −77.59(s, 3F), −123.84(s, 1F). High resolution mass spec: calculated for $C_{18}H_{17}N_2OSiF_4$ (M+H)$^+$: 381.1046, found 381.1055.

To a solution of the trimethylsilyl protected compound (74 mg, 0.19 mmol) in methanol (1 mL) was added potassium carbonate (131 mg, 0.95 mmol) and the resulting reaction mixture was allowed to stir at room temperature overnight. The reaction mixture was poured onto water and extracted with ethyl acetate (2×25 mL). The combined ethyl acetate extracts were dried over anhydrous $MgSO_4$ and concentrated in vacuo. Chromatography ($SiO_2$, 50% EtOAc-hexanes eluant) provided 9 mg of the title compound (58 mg theoretical, 16%). $^1$H NMR (300 MHz, acetone-$d_6$) δ 11.0(br s, 1H), 8.6(br s, 1H), 7.5(m, 1H), 7.2(m, 1H), 7.1(d, 1H, J=7 Hz), 6.6(d, 1H, J=7 Hz), 3.6(s, 1H). $^{19}$F NMR (282 MHz, acetone-$d_6$) δ −77.98(s, 3F), −123.95 (s, 1F). High resolution mass spec: calculated for $C_{15}H_9N_2OF_4$ (M+H)$^+$: 309.065101, found 309.063882.

Example 17

Compound XIV, wherein R=2-chloroethyl

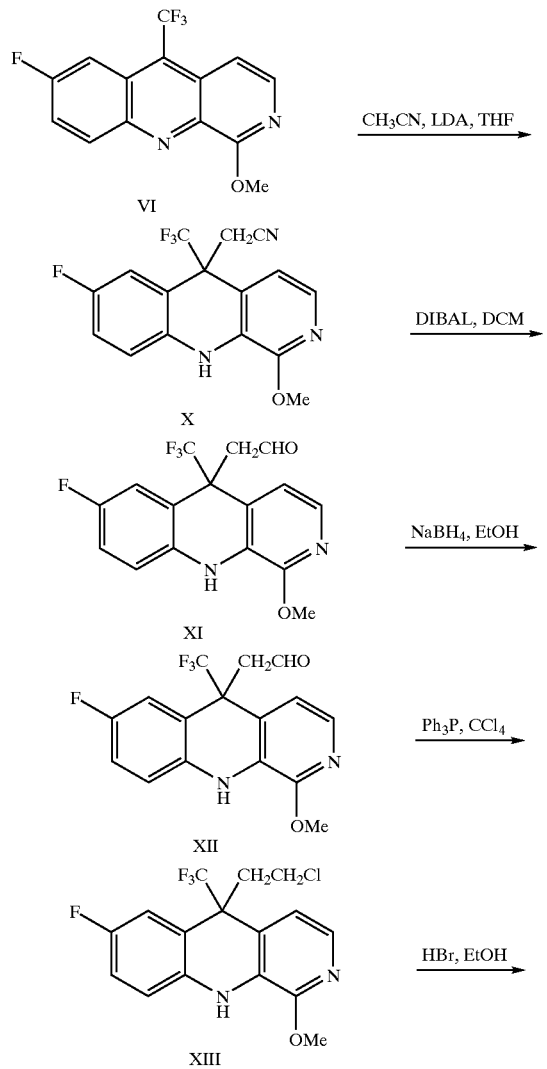

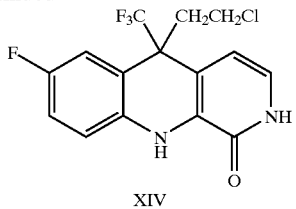

Step A: Preparation of Compound X.

To a solution of acetonitrile (71 μl, 1.36 mmol) in THF (2 mL) at −78° C. was added a 2M solution of LDA in THF (0.76 mL, 1.52 mmol) and the resulting reaction mixture was allowed to stir at −78° C. for 20 minutes. Thereafter, compound VI (100 mg, 0.34 mmol) was added and the resulting reaction mixture was allowed to stir at −78° C. for 30 minutes. The reaction mixture was poured onto saturated $NH_4Cl$ and thereafter partitioned between ethyl acetate and water. The combined ethyl acetate extracts were dried over anhydrous $MgSO_4$ and concentrated in vacuo. Chromatography ($SiO_2$, 20% EtOAc-hexanes eluant) provided 100 mg of compound X (115 mg theoretical, 87%). $^1$H NMR (300 MHz, $CDCl_3$) δ 7.8(d, 1H, J=7 Hz), 7.1(m, 2H), 6.9(m, 2H), 4.06(s, 3H), 3.5(m, 2H). $^{19}$F NMR (282 MHz, $CDCl_3$) δ −76.48(s, 3F), −121.2(s, 1F). Anal. ($C_{16}H_{11}N_3OF_4$) C, H, N.

Step B: Preparation of Compound XI.

To a solution of compound X (100 mg, 0.3 mmol) in dichloromethane (1.5 mL) at −78° C. was added a 1M solution of DIBAL in dichloromethane (0.45 mL, 0.45 mmol) and the resulting reaction mixture was allowed to stir at −78° C. for 2 hours. The reaction mixture was poured onto 20% $KHSO_4$ and thereafter partitioned between ethyl acetate and water. The combined ethyl acetate extracts were dried over anhydrous $MgSO_4$ and concentrated in vacuo. Chromatography ($SiO_2$, 20% EtOAc-hexanes eluant) provided 43 mg of compound XI (102 mg theoretical, 42%). $^1$H NMR (300 MHz, $CDCl_3$) δ 9.5(s, 1H), 7.7(d, 1H, J=7 Hz), 7.1(m, 2H), 6.85(m, 2H), 4.07(s, 3H), 3,5(s, 2H). $^{19}$F NMR (282 MHz, $CDCl_3$) δ −76.66(s, 3F), −121.57(s, 1F). High resolution mass spec: calculated for $C_{16}H_{13}N_2O_2F_4$ (M+H)$^+$: 341.0913, found 341.0888.

Step C: Preparation of Compound XII.

To a solution of compound XI (300 mg, 0.88 mmol) in ethanol (5 mL) at room temperature was added sodium borohydride (100 mg, 2.64 mmol) and the resulting reaction mixture was allowed to stir at room temperature for 15 minutes. The reaction mixture was partitioned between ethyl acetate and water. The combined ethyl acetate extracts were dried over anhydrous $MgSO_4$ and concentrated in vacuo. Chromatography ($SiO_2$, 20% EtOAc-hexanes eluant) provided 257 mg of compound XII (301 mg theoretical, 85%). $^1$H NMR (300 MHz, $CDCl_3$) δ 7.7(d, 1H, J=7 Hz), 7.25(m, 1H), 7.0(m, 2H), 6.8(m, 1H), 6.7(br s, 1H), 4.06(s, 3H), 3.5(m, 2H), 2.7(m, 2H). $^{19}$F NMR (282 MHz, $CDCl_3$) δ −76.51(s, 3F), −122.31(s, 1F). High resolution mass spec: calculated for $C_{16}H_{15}N_2O_2F_4$ (M+H)$^+$: 343.1070, found 343.1072.

Step D: Preparation of Compound XIII.

To a solution of compound XII (250 mg, 0.73 mmol) in acetonitrile (3 mL) at room temperature was added triphenyphosphine (289 mg, 1.10 mmol) followed by carbon tetrachloride (4 mL) and the resulting reaction mixture was allowed to stir at room temperature overnight. The reaction mixture was partitioned between ethyl acetate and water. The combined ethyl acetate extracts were dried over anhydrous $MgSO_4$ and concentrated in vacuo to provide 210 mg of compound XIII (263 mg theoretical, 80%). $^1$H NMR (300 MHz, CDCl$_3$) δ 7.75(d, 1H, J=7 Hz), 7.2(m, 1H), 7.1(m, 1H), 6.95(m, 1H), 6.8(m, 1H), 6.75(br s, 1H), 4.06(s, 3H), 3.25(m, 2H), 2.9(m, 2H). $^{19}$F NMR (282 MHz, CDCl$_3$) δ −76.45(s, 3F), −121.76(s, 1F). High resolution mass spec: calculated for $C_{16}H_{14}N_2OF_4Cl$ (M+H)$^+$: 361.0731, found 361.0748.

Step E: Preparation of Compound XIV.

To a solution of compound XIII (52 mg, 0.144 mmol) in ethanol (1 mL) at room temperature was added a 48% aqueous solution of HBr (1 mL) and the resulting reaction mixture was allowed to stir at reflux for 1.5 hours. The reaction mixture is poured onto saturated NaHCO$_3$ and extracted with ethyl acetate (3×25 mL). The combined ethyl acetate extracts were dried over anhydrous MgSO$_4$ and concentrated in vacuo. Chromatography (SiO$_2$, 50% acetone-hexanes eluant) provided 45 mg of compound XIV (50 mg theoretical, 90%). $^1$H NMR (300 MHz, CDCl$_3$) δ 11.1(br s, 1H), 8.6(br s, 1H), 7.5–7.3(m, 2H), 7.1–7.0(m, 2H), 6.45(m, 1H), 3.4(m, 2H(, 2.95(m, 2H). $^{19}$F NMR (282 MHz, CDCl$_3$) δ −76.75(s, 3F), −123.74(s, 1F).

Examples 18–26 can be made according to the following procedures.

Example 18

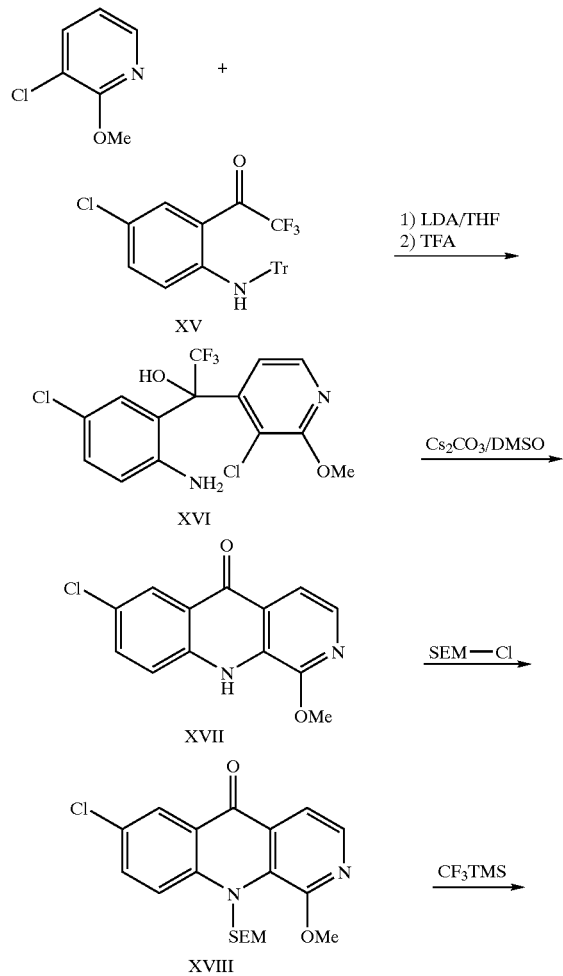

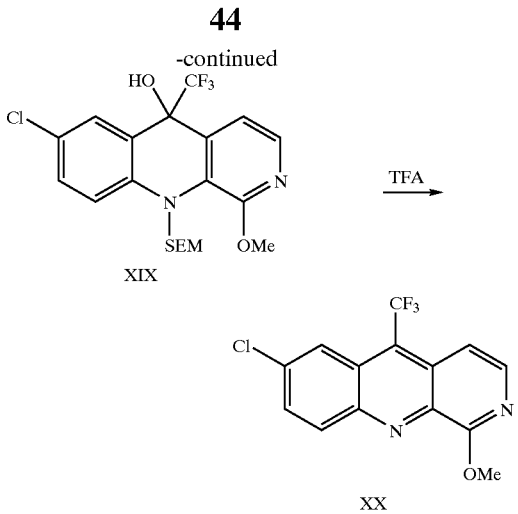

Step A:

To a −78° C. solution of diisopropylamine (3.3 mL, 23.6 mmol) in THF (100 mL) was added a solution of 1.6 M BuLi (16.1 mL, 23.6 mmol) in hexane. After the reaction was stirred for 0.5 h, a solution of 3-chloro-2-methoxypyridine (3.4 g, 23.6 mmol) in THF (2 mL) was added. After stirring for 20 min., ketone (XV) was added. The reaction was allowed to warm to −50° C., quenched with saturated NH$_4$Cl, diluted with EtOAc, and washed with 0.5 N HCl (3×), saturated NaHCO$_3$, and saturated NaCl. The organic phase was dried over Na$_2$SO$_4$ and concentrated to an orange oil (17.5 g). The oil was triturated with CH$_2$Cl$_2$ (30 mL) to give a pale yellow solid (12.7 g, 97% yield) that was treated with TFA to give a detritylated product XVI (5.9 g, 77% yield).

Step B:

To a 120° C. suspension of Cs$_2$CO$_3$ (15 g) in DMSO (50 mL) was added a solution of XVI (5 g, 14.6 mmol) in DMSO (100 mL) dropwise over 1.5 h, then heated at that temperature for 4 h. The reaction was cooled to room temperature and EtOAc (300 mL), water (150 mL) and 1 N HCl (200 mL) were added. A yellow solid precipitated out and was filtered off and washed with water and then EtOAc. The compound was dried at 100° C. under high vacuum overnight to give XVII (2.83 g, 75% yield).

Step C:

To a 0° C. suspension of XVII (2.83 g, 10.9 mmol) and SEM-Cl (6 mL, 33.9 mmol) in DMF (100 mL) was added 60% NaH (1.33 g, 33.2 mmol) and the reaction was stirred for 4 days. The reaction was diluted with EtOAc, washed with water (3×) and brine, and evaporated to give an orange oil (6.85 g). Chromatography and crystallization gave XVIII as yellow crystals (3.72 g, 87% yield).

Step D:

To a 0° C. solution of XVIII (700 mg, 1.79 mmol) and CF$_3$TMS (0.35 mL, 2.37 mmol) in THF (7 mL) was added a solution of 1M TBAF in THF (0.2 mL, 0.2 mmol). After 10 min., additional TBAF (0.3 mL, 0.3 mmol) was added to desilylate the silyl ether. After aqueous work-up, the crude oil was triturated with hexanes to give XIX as an off-white solid (518 mg, 63% yield).

Step E:

A solution of XIX (420 mg) in TFA was stirred for 1.5 h and concentrated to give an oil. The oil was partitioned between EtOAc and 1 N NaOH and washed with water and brine, and evaporated to give XX as a yellow solid (264 mg, 93% yield).

Alternative Method

Step A-2:

To a 0° C. solution of XVI (12 g, 32.7 mmol) and MeI (3.3 mL, 53.5 mmol) in DMF (120 mL) was added 60% NaH (1.44 g, 36 mmol) and stirred overnight. After aqueous work-up, chromatography and trituration gave XXI (6.22 g, 50% yield).

Step B-2:

A solution of XXI (6.4 g, 16.8 mmol) in EtOH (20 mL) and a solution of 48% HBr (20 mL) was refluxed for 1.5 h. The reaction was diluted with EtOAc and neutralized, washed with brine, dried over $Na_2SO_4$ and concentrated to an orange thick oil (8 g). Trituration with ether and $CH_2Cl_2$ gave XXII as a white solid (5.86 g, 95% yield).

Step C-2:

A suspension of XXII (4.7 g) in DMF (95 mL) was refluxed for 1.5 h. EtOAc and water were added and the reaction was filtered and washed with water (2×) and EtOAc (2×). The wet product was dried at 80° C. under high vacuum overnight to give XXIII as a yellow solid (2.85 g, 76% yield).

Step D-2:

A mixture of XX (1.5 g) in 48% HBr (10 mL) and EtOH (10 mL) was refluxed for 2 h. The reaction was diluted with water and neutralized with NaOH. The resulting solid was filtered off and washed with saturated $NaHCO_3$ and water (2×), and dried at 100° C. under high vacuum overnight to give XXIII as a yellow solid (1.33 g, 93% yield).

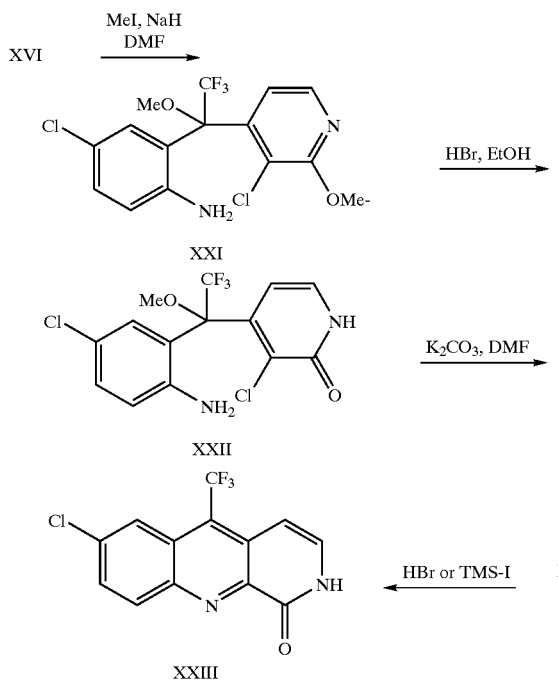

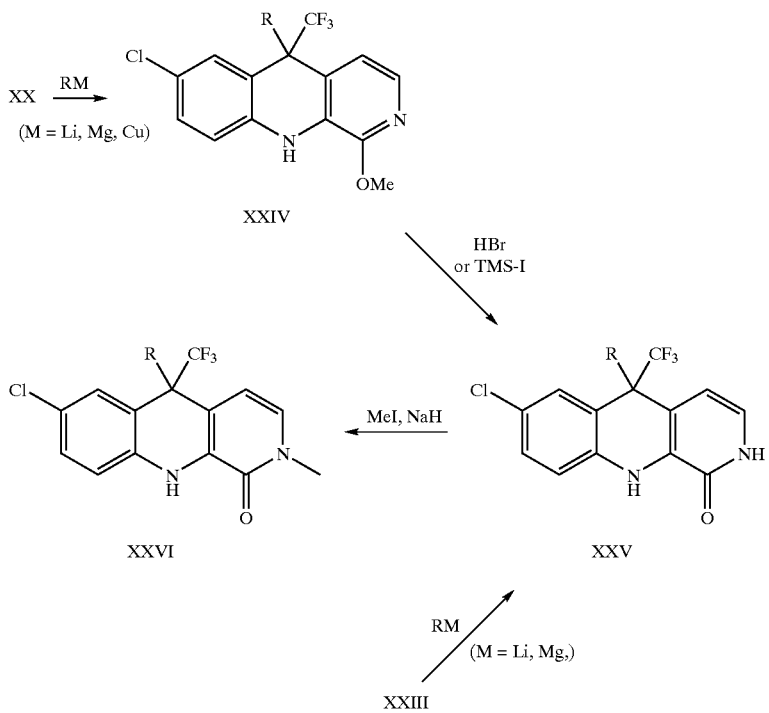

47

Step F:

To a −78° C. solution of diisoproplylamine (1.08 mL, 7.68 mmol) in THF (10 mL) was added a solution of 1.6 M BuLi (4.921 mL, 7.78 mmol) in hexane. After the reaction was stirred for 15 min., 2-picoline (7.59 mL, 7.68 mmol) was added. After stirring for 20 min., XX (600 mg, 1.92 mmol) was added. The reaction was quenched with saturated NH₄Cl, then diluted with EtOAc, washed with 0.1 N HCl (4×), water and saturated NaCl. The organic phase was dried over Na₂SO₄ and concentrated to a dark orange glass (670 mg). Flash chromatography (50% EtOAc/hexanes) gave XXIV (R=2-picolyl (2-pyridylmethyl)) (R=2-picolyl (2-pyridylmethyl) as a thick pink oil (R=2-picolyl, 600 mg, 70% yield).

Step G:

A solution of XXIV (R=2-picolyl (2-pyridylmethyl)) 1.53 g) in 48% HBr (7 mL) and EtOH (7 mL) was refluxed for 1.5 h. The reaction was diluted with EtOAc and THF and neutralized with 1 N NaOH, and washed with brine. The organic phase was dried over Na₂SO₄ and evaporated to give a gray solid (1.32 g). The solid was triturated with boiling dichloroethane (10 mL) to give XXV (1.25 g).

Example 21

A solution of XXIV ((R=cyclopropyl acetylene, 56 mg), DIEA (15 uL) and a solution of 1 M TMS-I in methylene chloride (1 mL) in methylene chloride (5 mL) was stirred overnight. The reaction was diluted with EtOAc and washed with 1 N NaOH and brine. The organic phase was dried over Na₂SO₄ and evaporated to give an orange glass (64 mg). The glass was triturated with ether (2 mL) to give XXV (R=cyclopropyl acetylene) as off-white solid (7.5 mg).

Example 24

XXV, Single Active Enantiomer

To a 0° C. solution of XXV (R=2-picolyl (2-pyridylmethyl), 100 mg, 0.26 mmol) in DMF (2 mL) was added 60% NaH (11.2 mg, 0.28 mL). After stirred for 20 min., MeI (25 uL, 0.4 mmol) was added. After stirring for 10 min., the reaction was diluted with EtOAc and washed with water (2×) and brine. The organic phase was dried over Na₂SO₄ and evaporated to give a brown solid (127 mg). The solid was triturated with ether (2 mL) to give XXVI as a pale orange solid (81 mg, 84% yield).

Example 20

To a −78° C. solution of 85% cyclopropylethyl iodide (9.66 g, 41.5 mmol) in hexanes (75 mL) was added a solution of 1.7 M t-BuLi in pentane (49.3 mL, 83.8 mmol). After 5 min., ether (75 mL) was added and the reaction was warmed to room temperature for 1 h to destroy any excess of t-BuLi. The reaction was cooled back to −78° C. and THF (20 mL) was added. This −78° C. reaction mixture was added to a −78° C. suspension of XXIII (2.5 g, 8.38 mmol) in THF (100 mL) and TMEDA (10 mL). The reaction was quenched with saturated NH₄Cl, then diluted with EtOAc, washed with 1 N HCl, water and saturated NaCl. The organic phase was dried over Na₂SO₄ and concentrated to an orange oil. Flash chromatography (25–50% EtOAc/hexanes) and trituration (dichloroethane and hexanes) gave XXV as a brown solid (R=cyclopropylethyl, 1.76 g, 58% yield).

48

Example 22

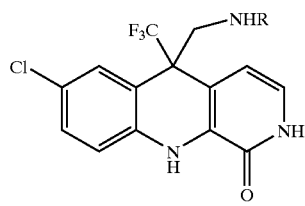

XXVIII

The compound XXVIII (R=cyclopropylaminomethyl) was made by the method described in Example 30, below.

Example 28

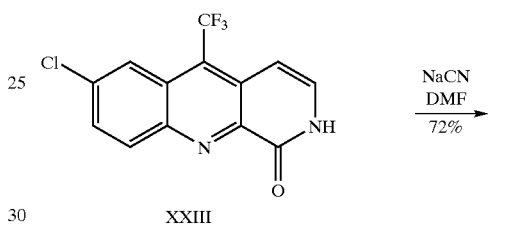

XXIII

NaCN
DMF
72%

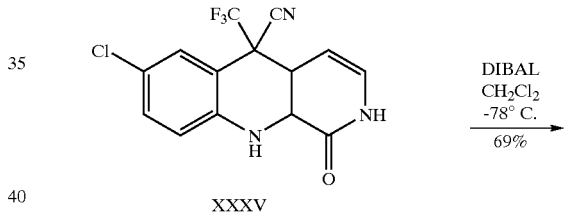

XXXV

DIBAL
CH₂Cl₂
−78° C.
69%

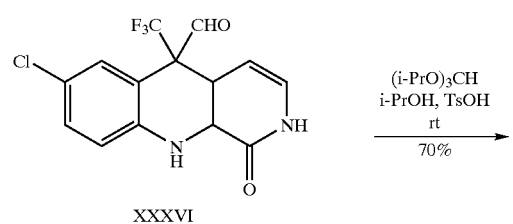

XXXVI (i-PrO)₃CH
i-PrOH, TsOH
rt
70%

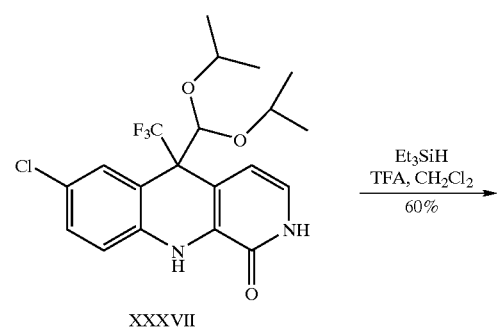

XXXVII

Et₃SiH
TFA, CH₂Cl₂
60%

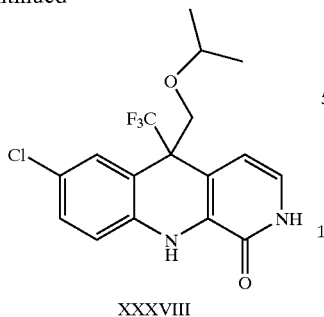

XXXVIII

Step A:

A suspension of XXIII (17.5 g) and NaCN (5.86 g) in DMF (450 mL) was stirred for 3 days. The reaction was diluted with EtOAc and washed with saturated NaHCO$_3$, water and brine. The organic phase was dried over Na$_2$SO$_4$ and concentrated to a gray solid which triturated with methylene chloride (20 mL) to give a yellow solid XXXV (14.2 g, 72% yield). The compound XXXV was treated with DIBAL in methylene chloride at −78° C. to give a brown solid (14.2 g) after 3 N HCl/EtOAc workup. The crude solid was triturated with methylene chloride (20 mL) to give a yellow solid XXXIV (9.7 g, 69% yield).

Step B:

A suspension of XXXIV (5 g) and TsOH (4.6 g, 2 eq) in i-PrOH (100 mL) and (i-PrO)$_3$CH (40 mL) was stirred for 45 min. The reaction was diluted with EtOAc and washed with 1 N NaOH, water and brine. The organic phase was dried over Na$_2$SO$_4$ and concentrated. Flash chromatography (75% EtOAc/hexanes) and trituration (ether and hexanes) gave a pale yellow solid XXXVII (3.7 g, 70% yield).

Step C:

A solution of XXXVII (3.5 g) in Et$_3$SiH (70 mL), CH$_2$Cl$_2$ (35 mL) and TFA (70 mL) was stirred overnight and solvents were evaporated. The reaction was diluted with EtOAc and washed with 1 N NaOH, water and brine. The organic phase was dried over Na$_2$SO$_4$ and concentrated. Flash chromatography (75% EtOAc/hexanes) and trituration (ether and hexanes) gave a pale yellow solid XXXVIII (1.9 g, 60% yield).

Example 30

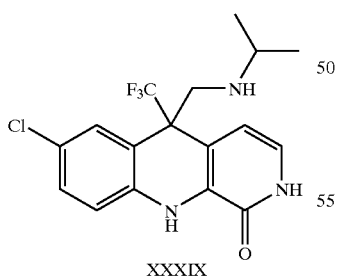

XXXIX

A suspension of XXXVI (2.89 g), isopropylamine (4.5 mL) and acetic acid (9 mL) in toluene (440 mL) was stirred for 4 days. Then NaCNBH$_3$ (0.6 g) and MeOH (44 mL) were added to the reaction. After stirring for 2.5 h, The reaction was diluted with EtOAc and washed with saturated NaHCO$_3$, water and brine. The organic phase was dried over Na$_2$SO$_4$ and concentrated to a yellow solid XXXIX (2.3 g, 68% yield).

Example 37

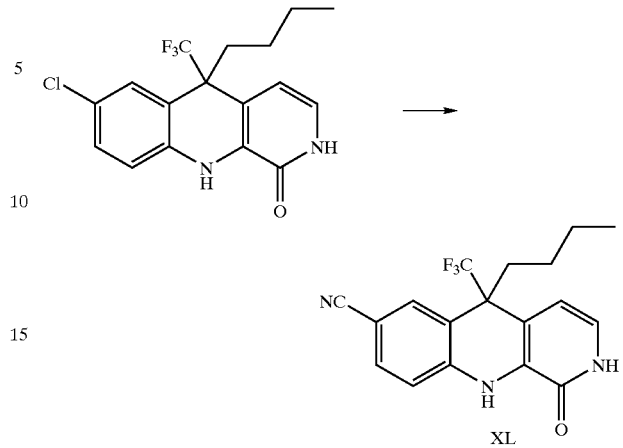

XL

The compound of Example 18 (2.13 grams) was dissolved in 150 ml of N,N-dimethylacetamide. 1,1'-bis (diphenylphosphino)ferrocene (1.33 g, 0.4 equivalents), zinc cyanide (1.40 g, 2.0 equivalents) and zinc powder (0.47 g 1.2 equivalents) were added. The mixture was degassed under high vacuum, and then 1.09 g (0.2 equivalents) of tris(dibenzylideneacetone)dipalladium(0) was added. The mixture was degassed once again, and heated to reflux for 18 hours. The black mixture was cooled and partitioned between ethyl acetate and 2N ammonium hydroxide. Both phases were filtered through Celite and separated. The organic phase was washed twice with water and dried over magnesium sulfate. Flash chromatography (silica gel, 50% EtOAc/hexane) yielded 1.44 g (69% yield) of compound XL as a brown solid M.S. 346.2 (M−H)$^-$.

Example 38

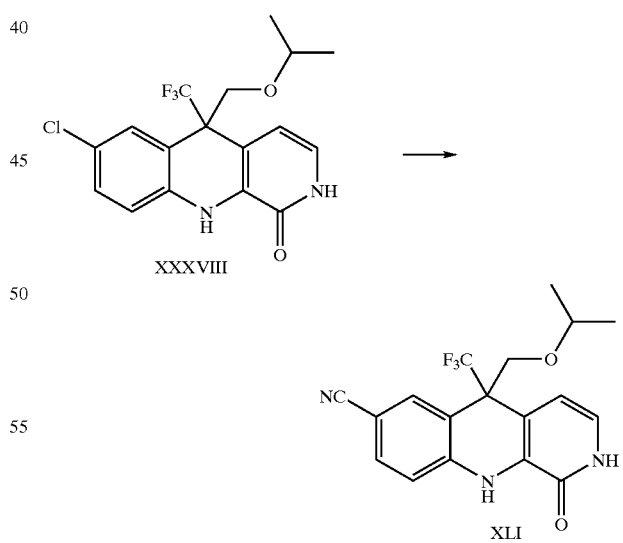

XLI

Pyridone XXXVIII (2.92 grams) was dissolved in 75 ml of N-methylpyrrolidinone. 1.92 g (2.0 equivalents) of zinc cyanide and 1.18 g (2.2 equivalents) of zinc powder were added. The mixture was degassed under high vacuum, and then 7.34 g (1.1 equivalents) of dichloro[1,1'-bis (diphenylphosphino)ferrocene]palladium(II) dichloromethane adduct was added. The mixture was degassed once again, and heated to 170° C. 18 hours. The mixture was cooled and partitioned between ethyl acetate and 2N ammonium hydroxide. Both phases were filtered through Celite and separated. The organic phase was washed twice with water and dried over magnesium sulfate. Flash chromatography (silica gel, 50% EtOAc/hexane) yielded 1.76 g (59% yield) of compound XLI as a brown solid, M.S. 362.2 (M−H)⁻.

The 4-alkylthiomethyl derivatives were synthesized using the synthetic Scheme shown below. Sulfoxide XLII was deprotonated with a strong base, such as lithium, sodium or potassium diisopropylamide or a similar amine anion in an inert solvent such as THF to give the corresponding deprotonated species. This was added to the pyridone core XXIII, to form a mixture of diastereomers XLIII at temperature ranges from −78 to 25° C. The diastereomeric mixture or each individual diastereomer was deoxygenated by an appropriate reagent such as TiI₄ in an inert solvent such as acetonitrile by the process described by Shimizu et al. Synlett. 2000, 1437, to give the corresponding sulfide.

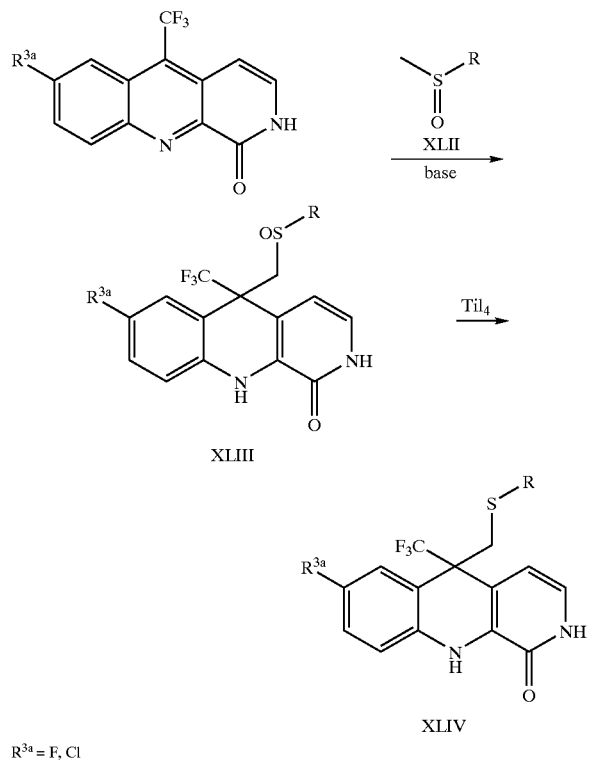

XLIII

XLIV

R³ᵃ = F, Cl

Example 39

Compound XLIV Wherein R³ᵃ is Cl, R is Cyclopropyl

Step A:

Cyclopropylmethyl sulfoxide: Cyclopropylbromide (8 mL, 0.1 mol) in ether (10 mL) was added dropwise into a suspension of Mg turnings (2.43 g, 0.1 mol) in ether (90 mL). After the addition was over the reaction was stirred at 25° C. for 3 hours and heated at reflux for 3 hours. Then it was cooled to 0° C. and (CH₃S)₂ (9 mL, 0.1 mol) was added dropwise and the mixture was stirred at 0° C. for 1 hour, at 25° C. for 20 hours and at reflux for 3 hours. After cooling it was quenched with water (5 mL) and 5% HCl (3 mL). The precipitated solids were filtered off and the filtrate was washed with water, brine, dried (MgSO₄), and distilled at atmospheric pressure. The fraction distilled at 100–110° C. consisted of a 1:1 mixture of cyclopropylmethylsulfide and methyl disulfide (4.4 g).

Step B:

Two grams of the above mixture (~22.2 mmol) in CH₂Cl₂ (50 mL) was cooled to −5° C. in a salt/ice bath and 4 g m-chloroperbenzoic, 70–75% acid was added in potions. The reaction was stirred at −5° C. for 2 hours and at 25° C. for 20 hours. Then it was quenched with satNaHCO₃, satNa₂S₂O₅, diluted with CH₂Cl₂ (50 mL) and washed with satNaHCO₃ (2×30 mL), brine, dried and stripped in vacuo. NMR analysis of the crude residue indicated that it consisted of the product, cyclopropyl methyl sulfoxide and ~10% of the corresponding sulfone. ¹H NMR(CDCl₃) 2.66 (s, 3H), 2.14–2.19 (m, 1H), 0.8–1.22 (m, 4H).

Step C:

To a solution of diisopropylamine (0.22 mL, 1.64 mmol in THF (3 mL) at −78° C. (dry ice/acetone bath) a 1.6 solution of nBuLi in hexanes (0.84 mL, 1.36 mmol) was added and the mixture was warmed to 0° C., stirred for 10 min and cooled back to −78° C. To the solution of LDA formed, cyclopropyl methyl sulfoxide (1.42 mg, 1.36 mmol) in THF (3 mL) was added and the reaction mixture was stirred at −78° C. for 30 min. Then the temperature was adjusted at −40° C. (acetonitrile/dry ice bath) and pyridone XXIII (100 mg, 0.34 mmol) was added as a solid. The reaction was stirred at −40° C. for 3 hours, quenched with 10% NH₄Cl and partitioned between EtOAc (100 mL) and brine (20 mL). The EtOAc extract was dried and stripped in vacuo. The residue was chromatographed on silica gel using EtOAc 1% methanol/EtOAc and 5% methanol/EtOAc to give the product. This was washed with ether to give the sulfoxide adduct XLIII as a mixture of diastereomers (47 mg).

Example 39a

Step D:

The diastereomeric mixture of the sulfoxides from the previous reaction (43 mg, 0.11 mmol) was added into a mixture of TiI₄ (93 mg, 0.17 mmol) in acetonitrile (2 mL) at 0° C. The reaction was stirred at 0° C. for 45 min and quenched with satNaHCO₃ (10 mL) and satNa₂S₂O₅ (5 mL). Then it was partitioned between EtOAc (100 mL) and water (20 mL), The EtOAc was washed with brine, dried (MgSO4), and stripped in vacuo. The crude product was purified by column chromatography using EtOAc and 2% methanol/EtOAc to give XLIV (26 mg). ¹H NMR(CDCl₃): 10.7–10.8 (br s, 1H), 7.40 (br s, 1H), 7.25 (dd, 1 H, J=2.2, 8.8 Hz), 6.89 (d, 1H, J=7.3 Hz), 6.83 (d, 1H, J=8.8 Hz), 6.32 (d, 1H, J=7.3 Hz), 3.64 (d, 1H, J=13.9 Hz), 3.55 (d, 1H, J=13.9 Hz), 1.48-1–58 (m, 1H), 0.76–0.80 (m, 2H), 0.42–0.47 (m, 2H).

Examples 40–46 were prepared using the procedure described in Example 39.

Example 40

Compound XLIII (R³ᵃ is Chloro and R is i-propyl

The compound was prepared as described above. The compound was chromatographed on silica gel. The eluent used was a gradient of 90% ethyl acetate/hexane to ethyl acetate to afford one diastereomer, brown solid, 59 mg, mp 238° C. (decomp). Yield 27%. APCI-MS calcd. for C₁₇H₁₆ClF₃N₂O₂S (404.057): (M+H+CH₃CN)⁺=446.0, 100%. ¹H NMR (DMSO): 11.8–11.9 (d, 1H); 9.3 (s, 1H); 7.5

(s, 1H); 7.33 (d, 1H, J=8.8 Hz); 7.25 (d, 1H J=7.0 Hz,); 6.92 (t, 1H); 6.33 (d, 1H, J=7.0 Hz); 3.84 (d, 2H, J=4.1 Hz); 2.95 (m, 1H); 1.20 (d, 3H, J=7.0 Hz); 1.13 (d, 3H J=6.9 Hz).

Chromatographed using the same conditions as in to afford the other diastereomer, yellow solid, 63 mg, 223° C. (decomp). Yield 28%. APCI-MS calcd. For $C_{17}H_{16}ClF_3N_2O_2S$ (404.057): $(M+H+CH_3CN)^+$=446.0, 100%. $^1$H NMR (DMSO): 11.7 (d, 1H); 9.29 (s, 1H); 7.55 (s, 1H); 7.38 d, 1H, J=8.8 Hz); 7.31 (d, 1H, J=1.9 Hz); 6.8 (t, 1H); 6.3–6.4 (d, 1H); 3.6–4.0 (doublet of doublets, 2H); 2.9 (m, 1H); 1.18 (d, 3H, J=6.6 Hz); 1.13 (d, 3H, J=7 Hz).

Example 41

Compound XLIII wherein $R^{3a}$ is Chloro and R is t-butyl

The compound was chromatographed on silica gel. The eluent used was a gradient of 90% ethyl acetate-hexane to 5% methanol/ethyl acetate to afford the diastereomer, which was washed with ether/hexanes to give a light yellow solid, 15 mg, 193° C. (decomp). Yield 13%.

APCI-MS calcd. for $C_{18}H_{18}ClF_3N_2O_2S$ (418.073): $(M+H+CH_3CN)^+$=460.1, 100%.

The compound was chromatographed on silica gel. The eluent used was a gradient of 90% ethyl acetate-hexane to 5% methanol/ethyl acetate to afford the other diastereomer, which was recrystallized from ethyl acetate/methanol/hexanes to give a light brown solid, 9 mg. Yield 8%.

APCI-MS calcd. for $C_{18}H_{18}ClF_3N_2O_2S$ (418.073): $(M+H+CH_3CN)^+$=460.1, 100%.

Example 42

Compound XLIV wherein $R^{3a}$ is Chloro and R is Methyl

Synthesized in a similar manner as described earlier. The crude reaction product was washed with ether and had a purity of 95% by HPLC analysis (82% yield). $^1$H NMR (dmso) 11.82 (brs, 1H), 9.25 (brs, 1H), 7.55 (brs, 1H), 7.34 (d, 1H, J=8.7 Hz), 7.27 (dd, 1H, J=2.2, 8.7 Hz), 6.91 (d, 1H, J=6.9 Hz), 6.4 (d, 1H, J=6.9 Hz), 3.82 (d, 1H, J=13.5 Hz), 3.59 (d, 1H, J=13.5 Hz), 2.00 (s, 3H)

Example 43

Compound XLIV wherein $R^{3a}$ is Chloro and R is Ethyl

Purified by silica gel chromatography (EtOAc eluent, 75% yield). $^1$H NMR(CDCl$_3$): 7.4 (brs, 1H), 7.35 (brs, 1H), 7.24 (dd, 1H, J=2.2, 8.2 Hz), 6.92 (d, 1H), 6.83 (d, 1H, J=8.2 Hz), 6.35 (d, 1H), 3.4–3.6 (d,d 2H), 2.48 (q, 2H), 1.20 (t, 3H).

Example 44

Compound XLIV wherein $R^{3a}$ is Chloro and R is i-propyl

Pale yellow solid, 30 mg. mp=220–221° C. Yield 76%. APCI-MS calcd. for $C_{17}H_{16}ClF_3N_2OS$ (388.062): $(M+H+CH_3CN)^+$=430.1, 88%.

Example 45

Compound XLIV wherein $R^{3a}$ is Fluoro and R is i-propyl

Orange solid, 14 mg. mp=215–216° C. Yield 40%. APCI-MS calcd. for $C_{17}H_{16}F_4N_2OS$ (372.092): $(M+H+CH_3CN)+$=414.1, 100%.

Example 46

Compound XLIV wherein $R^{3a}$ is Chloro and R is t-butyl

White solid, 9 mg. mp=247–249° C. Yield 36%. APCI-MS calcd. for $C_{18}H_{18}ClF_3OS$ (402.078): $(M+H+CH_3CN)^+$=444.1, 100%.

Example 47

Compound CVI

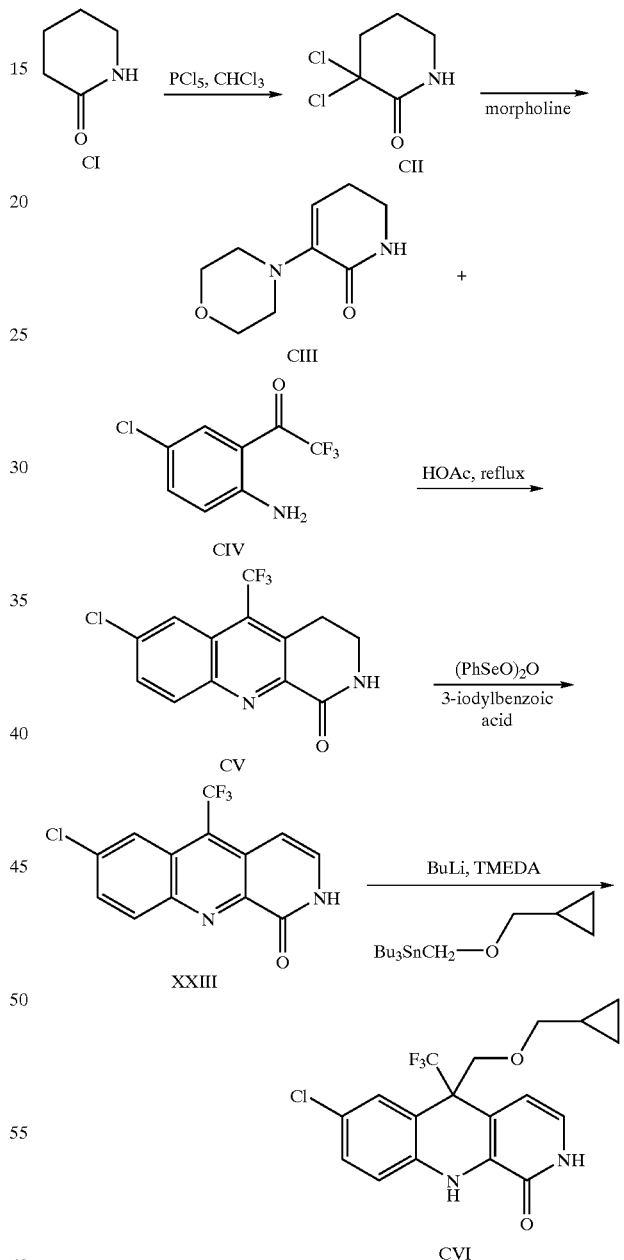

Step A: Preparation of Compound CII.

To a 50° C. solution of 20.8 g of phosphorous pentachloride in 150 mL of chloroform was added 2.97 g of 2-piperidone (CI) dropwise over 15 min. The reaction mixture was warmed to 75° C. and stirred at that temperature for 4.5 h. The cooled reaction mixture was slowly poured onto 150 mL of ice water with vigorous stirring keeping the temperature from 25–30° C. After stirring an additional 15 min, the mixture was extracted with methylene chloride and the extracts were washed first with aqueous sodium bicarbonate then brine, dried over sodium sulfate, and evaporated to afford 4.5 g of CII as a pure solid.

Step B: Preparation of Compound CV.

A mixture of 4.39 g of 3,3-dichloropiperidone (CII) and 13 ml of morpholine was heated at 128° C. for 2 h and then evaporated to dryness. The crude morpholine enamine (CIII) thus obtained was combined with 6.43 g of CIV and 60 ml of acetic acid and was stirred for 6 h at reflux and overnight at room temperature. Evaporation of the solvent followed by trituration with water afforded a solid product which after recrystallization from ethyl acetate/hexane afforded 6.27 g of CV.

Step C: Preparation of Compound XXIII.

A mixture of 500 mg of CV, 700 mg of 3-iodylbenzoic acid (prepared as described by Barton, 1982, *J. Chem. Soc. Perkin Trans. I*, 1947–1952), 30 mg of benzeneseleninic acid (70%, from Aldrich Chemical Co.) and 35 mL of dry toluene was refluxed for 19 h. The mixture was evaporated to dryness, 80 mL of aqueous sodium bicarbonate was added, and the mixture was stirred vigorously for 30 min. The yellow solid was collected, washed with water and methanol to afford 390 mg of XXIII as bright yellow crystals.

Step D: Preparation of Tributyl (cyclopropylmethoxymethyl)tin.

To a solution of 1.15 g of cyclopropyl carbinol in 30 mL of dry THF was added 312 mg of 98% sodium hydride. After stirring 1 h, 2.8 g of iodomethyl tributyltin (prepared as described by Seitz et al, 1983 *Synthetic Commun.* 13, 129) was added and the reaction mixture was stirred at room temperature for 24 h, and then poured onto water and extracted with hexanes. The extracts were washed with brine, dried and evaporated to a crude product that was purified by flash chromatography (hexanes then 30% ethyl acetate/hexanes eluents) to afford 1.03 g of tributyl (cyclopropylmethoxymethyl)tin as a colorless oil.

Step E: Preparation of Compound CVI.

To a −78° C. solution of 565 mg of tributyl (cyclopropylmethoxymethyl)tin and 0.5 ml of TMEDA in 5 mL of anhydrous THF was added 0.53 ml of 2.5M butyllithium in hexane. After 5 min, 100 mg of XXIII was added in a single portion, and the stirred suspension was stirred at −50° C. for 45 min. The cold reaction mixture was quenched by the addition of aqueous ammonium chloride, and then extracted with ethyl acetate. The extracts were washed with brine, dried over sodium sulfate, and evaporated to an oily solid which was triturated with hexane to remove the tetraalkyltin byproduct. The crude solid was purified by preparative tlc (75% EtOAc/hexanes eluent) to give after crystallization (CH$_2$Cl$_2$/EtOAc/hexanes) 23 mg of CVI (mp 250° C.).

Example 48

Compound CVII

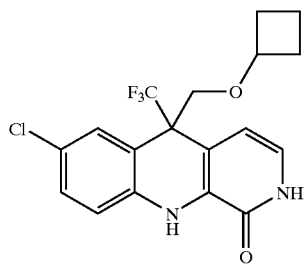

Step A: Preparation of Tributyl (cyclobutyloxymethyl)tin.

To a solution of 2.3 g of cyclobutanol in 60 mL of dry THF was added 624 mg of 98% sodium hydride. After stirring 2 h, 5.6 g of iodomethyl tributyltin (prepared as described by Seitz et al 1983 *Synthetic Comm.* 13 129) was added and the reaction mixture was stirred at room temperature for 48 h, and then poured onto water and extracted with hexanes. The extracts were washed with brine, dried and evaporated to a crude product that was purified by flash chromatography (hexanes then 67% ethyl acetate/hexanes eluents) to afford 1.64 g of tributyl (cyclobutyloxymethyl)tin as a colorless oil.

Step B: Preparation of Compound CVII.

To a −78° C. solution of 565 mg of tributyl (cyclobutyloxymethyl)tin and 0.5 ml of TMEDA in 5 mL of anhydrous THF was added 0.625 ml of 1.6 M butyllithium in hexane. After 5 min, 75 mg of XXIII was added in a single portion, and the stirred suspension was stirred at −50° C. for 40 min. The cold reaction mixture was quenched by the addition of aqueous ammonium chloride, and then extracted with ethyl acetate. The extracts were washed with brine, dried over sodium sulfate, and evaporated to an oily solid which was triturated with hexane to remove the tetraalkyltin byproduct. The crude solid was purified preparative tlc (75% EtOAc/hexanes eluent) to give 11.3 mg of CVII (mp 245° C.).

Example 49

Compound CVIII

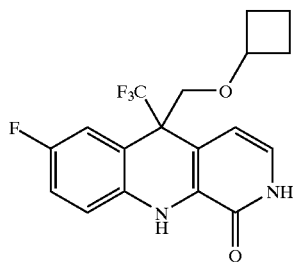

To a −78° C. solution of 565 mg of tributyl cyclobutyloxymethyltin and 0.5 ml of TMEDA in 5 mL of anhydrous THF was added 0.626 ml of 1.6 M butyllithium in hexane. After 5 min, 100 mg of IX was added in a single portion, and the stirred suspension was stirred at −50° C. for 40 min. The cold reaction mixture was quenched by the addition of aqueous ammonium chloride, and then extracted with ethyl acetate. The extracts were washed with brine, dried over sodium sulfate, and evaporated to an oily solid which was triturated with hexane to remove the tetraalkyltin byproduct.

The crude solid was purified by preparative tlc (75% EtOAc/hexanes eluent) to give 12 mg of CVIII (mp 224°C.)

Example 50

Compound CIX

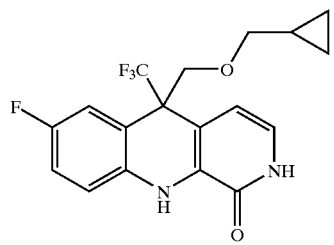

To a −78° C. solution of 800 mg of tributyl cyclopropylmethoxymethyltin and 0.7 ml of TMEDA in 7 mL of anhydrous THF was added 0.90 ml of 1.6 M butyllithium in hexane. After 5 min, 100 mg of IX was added in a single portion, and the stirred suspension was stirred at −50° C. for 40 min. The cold reaction mixture was quenched by the addition of aqueous ammonium chloride, and then extracted with ethyl acetate. The extracts were washed with brine, dried over sodium sulfate, and evaporated to an oily solid which was triturated with hexane to remove the tetraalkyltin byproduct. The crude solid was purified by preparative tlc (75% EtOAc/hexanes eluent) to give 20 mg of CIX as a crystalline solid (mp 203–204° C.).

Example 51

Compound CXVIII

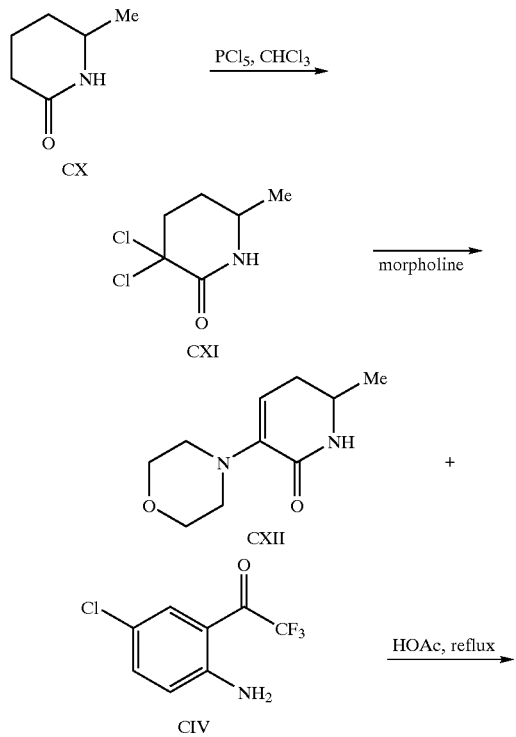

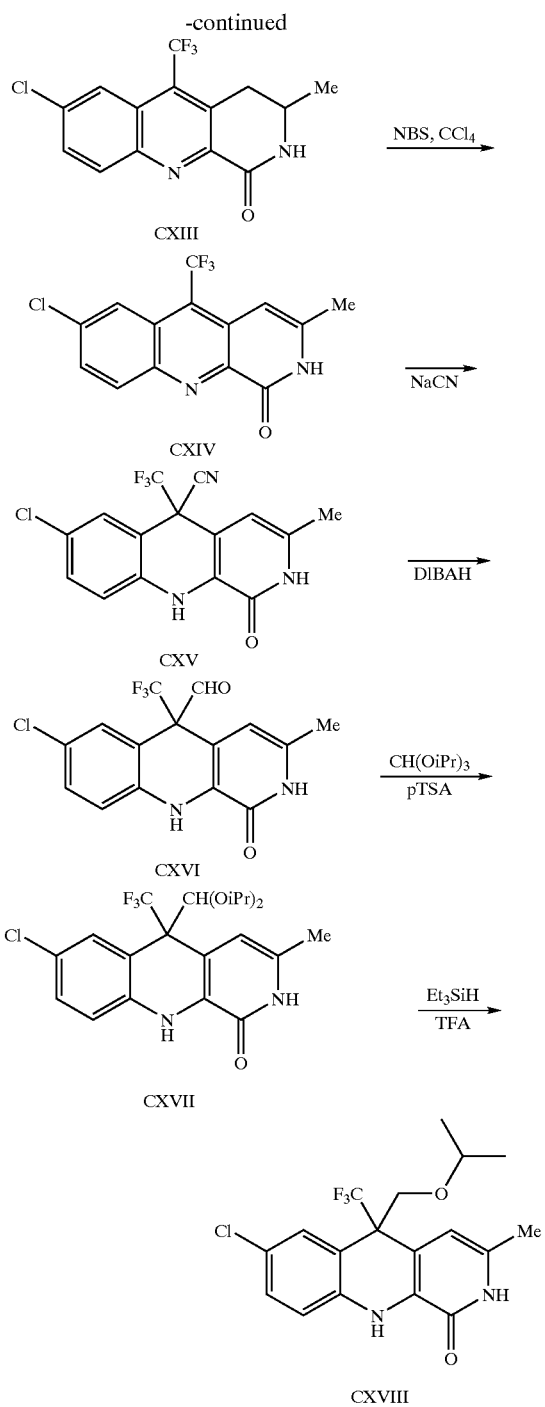

Step A: Preparation of Compound CXI.

To a 50° C. solution of 31.9 g of phosphorous pentachloride in 225 mL of chloroform was added 5.2 g of 6-methyl-2-piperidone (CX) portionwise over 15 min. The reaction mixture was warmed to 75° C. and stirred at that temperature for 4.5 h. and then at room temperature overnight. The cooled reaction mixture was slowly poured onto 225 mL of ice water with vigorous stirring keeping the temperature from 25–30° C. After stirring an additional 10 min, excess aqueous sodium bicarbonate was added and after 10 min, the mixture was extracted with methylene chloride and the extracts were washed with brine, dried over sodium sulfate, and evaporated to afford 6.7 g of CXI as a pure solid.

Step B: Preparation of Compound CXIII.

A mixture of 1.56 g of 6-methyl-3,3-dichloropiperidone (CXI) and 4.5 ml of morpholine was heated at 128° C. for 2 h and then evaporated to dryness.

The crude morpholine enamine (CXII) thus obtained was combined with 2.14 g of CIV and 20 ml of acetic acid and was stirred for 3 h at reflux, and at room temperature overnight. Evaporation of the solvent followed by trituration with water afforded a solid product which after recrystallization from ethyl acetate/hexane afforded 1.86 g of CXIII.

Step C: Preparation of Compound CXIV.

A mixture of 1.5 g of CXIII, 850 mg of N-bromosuccinimide, and 150 mg of Vazo52 in 250 ml of carbon tetrachloride was refluxed for 1 h and the solvent was removed on the rotary evaporator. Recrystallization of the crude product afforded 680 mg of CXIV as yellow crystals.

Step D: Preparation of Compound CXV.

A mixture of 1.28 g of CXIV, 250 mg of sodium cyanide, and 25 mL of DMF was stirred at room temperature for 22 h. The reaction mixture was diluted with ethyl acetate, washed three times with water, dried over sodium sulfate and evaporated. Recrystallization from ether/hexane afforded 1.07 g of CXV.

Step E: Preparation of Compound CXVI.

To a suspension of 500 mg of CXV in 50 ml of anhydrous methylene chloride at −78° C. was added dropwise 6.6 mL of 1M diisobutylaluminum hydride in toluene. After 2 h at −78° C. the cold reaction mixture was poured onto a mixture of 250 mL of 3N HCl and 250 ml of ethyl acetate which was stirred for 10 min. The organic layer was washed with aqueous sodium bicarbonate, dried over sodium sulfate, and evaporated to 508 mg of CXVI.

Step F: Preparation of Compound CXVII.

A mixture of 900 mg of CXVI, 180 mg of p-toluenesulfonic acid, 10 mL of triisopropyl orthoformate, and 10 mL of isopropanol. was stirred at room temperature for 1 h. The reaction mixture was diluted with ethyl acetate, washed 3× with 0.1N NaOH, water, then brine, dried over sodium sulfate and evaporated to a crude oil that was purified by flash chromatography (67% EtOAc/hexanes) to afford 600 mg of CXVII.

Step G: Preparation of Compound CXVIII.

A mixture of 583 mg of CXVII, 6 mL of triethylsilane, 12 mL of trifluoroacetic acid, and 12 ml of dry methylene chloride was stirred overnight at room temperature and then evaporated to dryness. The crude product was dissolved in ethyl acetate, washed twice with aqueous sodium bicarbonate then brine, dried over sodium sulfate and evaporated to 570 mg of a solid. This was dissolved in a hot mixture of ethyl acetate and methylene chloride and the cooled solution deposited 140 mg of a crystalline byproduct. The mother liquor was subjected to flash chromatography on silica gel (eluted with 33%, 50%, and 67% ethylacetate/hexane) to afford 235 mg of CXVIII as colorless crystals (mp 234–235° C.).

Example 52

Compound CXIX

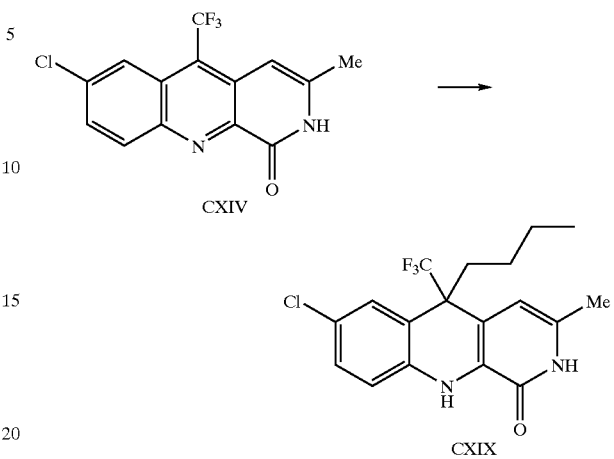

To a −78° C. mixture of 107 mg of CXIV in 10 mL of dry THF and 1 mL of TMEDA was added dropwise 1.0 mL of 1.6 M butyllithium and the mixture was stirred 30 min at −78° C. The cold reaction mixture was quenched by the addition of aqueous citric acid, and then extracted with ethyl acetate. The extracts were washed with brine, dried over sodium sulfate, and evaporated to an oil that was purified by flash chromatography (33% EtOAc/hexanes eluent) to give after recrystallization from ether/hexanes 60 mg of CXIX as a crystalline solid (mp 206–208° C.).

Example 53

Compound CXX

A degassed mixture of 41 mg of CXIX, 26 mg of zinc cyanide, 90 mg of Pd(dppf)Cl$_2$CH$_2$Cl$_2$, 16 mg of zinc powder, and 1.5 mL of N-methylpyrrolidone was stirred under nitrogen for 25 h at 150° C. The cooled mixture was diluted with ethyl acetate and filtered through a pad consisting of layers of sand, silica gel, and celite. The filtrate was washed with 2N NaOH and brine, dried over sodium sulfate and evaporated. Flash chromatography (50% EtOAc/hexanes eluent) gave after recrystallization from ethyl acetate/hexanes 16 mg of CXX as a crystalline solid (mp 254–255° C.).

Example 54

Compound CXXV

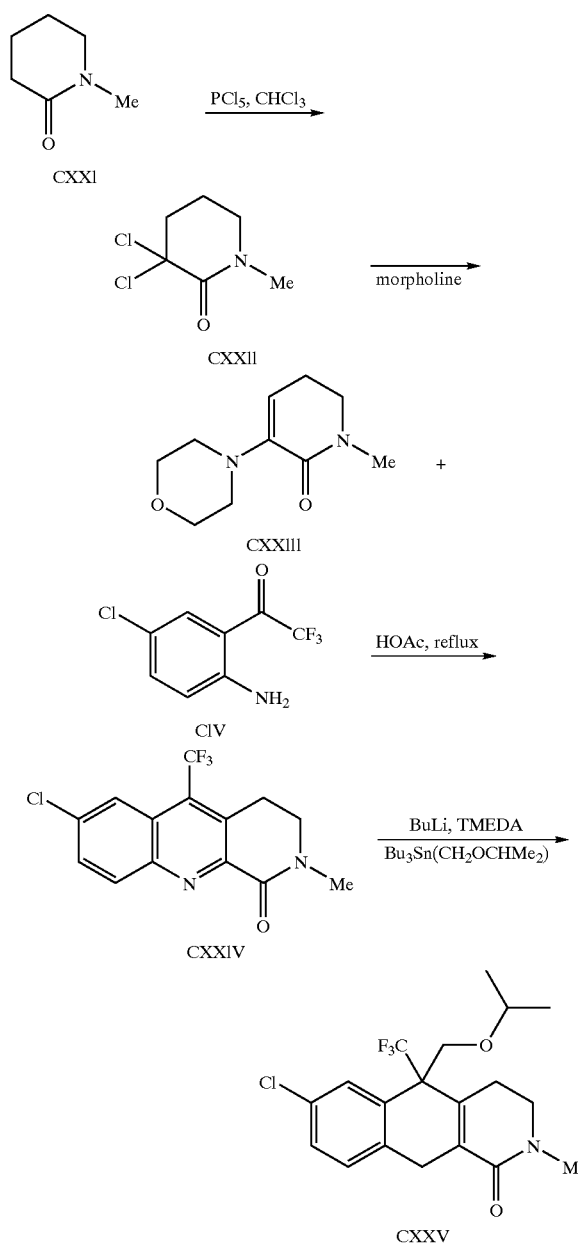

Step A: Preparation of Compound CXXII.

To a 50° C. solution of 20.8 g of phosphorous pentachloride in 150 mL of chloroform was added 3.39 mL of 1-methyl-2-piperidone (CXXI) dropwise over 15 min. The reaction mixture was warmed to 75° C. and stirred at that temperature for 4.5 h. The cooled reaction mixture was slowly poured onto 150 mL of ice water with vigorous stirring keeping the temperature from 25–30° C. After stirring an additional 15 min, the mixture was extracted with methylene chloride and the extracts were washed first with aqueous sodium bicarbonate then brine, dried over sodium sulfate, and evaporated to afford 5.0 g of CXXII as a pure oil.

Step B: Preparation of Compound CXXIV.

A mixture of 1.0 g of CXXII and 5 ml of morpholine was heated at 128° C. for 1.25 h and then evaporated to dryness. The residue was dissolved in methylene chloride, washed with water and aqueous citric acid, dried and evaporated to 0.5 g of CXXIII as an oil.

The crude morpholine enamine (CXXIII) thus obtained was combined with 500 mg of CIV and 9 ml of acetic acid and was stirred at reflux for 4.5 h. After evaporation of the solvent, the crude product was partitioned between methylene chloride and water and the organic layer was washed with aqueous sodium bicarbonate, dried, evaporated and purified by flash chromatography (10% MeOH/methylene chloride) to give 453 mg of CXXIV as a solid product.

Step C: Preparation of Tributyl (isopropoxymethyl)tin

To a solution of 4.6 mL diisopropylamine in 40 mL of dry THF at −20° C. was added dropwise first 12.0 ml of 2.5 M butyllithium and then 8.1 ml of tributyltinhydride. After 10 min this solution was cooled to −78° C., and 3.25 g of chloromethyl isopropyl ether (Molina et al, 1982 *Synthesis*, 944) was added dropwise. After 10 min the cooling bath was removed and the reaction mixture was stirred at ambient temperature for 1.5 h. The mixture was poured onto water and extracted with hexanes and the extracts were dried over sodium sulfate and evaporated. The crude product was distilled (0.2 mm, 110–130° C.) to afford 7.8 g of tributyl (isopropoxymethyl)tin as a colorless liquid.

Step D: Preparation of Compound CXXV.

To a −78° C. solution of 719 mg of tributyl (isopropoxymethyl)tin and 0.4 ml of TMEDA in 4 mL of anhydrous THF was added 0.53 ml of 2.5M butyllithium in hexane. After 5 min, 100 mg of XXIV was added in a single portion, and the stirred suspension was allowed to stir at −78° for 45 min. The cold reaction mixture was quenched by the addition of aqueous ammonium chloride, and then extracted with ethyl acetate. The extracts were washed with brine, dried over sodium sulfate, and evaporated to an oily solid. The crude solid was purified by flash chromatography (50% EtOAc/hexanes eluent) and then preparative tlc (50% EtOAc/hexanes eluent) to give 2 mg of CXXV [ms, $(m+H)^+ = 389.0$]

Example 55

Compound CXXVI

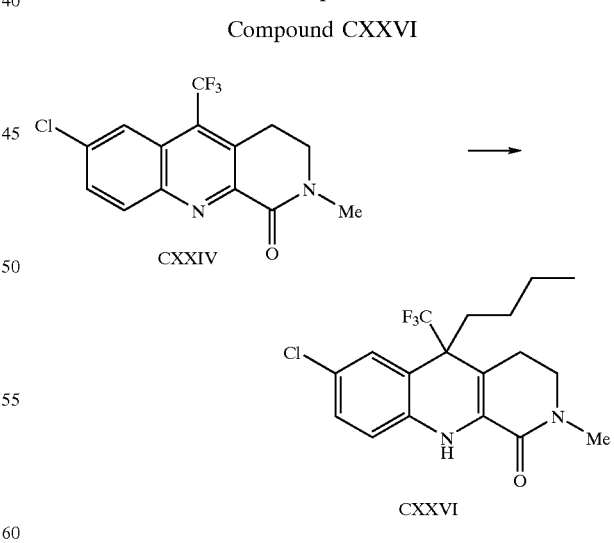

To a −78° C. mixture of 225 mg of CXXIV in 20 mL of dry THF and 2 mL of TMEDA was added dropwise 1.22 mL of 2.5 M butyllithium and the mixture was stirred 30 min at −78° C. The cold reaction mixture was quenched by the addition of aqueous ammonium chloride, and then extracted with ethyl acetate. The extracts were washed with 1N HCl, water, brine, dried over sodium sulfate, and evaporated to an oil that was purified by flash chromatography (10–20% EtOAc/hexanes eluent) and preparative tlc (50% EtOAc/hexanes eluent) to give 7 mg of CXVII as a crystalline solid (mp 221–223° C.).

Example 56

Compound CXXVII

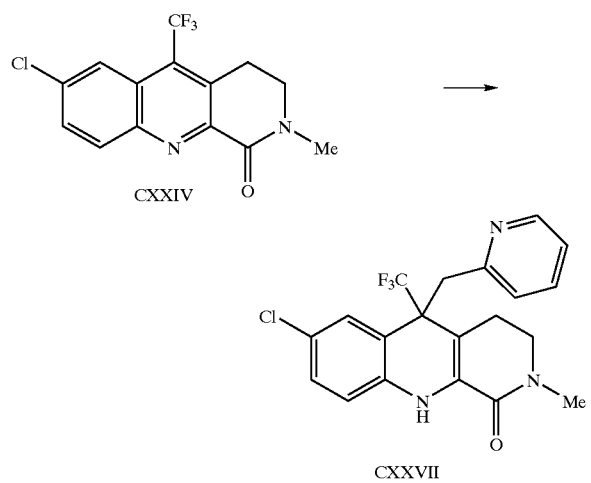

To a –78° C. solution of 1.07 mL of diisopropylamine in 10 mL of dry THF was added dropwise 3.1 mL of 2.5 M butyllithium. After 15 min, 0.755 mL of 2-methylpyridine was added, andthe mixture was stirred 20 min at –78° C. 600 mg of CXXIV was added, and after 30 min, the cold reaction mixture was quenched by the addition of aqueous ammonium chloride, and then extracted with ethyl acetate. The extracts were washed with 0.1N HCl, water, brine, dried over sodium sulfate, and evaporated to an oil that was purified by flash chromatography (50% EtOAc/hexanes then 5% MeOH/CH$_2$Cl$_2$ eluent) and preparative tlc (5% MeOH/CH$_2$Cl$_2$ eluent)) to give after recrystallization from methylene chloride/hexanes 60 mg of CXXVII as a crystalline solid (mp 192–193° C.).

Example 57

Compound CXXX

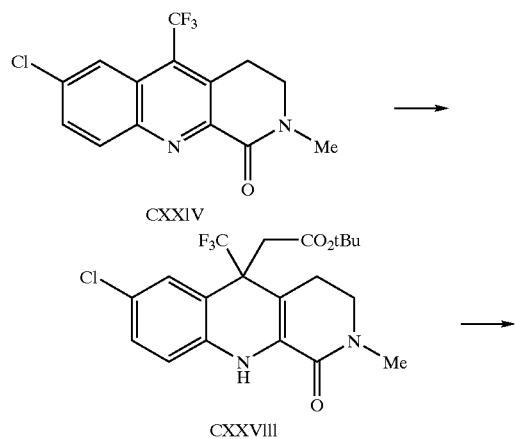

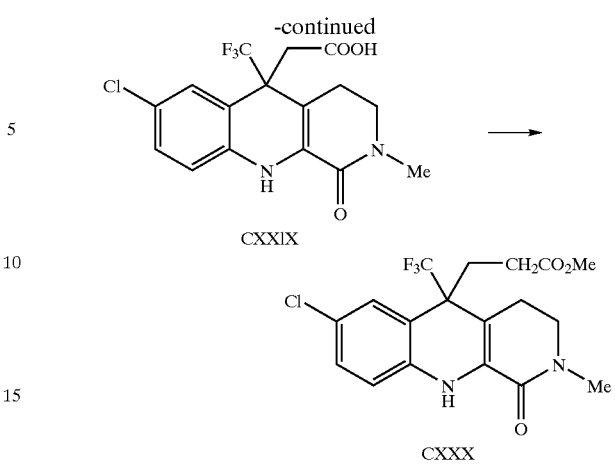

Step A: Preparation of Compound CXXVIII.

To a –78° C. solution of 0.45 mL ofdiisopropylamine in 10 mL of dry THF was added dropwise 0.90 mL of 1.6 M butyllithium. After 15 min, 0.45 mL of tert-butylacetate was added dropwise, and the mixture was stirred 30 min at –78° C. then allowed to warm to 0° C. The reaction mixture was again cooled to –78° C., 315 mg of CXXIV dissolved in 8 mL of THF was added dropwise, and it was stirred 30 min at –78° C. and 30 min at 0° C. The cold reaction mixture was quenched by the addition of aqueous ammonium chloride, and then extracted with ethyl acetate. The extracts were washed with water and brine, dried over sodium sulfate, and evaporated to 400 mg of CXXVIII as a pure solid.

Step B: Preparation of CXXIX.

A mixture of 183 mg of CXXVIII, 12 ml of methylene chloride, and 4.0 mL of trifluoroacetic acid was stirred for 1 h at 50° C. The cooled reaction mixture was poured onto water and extracted with methylene chloride. After drying over sodium sulfate, the extracts were evaporated to give 183 mg of CXXIX as a pure solid.

Step C: Preparation of CXXX.

A solution of 30 mg of CXXIX, 0.100 mL of thionyl chloride, and 2.0 mL of methanol was stirred overnight at room temperature. The reaction mixture was diluted with ethyl acetate, washed with water and brine, dried over sodium sulfate and evaporated to a crude product. This was purified by preparative tlc (50% EtOAc/hexanes eluent) to give after recrystallization from ether/hexanes 15 mg of CXXX as a crystalline solid (mp 200–201° C.).

Example 58

Compound CXXXI

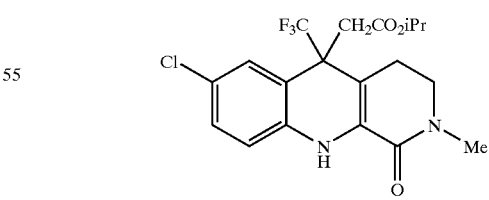

A mixture of 50 mg of CXXIX, 5 mL of isopropanol and 20 drops of sulfuric acid was refluxed overnight. The reaction mixture was poured onto water and extracted with ethyl acetate. The extracts were washed with aqueous sodium bicarbonate, dried and evaporated to an oil. This was purified by flash chromatogeaphy (25% EtOAc/hexanes eluent) to give a solid that was recrystallized from ether/hexanes to give 24 mg of CXXXI as a crystalline solid imp 153–154° C.).

Example 59

Compound CXXXIX

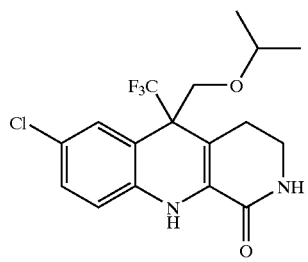

To a −78° C. solution of 719 mg of tributyl(isopropoxymethyl)tin and 0.4 ml of TMEDA in 4 mL of anhydrous THF was added 0.53 ml of 2.5M butyllithium in hexane. After 5 min, 100 mg of CV was added in a single portion, and the stirred suspension was allowed to warm to −20° C. over 35 min. The cold reaction mixture was quenched by the addition of aqueous ammonium chloride, and then extracted with ethyl acetate. The extracts were washed with brine, dried over sodium sulfate, and evaporated to an oily solid that was triturated with hexane to remove the tetraalkyltin byproduct. The crude solid was purified by flash chromatography (50% EtOAc/hexanes eluent) and then preparative tlc (67% EtOAc/hexanes eluent) to give after crystallization (ether/hexanes) 13 mg of CXXXIX (mp 163–164° C.)

Example 60

Compound CXL

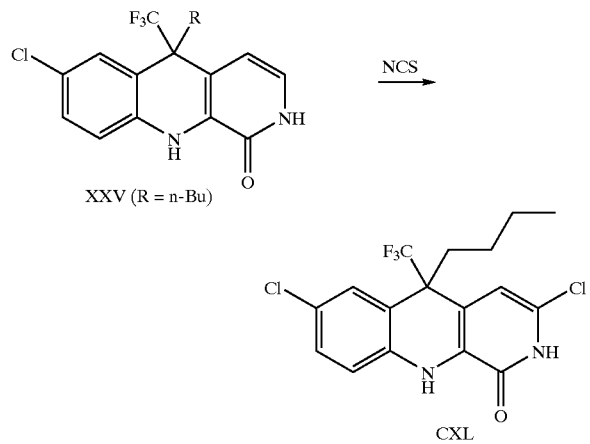

To a 0° C. solution of XXV (R=n-butyl) in 4 mL of dry acetonitrile was added 60 mg of N-chlorosuccinimide. After 30 min the cooling bath was removed and the reaction mixture was stirred at ambient temperature for 1.5 h. The mixture was diluted with ethyl acetate, washed twice with water and once with brine, dried over sodium sulfate and evaporated to give after crystallization from ether/hexanes 48 mg of CXL as pure crystals (mp 234–236° C.).

Example 61

Compound CXLIII

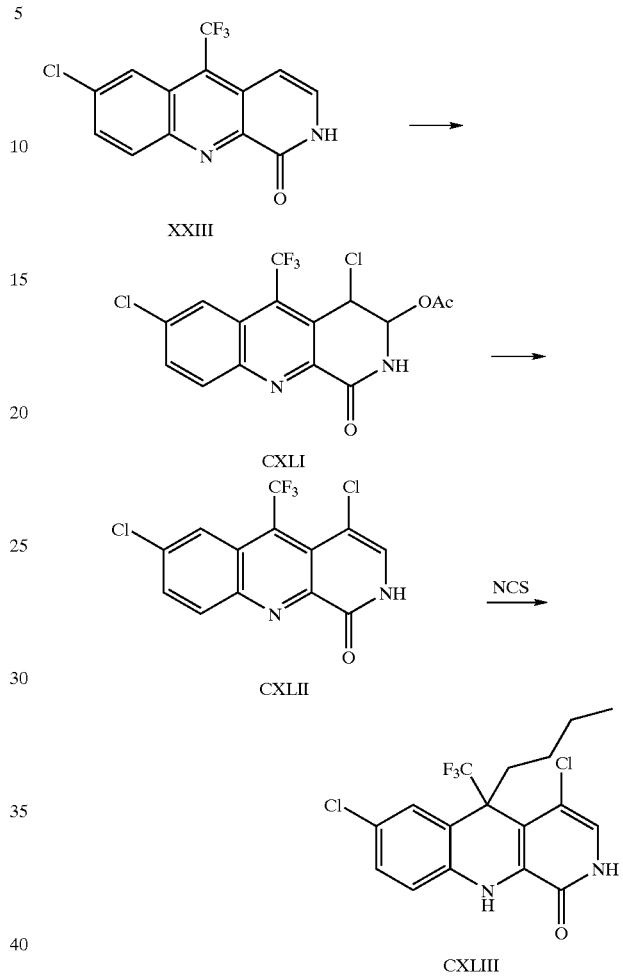

Step A: Preparation of CXLII.

A mixture of 200 mg of XXIII, and 105 mg of N-chlorosuccinimide in 20 ml of acetic acid was refluxed for 1 h. The solvent was evaporated and the crude reaction product was dissolved in ethyl acetate and this solution was washed twice with water and once with brine, dried over sodium sulfate and evaporated to give the intermediate solid addition product CXLI. This material was heated neat at 130–140° C. for 3 h to give 125 mg of CXLII as bright yellow crystals.

Step B: Preparation of CXLIII.

To a −78° C. mixture of 100 mg of CXLII in 10 mL of dry THF and 1 mL of TMEDA was added dropwise 1.5 mL of 1.6 M butyllithium and the mixture was stirred 30 min at −78° C. The cold reaction mixture was quenched by the addition of aqueous citric acid, and then extracted with ethyl acetate. The extracts were washed with water and brine, dried over sodium sulfate, and evaporated to crude product that was purified by flash chromatography (25–50% EtOAc/hexanes eluent) to give after crystallization from ether 11 mg of CXLIII as a crystalline solid (mp 252–255° C.).

Example 62

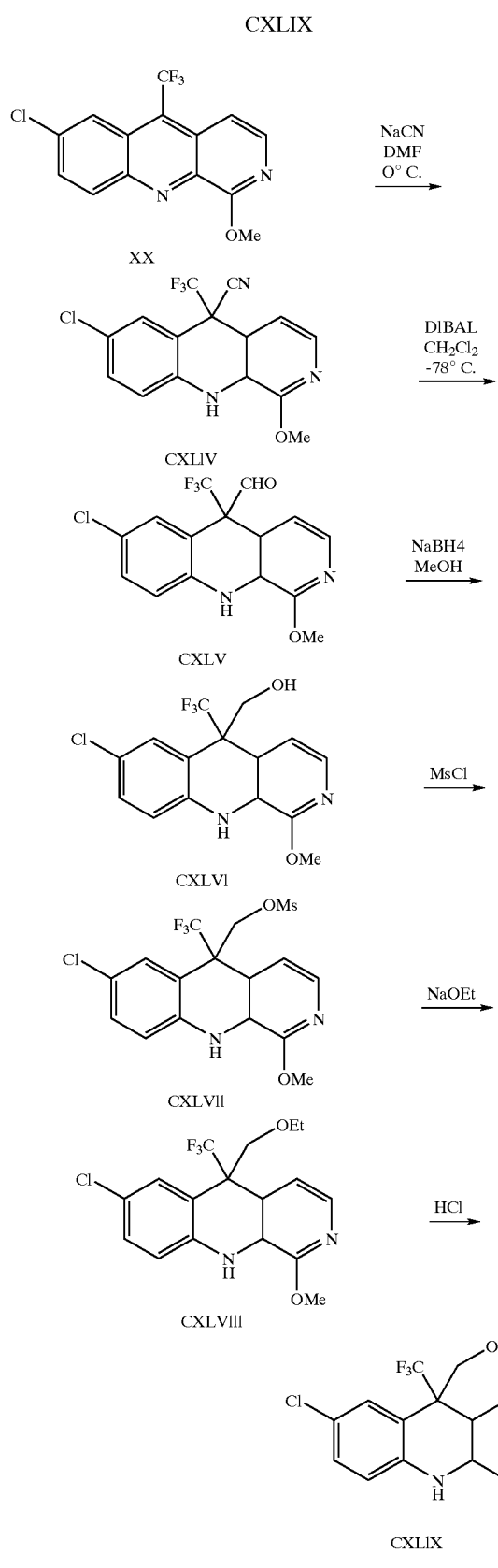

Step A: Preparation of CXLIV

To a 0° C. suspension of XX (700 mg, 1.7 mmol) in DMF (70 mL) was added NaCN (167 mg, 3.4 mmol). After stirring overnight, the reaction was diluted with EtOAc and washed with salturated NaHCO$_3$, water and brine. Concentration gave a brown solid (CXLIV, 800 mg).

Step B: Preparation of CXLV

To −78° C. solution of CXLIV (800 mg) in dichloromethane (35 mL) was added a solution of 1 M DIBAL in dichloromethane (3.8 mL). The reaction was quenched with 3 N HCl and diluted with EtOAc, washed with 3 N HCl (3×), saturated NaHCO$_3$ and brine. The organic phase was dried over Na$_2$SO$_4$ and concentrated to a pale orange solid (CXLV, 750 mg).

Step C: Preparation of CXLVI

A suspension of CXLV (750 mg) and NaBH$_4$ (140 mg) in MeOH (7 mL) was stirred for 15 min. The reaction was diluted with EtOAc, washed with water (2×) and brine. The organic phase was dried over Na$_2$SO$_4$ and concentrated to a pale orange solid which was triturated with ether to give CXLVI (570 mg).

Step D: Preparation of CXLVII

To a 0° C. solution of CXLVI (330 mg) and DIEA (0.95 mL) in DMF (4 mL) was added MsCl (0.21 mL). The reaction was diluted with EtOAc, washed with dilute HCl (2×), salturated NaHCO$_3$ and brine. The organic phase was dried over Na$_2$SO$_4$ and concentrated to an orange thick oil (CXLVII, 480 mg).

Step E: Preparation of CXLVIII

A solution of CXLVII (415 mg) in EtOH (100 mL) and 21% NaOEt in EtOH (150 mL) was stirred for 3 days. The reaction was diluted with EtOAc, washed with water (2×) and brine. The organic phase was concentrated and chromatographied to give an orange oil (CXLVIII, 73 mg).

Step F: Preparation of CXLIX

A solution of CXLVIII (70 mg) in EtOH (8 mL) and concentrated HCl (4 mL) was refluxed for 1 h. The reaction was diluted with EtOAc and neutralized with KOH, and washed with brine. The organic phase was dried over Na$_2$SO$_4$ and triturated with ether to give a brown solid (CXLIX 46 mg), M.P. 240–245° C.

Example 61a

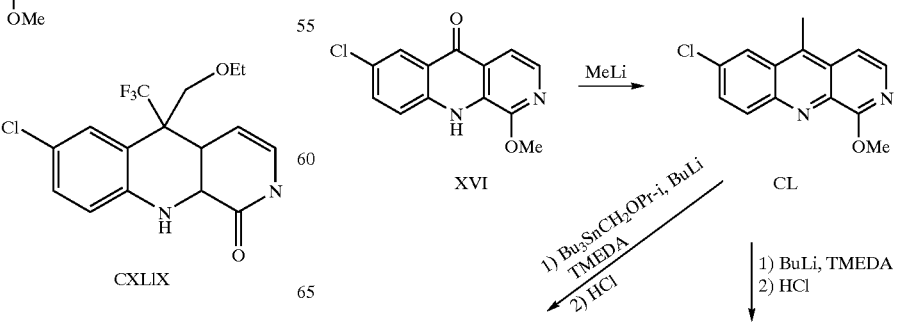

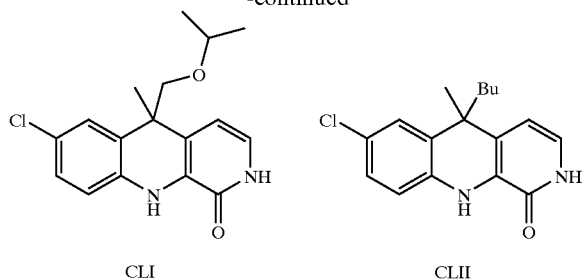

CLI

CLII

Step A:

To a 0° C. suspension of XVI (1.1 g, 4.2 mmol) in THF (10 mL) was added a solution of 1.4 M MeLi in ether (6.6 mL, 9.3 mmol). After stirred for 10 min., the reaction was quenched with sat. NH$_4$Cl. Partitioned between EtOAc and sat. NH$_4$Cl and washed with brine. The organic phase was dried over Na$_2$SO$_4$ and concentrated to give 0.97 g of yellow solid (CL, 88% yield).

Step B:

To a −78° C. solution of CL (100 mg, 0.39 mmol) in THF (1 mL) and TMEDA (0.1 mL) was added a solution of 1.6 M BuLi in hexanes (0.73 mL, 1.16 mmol). The reaction was allowed to warm to 0° C., then quenched with sat. NH$_4$Cl. Partitioned between EtOAc and sat. NH$_4$Cl and washed with brine. The organic phase was dried over Na$_2$SO$_4$ and concentrated. Flash chromatography (15% EtOAc/hexanes) gave 41 mg of an orange oil.

Demethylation: The oil (41 mg) was refluxed in conc. HCl (1 Ml) and EtOH (3 ml) FOR 1 h. The reaction was diluted with EtOAc, washed with 10% NaOH, then water and brine. The organic phase was dried over Na$_2$SO$_4$ and concentrated. Crystallization from ether/hexanes gave 24 mg of brown solid (CLII).

Example 62a

The compound CLI was prepared as described from CLII.

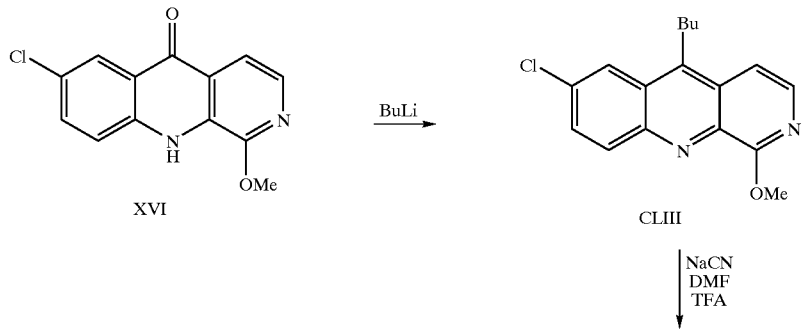

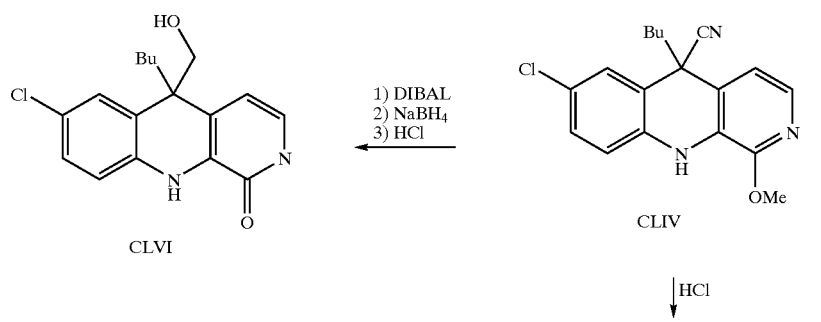

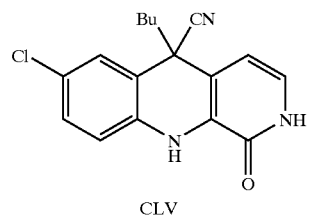

CLV

Step A:

CLIII was prepared as described in Compound CL.

Step B:

A suspension of CLIII (408 mg, 1.36 mmol) and NaCN (124 mg, 2.04 mmol) in DMF (4.5 mL) and TFA (0.11 mL, 1.36 mmol) was stirred overnight. The reaction was diluted with EtOAc, washed with saturated NaHCO$_3$, then water and brine. The organic phase was dried over Na$_2$SO$_4$ and concentrated. Flash chromatography (25% EtOAc/hexanes) gave 390 mg of solid (CLIV, 88% yield).

Step C:

CLIV was treated with HCl to give CLV as described in Compound CLII.

Example 64

The compound CLIV (200 mg) was treated with DIBAL in methylene chloride at −78° C. to give an orange oil (187 mg, 93%) after 3 N HCl/EtOAc workup. The aldehyde was reduced to the alcohol with NaBH$_4$ in MeOH in nearly quantitative yield. The demethylation was as described in Compound CLII to give CLVI.

Example 65

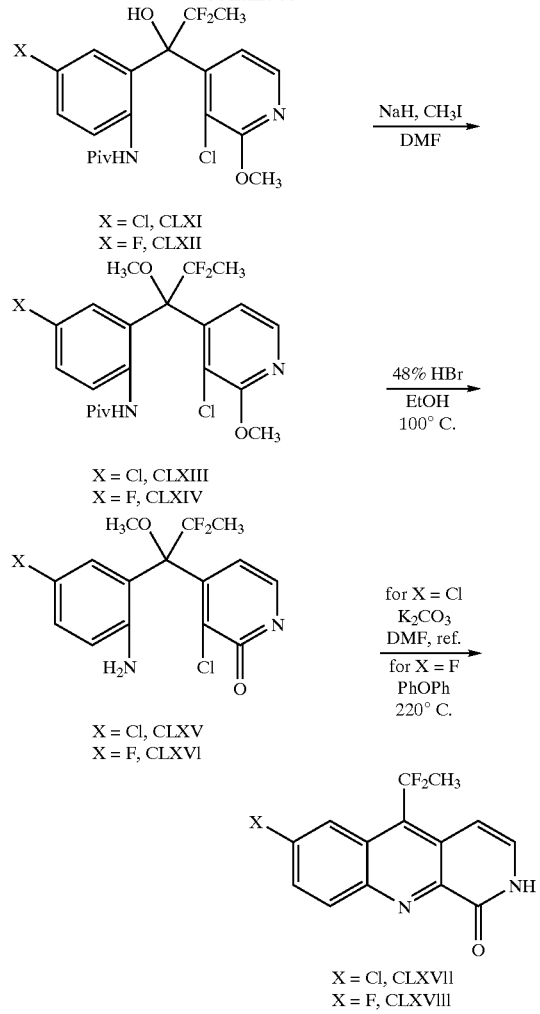

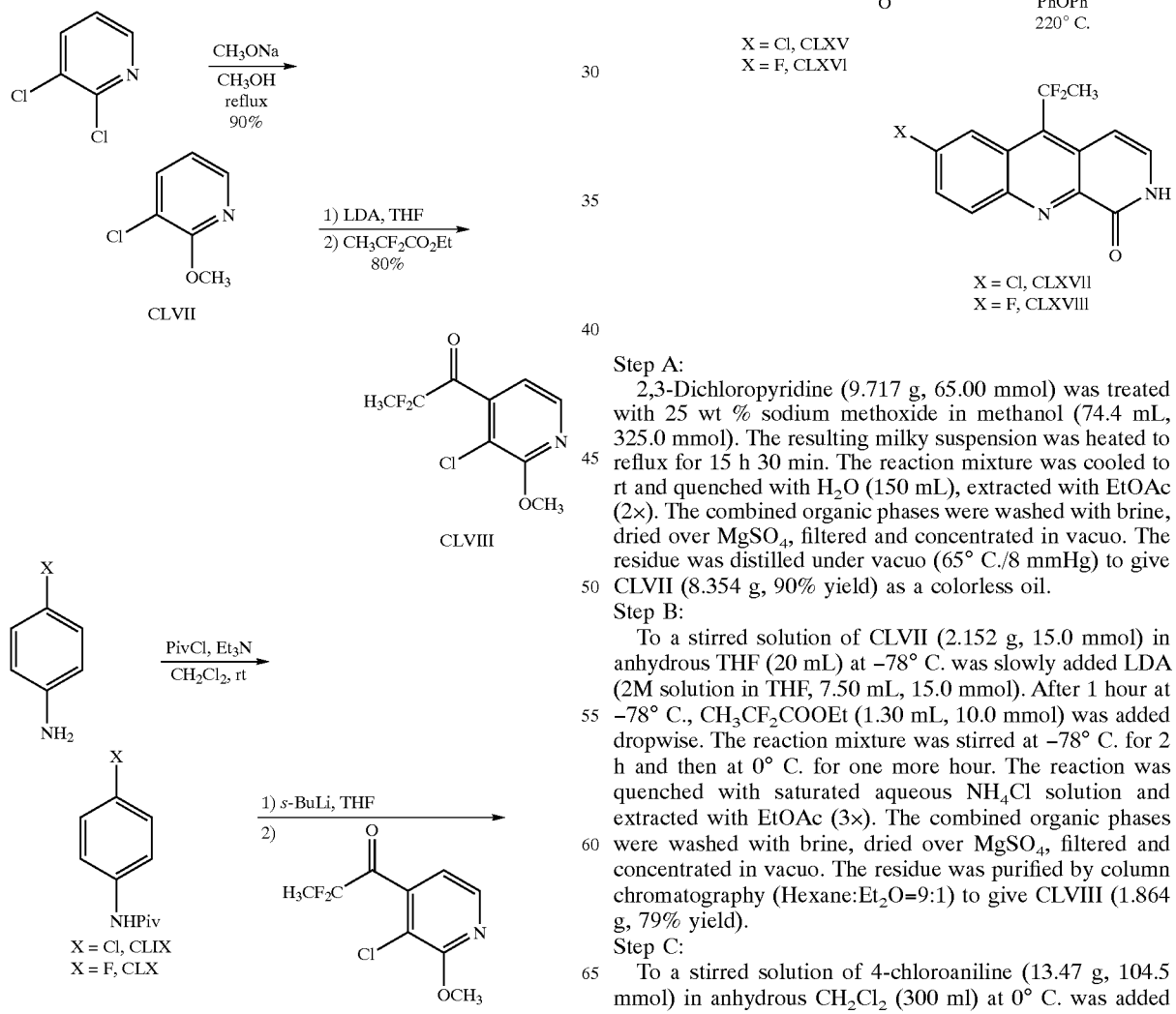

Step A:

2,3-Dichloropyridine (9.717 g, 65.00 mmol) was treated with 25 wt % sodium methoxide in methanol (74.4 mL, 325.0 mmol). The resulting milky suspension was heated to reflux for 15 h 30 min. The reaction mixture was cooled to rt and quenched with H$_2$O (150 mL), extracted with EtOAc (2×). The combined organic phases were washed with brine, dried over MgSO$_4$, filtered and concentrated in vacuo. The residue was distilled under vacuo (65° C./8 mmHg) to give CLVII (8.354 g, 90% yield) as a colorless oil.

Step B:

To a stirred solution of CLVII (2.152 g, 15.0 mmol) in anhydrous THF (20 mL) at −78° C. was slowly added LDA (2M solution in THF, 7.50 mL, 15.0 mmol). After 1 hour at −78° C., CH$_3$CF$_2$COOEt (1.30 mL, 10.0 mmol) was added dropwise. The reaction mixture was stirred at −78° C. for 2 h and then at 0° C. for one more hour. The reaction was quenched with saturated aqueous NH$_4$Cl solution and extracted with EtOAc (3×). The combined organic phases were washed with brine, dried over MgSO$_4$, filtered and concentrated in vacuo. The residue was purified by column chromatography (Hexane:Et$_2$O=9:1) to give CLVIII (1.864 g, 79% yield).

Step C:

To a stirred solution of 4-chloroaniline (13.47 g, 104.5 mmol) in anhydrous CH$_2$Cl$_2$ (300 ml) at 0° C. was added triethylamine (21.85 mL, 156.8 mmol) and pivaloyl chloride (15.60 mL, 125.4 mmol). The reaction mixture was stirred at rt for 1.5 h. The reaction was quenched with 1N HCl (150 mL) and extracted with CH$_2$Cl$_2$ (2×). The combined organic layers were washed with saturated aqueous NaHCO$_3$, brine, dried over anhydrous MgSO$_4$, filtered and concentrated in vacuo. The off-white solid was suspended in hexanes (100 mL) and stirred at rt for 10 min. The product was filtered and dried under vacuum to give CLIX (21.687 g, 98% yield) as a white solid, m.p. 149–150° C.

Step D:

To a stirred solution of 4-fluoroaniline (10.0 mL, 0.104 mol) in anhydrous CH$_2$Cl$_2$ (300 ml) at 0° C. was added triethylamine (21.9 mL, 0.157 mmol) and pivaloyl chloride (15.6 mL, 0.125 mmol). After 3 h at rt, the reaction mixture was quenched with 1N HCl (250 mL) and extracted with CH$_2$Cl$_2$ (3×200 mL). The combined organic layers were washed with saturated aqueous NaHCO$_3$, brine, dried over anhydrous MgSO$_4$, filtered and concentrated in vacuo to give white needle crystal. The crystal was rinsed with hexane and dried under vacuum to give CLX (19.4 g, 96% yield) as a white crystal.

Step E:

To a stirred solution of 4-Chloro-N-pivaloylaniline CLIX (3.36 g, 15.9 mmol) in anhydrous THF (60 mL) −78° C. was added sec-BuLi (1.3 M in hexane, 25 mL, 31.8 mmol) dropwise. After 2 h at 0° C., the reaction mixture was re-cooled to −78° C. and a solution of compound CLVIII (3.12 g, 13.24 mmol) in THF (20 mL) was added dropwise. The reaction mixture was warmed to −20° C. to −30° C. and stirred for 2.5 h. The reaction was quenched with saturated aqueous NH$_4$Cl solution and extracted with ethyl acetate. The organic phase was washed with brine, dried over MgSO$_4$, filtered and concentrated in vacuo. Flash chromatography purification gave CLXI (4.14 g, 70% yield) as a white solid.

Step F:

To a stirred solution of 4-fluoro-N-pivaloylaniline CLX (730 mg, 3.74 mmol) in anhydrous THF (15 mL) at −78° C. was added sec-BuLi (1.3M in Hexane, 5.75 mL, 7.48 mmol). After 1.5 h at 0° C., the reaction mixture was re-cooled to −78° C. and a solution of compound CLVIII (734 mg, 3.10 mmol) in THF (3 mL) was added dropwise. The reaction mixture was stirred at −78° C. for 1 h and then stirred between −20° C. and −30° C. for 1 h. The reaction was quenched with saturated aqueous NH$_4$Cl solution and extracted with ethyl acetate (3×60 mL). The combined organic phases were washed with brine, dried over MgSO$_4$, filtered and concentrated in vacuo. Flash chromatography purification gave CLXII (1.864 g, 67% yield) as a white solid.

Step G:

To a stirred solution of CLXI (4.134 g, 9.24 mmol) in anhydrous DMF (100 mL) at 0° C. was added NaH (60% in mineral oil, 450 mg, 11.25 mmol) in 3 portions. The resulting suspension was stirred for 10 min and MeI (750 μg, 11.8 mmol) was added. After 2 h at rt, another portion of NaH (25 mg, 0.625 mmol) and MeI (0.55 mmol) was added. After stirring for 45 minutes at rt, the reaction was quenched with saturated aqueous NH$_4$Cl and extracted with ethyl acetate (2×). The combined organic phases were washed with brine, dried over MgSO$_4$, filtered and concentrated to give a white solid. The solid was triturated with hexane, filtered to give CLXIII (4.156 g, 98% yield) as a white solid.

Step H:

To a stirred solution of CLXII (1.846 g, 4.3 mmol) in anhydrous DMF (25 mL) at 0° C. was added NaH (60% in mineral oil, 225 mg, 5.57 mmol). The resulting suspension was stirred for 10 min and MeI (410 μL, 6.45 mmol) was added. The reaction mixture was stirred at 0° C. for 2 h and then at rt for another 1.5 h. The reaction was quenched with water (50 mL) and extracted with ethyl acetate (3×100 mL). The combined organic phases were washed with brine, dried over MgSO$_4$, filtered and concentrated. The residue was purified by column chromatography (Hexane:EtOAc=6:1) to give CLXIV (1.72 g, 99% yield) as a pale solid.

Step J:

To a stirred solution of CLXIII (4.156 g, 9 mmol) in ethanol (20 mL) was added HBr (48% aqueous solution, 40 mL 360 mmol). The reaction mixture was heated at 100° C. for 48 h. The mixture was cooled to 0° C. and neutralized carefully with concentrated NaOH (50% wt) and saturated aqueous Na$_2$CO$_3$ to pH 8–9, extracted with ethyl acetate. The organic phase was washed with brine, dried over MgSO$_4$, filtered and concentrated to give a light yellow solid. The solid was triturated with ether and filtered to give CLXV (3.2 g, 98% yield).

Step K:

To a stirred solution of CLXIV (445 mg, 1.0 mmol) in ethanol (6 mL) was added HBr (48% solution in H$_2$O, 3.4 mL, 30 mmol). The reaction mixture was heated at 100° C. for 48 h. The mixture was cooled to 0° C. and neutralized carefully with concentrated NaOH (50% wt) and saturated aqueous Na$_2$CO$_3$ to pH 8–9, extracted with ethyl acetate (3×). The combined organic phases were washed with brine, dried over MgSO$_4$, filtered and concentrated to give a white solid. The solid was rinsed with ether and filter to give CLXVI (307 mg, 88% yield).

Step L:

To a stirred solution of CLXV (187 mg, 0.515 mmol) in dry DMF (25 ml) was added K$_2$CO$_3$ (142 mg, 1.03 mmol). The reaction mixture was heated to reflux for 3 h. The reaction mixture was cooled to rt and quenched with H$_2$O (20 mL). The solid was filtered, washed with water and hexane, dried under vacuum to give CLXVII (150 mg, 99% yield) as a brown solid.

Step M:

A suspension of CLXVI (690 mg, 2 mmol) in diphenyl ether (5 mL) was heated at 225° C. for 1.5 h. The reaction mixture was cooled to rt and diluted with ether. The black solid precipitated and was filtered to give CLXVIII (527 mg, 95%) as the crude product.

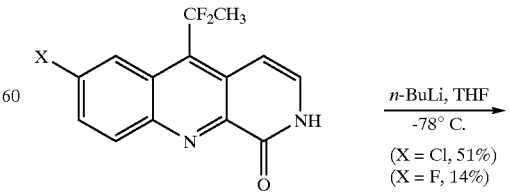

CLXIX: X = Cl
CLXX: X = F

-continued

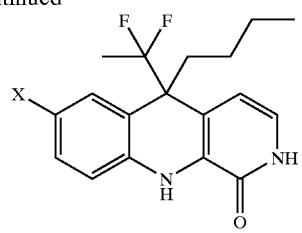

CLXXI: X = Cl
CLXXII: X = F

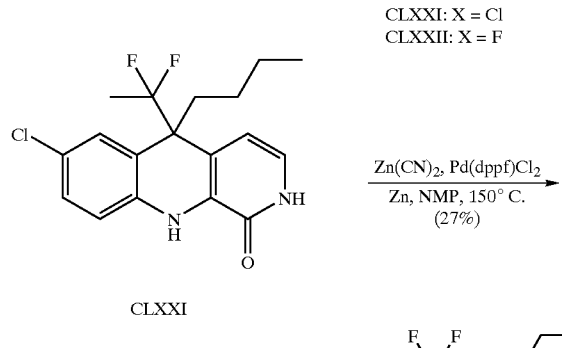

CLXXI

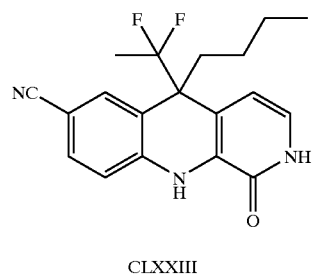

CLXXIII

Step N:

To a stirred suspension of compound CLXIX (87 mg, 0.295 mmol) in anhydrous THF (5 mL) at −78° C. was slowly added n-BuLi (2.5 M in hexane, 1.18 mL, 2.95 mmol). The resulting brown solution was stirred at −78° C. for 3 h 30 min. The reaction was quenched with water (20 mL) and extracted with ethyl acetate (2×). The combined organic layers were washed with brine, dried over MgSO$_4$, filtered and concentrated. The residue was purified by column chromatography (EtOAc:Hexane=3:2) to give CLXXI (53 mg, 51% yield) as a pale yellow solid, m.p. 120–122° C., MS (ES): (M+H)$^+$=353.3, (M−H)$^−$=351.2.

Example 66

Step O:

To a stirred suspension of compound CLXX (95 mg, crude) in anhydrous THF (6 mL) at −78° C. was slowly added n-BuLi (1.6 M in hexane, 1.5 mL, 2.4 mmol). The reaction mixture was stirred at −78° C. for 30 min. The reaction was quenched with saturated aqueous NH$_4$Cl and extracted with ethyl acetate (3×50 mL). The combined ethyl acetate layers were washed with brine, dried over MgSO$_4$, filtered and concentrated. The residue was purified by flash column (CH$_2$Cl$_2$:MeOH=100:4) to give CLXXII (16 mg, 14% yield) as a white solid, m.p. 267–270° C., MS (ES): (M+H)$^+$=337.3, (M−H)$^−$=335.3.

Example 67

Step P:

A degassed mixture of CLXXI (105 mg, 0.298 mmol), Zn(CN)$_2$ (72 mg, 0.595 mmol), {Dichloro[1,1'-Bis (diphenylphosphino)ferrocene]Palladium(II) dichloromethane adduct} (98 mg, 0.12 mmol) and Zn powder (24 mg, 0.36 mmol) in 1-methyl-2-pyrrolidinone (3 mL) was heated at 150° C. for 48 h. The reaction mixture was cooled to rt, diluted with ethyl acetate, filtered through a pad of Celite and washed with ethyl acetate. The filtrate was washed with 2N NH$_4$OH, brine, dried over MgSO$_4$, filtered and concentrated. The residue was purified by flash column chromatography (EtOAc:Hexane:AcCN=7:20:3) to give CLXXIII (28 mg, 27% yield) as a light yellow solid. m.p. 132.2–134.7° C., MS (ES): (M+H)$^+$=344.3, (M−H)$^−$=342.3.

Example 68

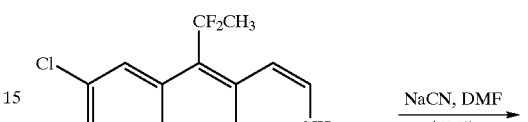

CLXIX

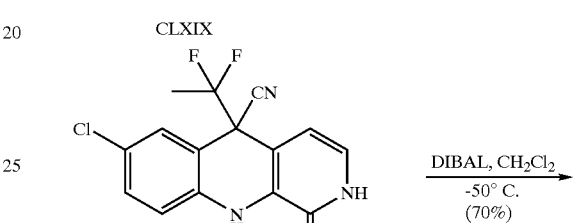

CLXXIV

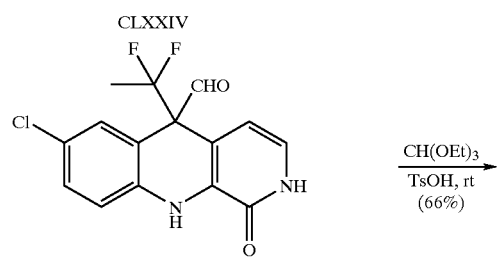

CLXXV

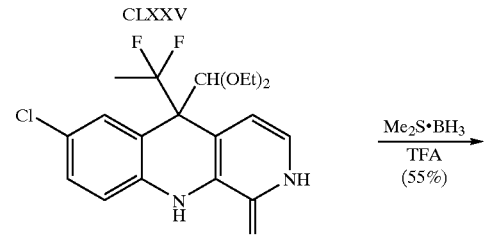

CLXXVI

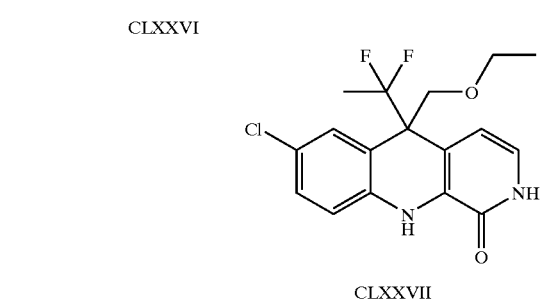

CLXXVII

Step A:

To a solution of compound CLXIX (694 mg, 2.355 mmol) in anhydrous DMF (15 mL) was added NaCN (258 mg, 5.0 mmol). The reaction mixture was stirred at room temperature overnight. The reaction mixture was filtered through a pad of Celite and washed with CH$_2$Cl$_2$. 100 mL of H$_2$O was added to the filtrate and the mixture was extracted with CH$_2$Cl$_2$ (3×150 mL). The combined organic layers were washed with saturated aqueous NaHCO$_3$, brine and dried over MgSO$_4$, filtered and concentrated. The residue was purified by column chromatography (CH$_2$Cl$_2$:MeOH= 100:4) to give CLXXIV (520 mg, 68% yield).

Step B:

To a stirred solution of CLXXIV (518 mg, 1.61 mmol) in anhydrous CH$_2$Cl$_2$ (20 mL) at −78° C. was added slowly DIBAL (1 M in CH$_2$Cl$_2$, 2.0 mL, 2.0 mmol). After 3 h at −50° C., another portion of 1 M (2.6 mL, 2.6 mmol) was added. The reaction mixture was stirred at at −50° C. for 2 h. The reaction was quenched with 1 N HCl (20 mL) and extracted with ethyl acetate (3×150 mL). The combined organic layers were washed by saturated aqueous NaHCO$_3$, brine and dried over MgSO$_4$, filtered and concentrated. The residue was crystallized in a small volume of ether to give CLXXV (364 mg, 70% yield) as a white crystal (70%).

Step C:

A solution of CLXXV (165 mg, 0.5 mmol), CH(OEt)$_3$ (5 mL, 29.5 mmol) and p-toluensulfonic acid monohydrate (245 mg, 1.29 mmol) was stirred at room temperature for 18 h. The reaction mixture was neutralized by 1 N NaOH and extracted with ethyl acetate. The organic layer was washed with brine and dried over MgSO$_4$, filtered and concentrated in vacuo. The residue was purified by column chromatography (EtOAc:Hexane=2:1) to give CLXXVI (131 mg, 66% yield).

Step D:

To a stirred solution of compound CLXXVI (130 mg, 0.326 mmol) in TFA (2.5 mL)/TFAA (0.08 ml) at 0° C. was added BH$_3$.Me$_2$S (10.0–10.2 M, 150 μL, 1.515 mmol) dropwise. After stirring at rt for 2 h, another portion of BH$_3$.Me$_2$S (10.0–10.2M, 120 μL, 1.21 mmol) was added dropwise. After stirring at room temperature for another 2 h, the solvent TFA was removed in vacuo. The residue was neutralized with 1 N NaOH and extracted with ethyl acetate (3×50 mL). The combined organic layers were washed with saturated aqueous NaHCO$_3$, brine and dried over MgSO$_4$, filtered and concentrated. The residue was dissolved in 3 mL of 4 N HCl in Dioxane and 3 mL of MeOH. The mixture was stirred at room temperature for 2 h to hydrolyze the formed B(OOCCF$_3$)$_3$. The mixture was then concentrated and extracted with ethyl acetate (3×50 mL). The combined organic layers were washed with 1 N NaOH, brine, dried over MgSO$_4$, filtered and concentrated. The residue was purified by column chromatography (CH$_2$Cl$_2$:MeOH 100:4) to give CLXXVII (64 mg, 55% yield). m.p. 265–267° C., MS (ES): (M+H)$^+$=355.3, (M−H)$^-$=353.3.

Examples 101, 111, 112 and 113 were prepared using the procedure described in Example 4.

Example 110

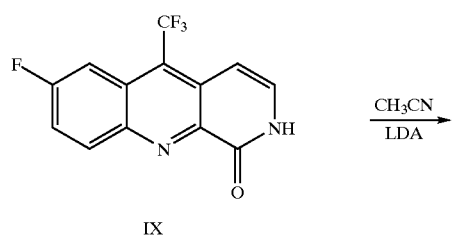

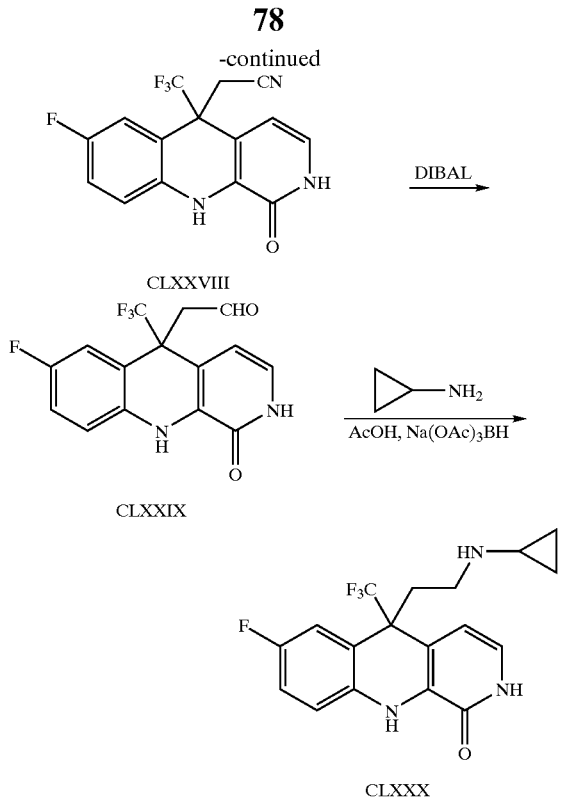

Step A:

0.37 ml of anhydrous acetonitrile was dissolved in 10 ml of anhydrous THF, and cooled to −78° C. 4.0 ml of 2M lithium diisopropylamide in heptane/THF/ethylbenzene was added. The mixture was allowed to stir at −78° C. for 20 minutes. Aromatic intermediate IX (500 mg) was added in one portion. The mixture was stirred an additional 1 hour at −78° C., and quenched with saturated aqueous ammonium chloride. Partitioning between EtOAc/water, drying over magnesium sulfate and concentration yielded a brown oil. Purification by flash chromatography (60% EtOAc/hexane, silica gel) gave 400 mg of CLXXVIII as a yellow solid. (70% yield)

Step B:

820 mg of nitrile CLXXVIII was dissolved in 6 ml of dichloromethane and cooled to −78° C. 7.3 ml (3 equivalents) of 1M diisobutylaluminum hydride in dichloromethane was added. The mixture was warmed to −30° C. over 2 hours. The mixture was quenched with 3N HCl and extracted with EtOAc. Drying over sodium sulfate and concentration yielded a yellow oil which after flash chromatography (60% EtOAc/hexane, silica gel) gave aldehyde CLXXIX. (605 mg, 73% yield)

Step C:

240 mg of aldehyde CLXXIX, 0.061 ml of cyclopropylamine (1.2 equivalents), 314 mg of sodium triacetoxyborohydride (2.0 equivalents) and 0.042 ml (1.0 equivalent) of acetic acid were combined in a flask and stirred 1 hour at 25° C. The mixture was partitioned between EtOAc/saturated aqueous sodium bicarbonate, dried over magnesium sulfate and concentrated. Flash chromatography (10% methanol/dichloromethane, silica gel) gave 145 mg of CLXXX as a yellow solid. (53% yield)

Examples 104–106, 108–109 and 119–120 were prepared using the procedure described in example 110.

Example 122

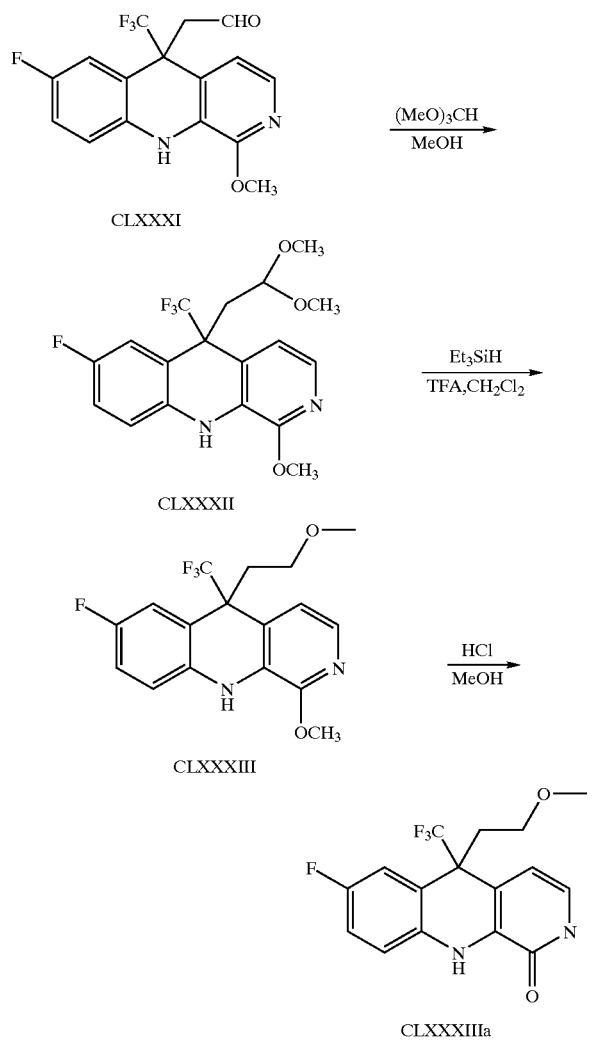

Examples 107 and 118 were prepared using the procedure described in example 122.

Examples 124, 126, 127–130, and 135 were prepared using the procedure described in example 30.

Example 123 was prepared using the procedure described in example 28.

Example 115

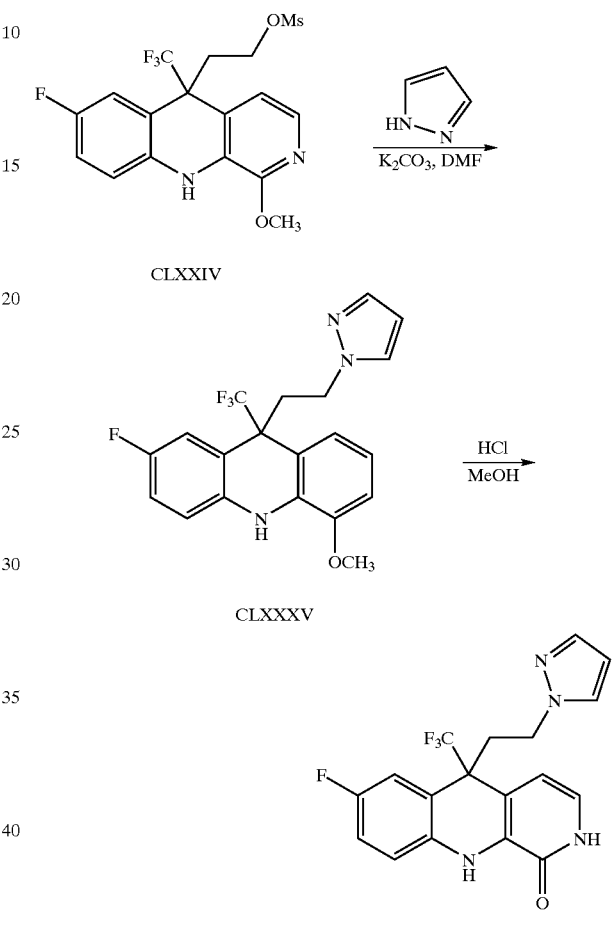

Step A:

Aldehyde CLXXXI (83 mg), trimethyl orthoformate (1 ml), and p-toluenesulfonic acid hydrate (91 mg, 2 equivalents), were dissolved in 2 ml methanol and ref luxed for 2 hours. The solution was cooled and concentrated to a yellow oil. Purification by flash chromatography (20% EtOAc/hexane, silica gel) yielded acetal CLXXXII as a clear oil, 87 mg. (93% yield)

Step B:

Compound CLXXXII was dissolved in 1 ml dichloromethane. I ml trifluoroacetic acid and 0.393 ml triethylsilane (10 equivalents) were added. The solution was stirred 1 hour at 25° C., then concentrated to a yellow oil. Purification by preparative TLC (20% EtOAc/hexane, silica gel) yielded compound CLXXXIII as a clear oil, 29 mg. (33% yield)

Step C:

Compound CLXXXIII (29 mg) was dissolved in 2 ml methanol. 0.5 ml concentrated HCl was added. The solution was heated to reflux for 1 hr, then cooled. It was partitioned between EtOAc/saturated aqueous sodium bicarbonate, washed once with water, dried over magnesium sulfate, and concentrated to a brown oil. Purification by preparative TLC (10% methanol/dichloromethane, silica gel) gave 12 mg of compound CLXXXIIIa as a brown solid. (43% yield)

Step A:

Compound CLXXXIV (75 mg), potassium carbonate (249 mg, 10 equivalents), and pyrazole (122 mg, 10 equivalents) were dissolved in 1 ml anhydrous DMF and heated to 100° C. 18 hours The mixture was cooled and partitioned between EtOAc/water, washed once with water and dried over magnesium sulfate. Purification by preparative TLC (30% EtOAc/hexane, silica gel) gave compound CLXXXV as a yellow oil. (36 mg, 51% yield)

Step B:

Compound CLXXXV (36 mg) was dissolved in 2 ml methanol. 1 ml concentrated HCl was added, and the solution was heated to reflux for 1 hr, then cooled. It was partitioned between EtOAc/saturated aqueous sodium bicarbonate, washed once with water, dried over magnesium sulfate, and concentrated to a yellow oil. Purification by preparative TLC (5% methanol/dichloromethane, silica gel) gave 23 mg of compound CLXXXVI as a white solid. (66% yield).

Examples 114 and 116 were prepared using the procedure described in example 115.

Examples 125, 131, 144 and 145 were prepared using the procedure described in example 28

Example 146

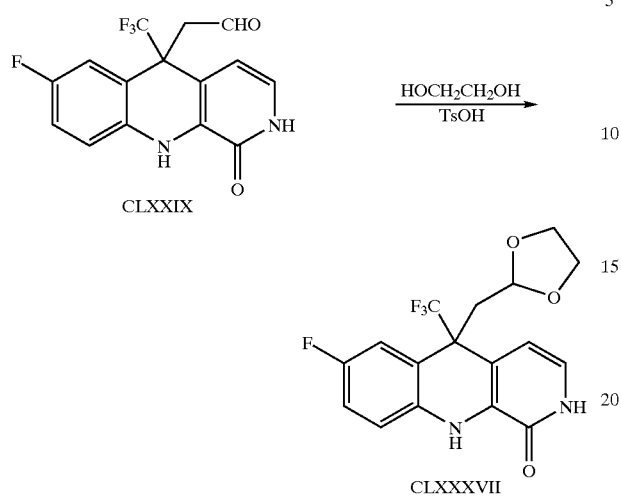

86 mg of aldehyde CLXXIX, 0.145 ml of ethylene glycol (10 equivalents), and 25 mg of p-toluenesulfonic acid hydrate (0.5 equivalents) were dissolved in 1.5 ml of benzene. The solution was heated to reflux 30 minutes, then cooled. It was partitioned between EtOAc/saturated aqueous sodium bicarbonate and washed once with water. The organic phase was reduced in volume on a rotary evaporator. The resulting white precipitate was filtered and washed with water and toluene to obtain pure compound CLXXXVII (70 mg, 73% yield).

Chiral HPLC separation was performed using chiral columns which gave the (R) and (S) enantiomers in >99% EE.

The following compounds have been made using the techniques described above.

TABLE 1*

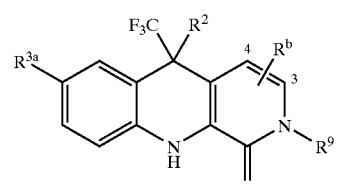

(I)

| Ex # | R$^b$ | R$^2$ | R$^{3a}$ | R$^9$ | Mass Spec | MP (° C.) |
|---|---|---|---|---|---|---|
| 1 | H | (6-methylpyrid-2-yl)methyl | F | H | | |
| 2 | H | Cyclopropylacetylenyl | F | H | | |
| 3 | H | n-Propyl | F | H | | |
| 4 | H | n-Butyl | F | H | | |
| 5 | H | 4-Fluorophenylmethyl | F | H | | |
| 6 | H | 2-Pyridylmethyl | F | H | | |
| 7 | H | i-Propyl | F | H | | |
| 8 | H | 3-Pyridylmethyl | F | H | | |
| 9 | H | 4-Pyridylmethyl | F | H | | |
| 10 | H | 3-Propynyl | F | H | | |
| 11 | H | 2-Pyridylethynyl | F | H | | |
| 12 | H | 2-(2-Pyridyl)ethyl | F | H | | |
| 13 | 3-Cl | n-Propyl | F | H | | |

TABLE 1*-continued

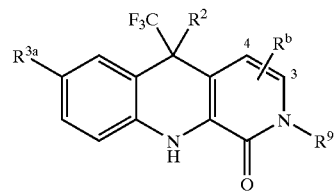

(I)

| Ex # | R$^b$ | R$^2$ | R$^{3a}$ | R$^9$ | Mass Spec | MP (° C.) |
|---|---|---|---|---|---|---|
| 14 | H | 3-Propenyl | F | H | | |
| 15 | H | 2-Cyclopropylethyl | F | H | | |
| 16 | H | Ethynyl | F | H | | |
| 17 | H | 2-Ethoxyethyl | F | H | | |
| 17a | H | 2-chloroethyl | F | H | | |
| 18 | H | n-Butyl | Cl | H | | 245–248 |
| 19 | H | 2-Pyridylmethyl | Cl | H | | 270–275 |
| 20 | H | 2-Cyclopropylethyl | Cl | H | | 220–222 |
| 21 | H | Cyclopropylacetylenyl | Cl | H | | 247–250 |
| 22 | H | N-Cyclopropylaminomethyl | Cl | H | | 230–235 |
| 23 | H | Hydroxymethyl | Cl | H | | 270–275 |
| 24 | H | 2-Pyridylmethyl | Cl | CH$_3$ | | 166–168 |
| 25 | H | 2-Cyclopropylethyl | Cl | CH$_3$ | | 150–152 |
| 27 | H | n-Propoxymethyl | Cl | H | | 162–165 |
| 28 | H | i-Propoxymethyl | Cl | H | | 185–190 |
| 29 | H | Methoxyethyl | Cl | H | | 268–271 |
| 29a | H | diisopropoxymethyl | Cl | H | | |
| 30 | H | i-Propylaminomethyl | Cl | H | | 235–240 |
| 31 | H | N-Methyl-i-propylaminomethyl | Cl | H | | 105–110 |
| 32 | H | Cyclopropylaminomethyl | Cl | H | | 242–245 |
| 33 | H | n-Propylaminomethyl | Cl | H | | 243–245 |
| 34 | H | Cyclobutylaminomethyl | Cl | H | | 250–254 |
| 35 | H | i-Butylaminomethyl | Cl | H | | 210–215 |
| 36 | H | i-Propoxymethyl | Cl | H | | 195–197 |
| 37 | H | n-butyl | CN | H | | |
| 38 | H | i-propoxymethyl | CN | H | | |
| 39 | H | cyclopropylthiomethyl | Cl | H | | |
| 39a | H | cyclopropylsulfoxymethyl | Cl | H | | |
| 40 | H | i-propylsulfoxymethyl | Cl | H | | |
| 41 | H | t-butylsulfoxymethyl | Cl | H | | |
| 42 | H | methylthiomethyl | Cl | H | | |
| 43 | H | ethylthiomethyl | Cl | H | | |
| 44 | H | i-propylthiomethyl | Cl | H | | |
| 45 | H | i-propylthiomethyl | F | H | | |
| 46 | H | t-butylthiomethyl | Cl | H | | |
| 47 | H | cyclopropylmethoxymethyl | Cl | H | | |
| 48 | H | cyclobutoxymethyl | Cl | H | | |
| 49 | H | cyclobutoxymethyl | F | H | | |
| 50 | H | cyclopropylmethoxymethyl | F | H | | |
| 51 | 3-CH$_3$ | i-propoxymethyl | Cl | H | | |
| 52 | 3-CH$_3$ | n-butyl | Cl | H | | |
| 53 | 3-CH$_3$ | n-butyl | CN | H | | |
| 60 | 3-Cl | n-butyl | Cl | H | | |
| 61 | 4-Cl | n-butyl | Cl | H | | |
| 62 | H | ethoxyethyl | Cl | H | | 240–245 |
| 100 | H | allyl | F | H | | |
| 101 | H | 2-methyl-1-propenyl | F | H | 337.1 | |

TABLE 1*-continued

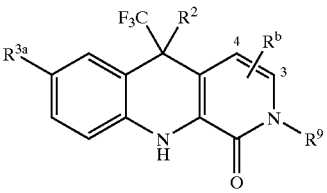

(I)

| Ex # | R$^b$ | R$^2$ | R$^{3a}$ | R$^9$ | Mass Spec | MP (° C.) |
|---|---|---|---|---|---|---|
| 102 | H | 1-propynyl | F | H | | |
| 103 | H | cyanomethyl | F | H | | |
| 104 | H | 2-(ethylamino)ethyl | F | H | 356.4 | |
| 105 | H | 2-(dimethylamino)ethyl | F | H | 356.4 | |
| 106 | H | 2-(methylamino)ethyl | F | H | 340.3 | |
| 107 | H | 2-ethoxyethyl | F | H | 355.3 | |
| 108 | H | 2-(i-propylamino)ethyl | F | H | 370.4 | |
| 109 | H | 2-(diethylamino)ethyl | F | H | 384.4 | |
| 110 | H | 2-(cyclopropylamino)ethyl | F | H | 366.3 | |
| 111 | H | pentyl | F | H | 353.4 | |
| 112 | H | i-butyl | F | H | 339.4 | |
| 113 | H | vinyl | F | H | 309.3 | |
| 114 | H | imidazolylethyl | F | H | 379.4 | |
| 115 | H | pyrazolylethyl | F | H | 379.3 | |
| 116 | H | 1,2,4-triazolylethyl | F | H | 378.3 | |
| 117 | H | i-propylaminomethyl | F | H | 356.4 | |
| 118 | H | 2-(i-propoxy)ethyl | F | H | 369.3 | |
| 119 | H | 2-(methylethylamino)ethyl | F | H | 370.4 | |
| 120 | H | 2-(i-propylmethylamino)ethyl | F | H | 384.4 | |
| 121 | H | 2-(pyrrolidinyl)ethyl | F | H | 382.4 | |
| 122 | H | 2-(methoxy)ethyl | F | H | 341.3 | |
| 123 | H | i-propoxymethyl | F | H | 357.1 | |
| 124 | H | 3-pentanylaminomethyl | F | H | 384.4 | |
| 125 | H | dimethoxymethyl | F | H | 357.3 | |
| 126 | H | i-butylaminomethyl | F | H | 370.4 | |
| 127 | H | cyclopropylmethyl aminomethyl | F | H | 368.3 | |
| 128 | H | allylaminomethyl | F | H | 354.3 | |
| 129 | H | (R)-sec-butylaminomethyl | F | H | 370.4 | |
| 130 | H | (S)-sec-butylaminomethyl | F | H | 370.3 | |
| 131 | H | diethoxymethyl | F | H | 387.3 | |
| 132 | 3-Cl | propyl | F | H | | |
| 133 | H | butyl | F | Me | 353.3 | |
| 134 | H | 2-(i-propoxy)ethyl | F | Me | 383.3 | |
| 135 | H | i-propylaminomethyl | F | Me | 370.4 | |
| 136 | H | i-propoxymethyl | F | Me | 371.1 | |
| 137 | H | 2-ethoxyethyl | F | Me | 371.1 | |
| 138 | H | sec-butylaminomethyl | F | Me | 384.4 | |
| 139 | H | cyclopentylaminomethyl | F | H | 382.1 | |
| 140 | H | cyclobutylaminomethyl | F | H | 368.3 | |
| 141 | H | dimethylaminomethyl | F | H | 342.3 | |
| 142 | H | pyrrolidinylmethyl | F | H | 368.3 | |
| 143 | H | cyclopropylaminomethyl | F | H | 354.3 | |
| 144 | H | 2-(dimethoxy)ethyl | F | H | 371.2 | |
| 145 | H | 2-(diethoxy)ethyl | F | H | 399.3 | |
| 146 | H | 2-(1,3-dioxolanyl)methyl | F | H | 369.2 | |
| 147 | H | 2-(methoxy)ethyl | F | CH$_3$ | 357.1 | |

*Unless otherwise noted, stereochemistry is (+/−).

TABLE 1A*

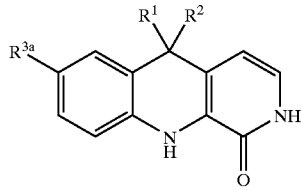

| Ex # | R$^{3a}$ | R$^1$ | R$^2$ | MP (° C.) |
|---|---|---|---|---|
| 61a | Cl | CH$_3$ | butyl | 177–179 |
| 62a | Cl | CH$_3$ | i-propoxymethyl | |
| 63 | Cl | CN | butyl | 182–185 |
| 64 | Cl | CH$_2$OH | butyl | 260–265 |
| 64a | Cl | CHF$_2$ | butyl | 198–200 |
| 64b | Cl | CHF$_2$ | i-propoxymethyl | 138–142 |
| 65 | Cl | CF$_2$CH$_3$ | n-butyl | |
| 66 | F | CF$_2$CH$_3$ | n-Butyl | |
| 67 | CN | CF$_2$CH$_3$ | n-butyl | |
| 68 | Cl | CF$_2$CH$_3$ | ethoxymethyl | |

*Unless otherwise noted, stereochemistry is (+/−).

The following compounds were prepared from the racemic mixtures using the procedure described above.

TABLE 1B

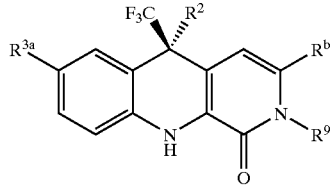

| Ex # | R$^{3a}$ | R$^9$ | R$^2$ | R$^b$ | MP (° C.) |
|---|---|---|---|---|---|
| 200 | F | H | 2-pyridylmethyl | H | |
| 201 | F | H | butyl | H | |
| 202 | Cl | H | 2-pyridylmethyl | H | |
| 203 | Cl | H | 2-cyclopropylethyl | H | |
| 204 | F | H | 2-(6-methyl)pyridylmethyl | H | |
| 205 | F | Me | butyl | H | |
| 206 | Cl | H | i-propoxymethyl | H | |
| 207 | Cl | H | i-propylaminomethyl | H | |
| 208 | Cl | H | cyclopropylaminomethyl | H | |
| 209 | Cl | Me | i-propoxymethyl | H | |
| 210 | F | H | i-propoxymethyl | H | |
| 211 | Cl | H | i-propylmethylaminomethyl | H | |
| 212 | Cl | H | 2-methoxyethyl | H | |
| 213 | Cl | H | cyclobutoxymethyl | H | |
| 214 | Cl | H | ethoxymethyl | H | |
| 215 | CN | H | i-propoxymethyl | H | |
| 216 | Cl | H | i-propoxymethy | Me | |

The following table contains representative examples of the present invention. Each entry in each table is intended to be paired with the formula at the start of the table. For example, in Table 2, the compound is intended to be paired with one of 1a–11a, one of 1b–4b, one of 1c–4c, one of 1d–5d and one of 1–60e.

TABLE 2

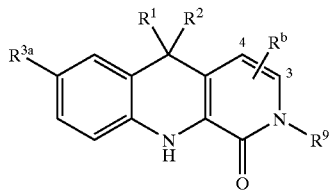

| # | |
|---|---|
| | R¹ |
| 1a | CF$_3$ |
| 2a | CHF$_2$ |
| 3a | CH$_3$ |
| 4a | cyclopropyl |
| 5a | CF$_2$CF$_3$ |
| 6a | methyl |
| 7a | ethyl |
| 8a | propyl |
| 9a | butyl |
| 10a | CN |
| 11a | hydroxymethyl |
| | R$^{3a}$ |
| 1b | H |
| 2b | chloro |
| 3b | fluoro |
| 4b | CH$_3$ |
| | R$^b$ |
| 1c | 3-chloro |
| 2c | 4-methyl |
| 3c | 4-chloro |
| 4c | H |
| | R$^9$ |
| 1d | H |
| 2d | methyl |
| 3d | ethyl |
| 4d | propyl |
| 5d | butyl |
| | R² |
| 1e | (6-methylpyrid-2-yl)methyl |
| 2e | Cyclopropylacetylenyl |
| 3e | n-Propyl |
| 4e | n-Butyl |
| 5e | 4-Fluorophenylmethyl |
| 6e | 2-Pyridylmethyl |
| 7e | i-Propyl |
| 8e | 3-Pyridylmethyl |
| 9e | 4-Pyridylmethyl |
| 10e | 3-Propynyl |
| 11e | 2-Pyridylethynyl |
| 12e | 2-(2-Pyridyl)ethyl |
| 13e | n-Propyl |
| 14e | 3-Propenyl |
| 15e | 2-Cyclopropylethyl |
| 16e | Ethynyl |
| 17e | 2-Ethoxyethyl |
| 18e | 2-chloroethyl |
| 19e | N-Cyclopropylaminomethyl |
| 20e | Hydroxymethyl |
| 21e | n-Propoxymethyl |
| 22e | i-Propoxymethyl |
| 23e | Methoxyethyl |
| 24e | diisopropoxymethyl |
| 25e | Propylaminomethyl |
| 26e | N-Methyl-i-propylaminomethyl |
| 27e | n-Propylaminomethyl |
| 28e | Cyclobutylaminomethyl |
| 29e | i-Butylaminomethyl |
| 30e | cyclopropylthiomethyl |
| 31e | i-propylsulfoxymethyl |
| 32e | t-butylsulfoxymethyl |

TABLE 2-continued

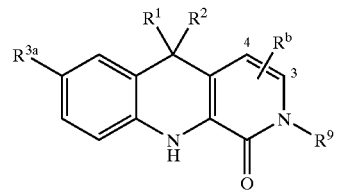

| # | |
|---|---|
| 33e | methylthiomethyl |
| 34e | ethylthiomethyl |
| 35e | i-propylthiomethyl |
| 36e | cyclopropylmethoxymethyl |
| 37e | cyclobutoxymethyl |
| 38e | cyanomethyl |
| 39e | 2-(ethylamino)ethyl |
| 40e | 2-(dimethylamino)ethyl |
| 41e | 2-(methylamino)ethyl |
| 42e | 2-(i-propylamino)ethyl |
| 43e | 2-(cyclopropylamino)ethyl |
| 44e | pentyl |
| 45e | vinyl |
| 46e | imidazolylethyl |
| 47e | pyrazolylethyl |
| 48e | 1,2,4-triazolylethyl |
| 49e | 2-(methylethylamino)ethyl |
| 50e | 2-(i-propylethylamino)ethyl |
| 51e | 2-(pyrrolidinyl)ethyl |
| 52e | 3-pentanylaminomethyl |
| 53e | dimethoxymethyl |
| 54e | i-butylaminomethyl |
| 55e | cyclopropylmethyl aminomethyl |
| 56e | allylaminomethyl |
| 57e | (R)-sec-butylaminomethyl |
| 58e | (S)-sec-butylaminomethyl |
| 59e | 1,3-dioxolanylmethyl |
| 60e | 1,3-dioxanylmethyl |

Utility

The compounds of this invention possess reverse transcriptase inhibitory activity and HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) that contains or is suspected to contain or be exposed to HIV.

The compounds provided by this invention are also useful as standard or reference compounds for use in tests or assays for determining the ability of an agent to inhibit viral replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "µg" denotes microgram, "mg" denotes milligram, "g" denotes gram, "µL" denotes microliter, "mL" denotes milliliter, "L" denotes liter, "mM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

Compounds tested in the assay described below are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM.

Using the methodology described below, a number of compounds of the present invention were found to exhibit a $K_i$ of $\leq 10$ µM, thereby confirming the utility of the compounds of the present invention as effective HIV reverse transcriptase inhibitors.

HIV RNA Assay
DNA Plasmids and in Vitro RNA Transcripts:

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, Tet. Lett. 1989, 30, 6287. The gag biotinylated capture probe (5-biotin-CTAGCTCCCTGCTTGCCCATACTA 3') (SEQ ID NO:1) was complementary to nucleotides 889–912 of HXB2 and the pol biotinylated capture probe (5'-biotin-CCCTATCATTTTTGGTTTCCAT 3') (SEQ ID NO:2) was complementary to nucleotides 2374–2395 of HXB2. Alkaline phosphatase conjugated oligonucleotides used as reporter probes were prepared by Syngene (San Diego, Calif.). The pol reporter probe (5' CTGTCT-TACTTTGATAAAACCTC 3') (SEQ ID NO:3) was complementary to nucleotides 2403–2425 of HXB2. The gag reporter probe (5' CCCAGTATTTGTCTACAGCCTTCT 3') (SEQ ID NO:4) was complementary to nucleotides 950–973 of HXB2. All nucleotide positions are those of the GenBank Genetic Sequence Data Bank as accessed through the Genetics Computer Group Sequence Analysis Software Package (Devereau Nucleic Acids Research 1984, 12, 387). The reporter probes were prepared as 0.5 µM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Strentavidin Coated Plates:

Streptavidin coated plates were obtained from DuPont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were $1-3 \times 10^7$ PFU (plaque forming units)/mL as measured by plaque assay on MT-2 cells (see below) Each aliquot of virus stock used for infection was thawed only once.

For evaluation of antiviral efficacy, cells to be infected were subcultured one day prior to infection. On the day of infection, cells were resuspended at $5 \times 10^5$ cells/mL in RPMI 1640, 5% FCS for bulk infections or at $2 \times 10^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20) A second hybridization of reporter probe to the immobilized complex of capture probe and hybridized target RNA was carried out in the washed streptavidin coated well by addition of 120 µl of a hybridization cocktail containing 4×SSC, 0.66% Tritonx 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer (2.5 M diethanolamine pH 8.9 (JBL Scientific), 10 MM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5 \times 10^5$ per mL ($1 \times 10^5$ per well). Cells were incubated with compounds for 30 minutes at 37° C. in a $CO_2$ incubator. For evaluation of antiviral potency, an appropriate dilution of HIV-1 (RF) virus stock (50 μL) was added to culture wells containing cells and dilutions of the test compounds. The final volume in each well was 200 μL. Eight wells per plate were left uninfected with 50 μL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2× concentrated compound solution to a single row of wells, were performed using a Perkin Elmer/Cetus ProPette.

Protein Binding and Mutant Resistance

In order to characterize NNRTI compounds for their clinical efficacy potential the effect of plasma proteins on antiviral potency and measurements of antiviral potency against wild type and mutant variants of HIV that carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 that carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A capsule formulation of the present invention can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A soft gelatin capsule formulation of the present invention can be prepared as follows. A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A tablet formulation of the present invention can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension formulation can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral formulation suitable for administration by injection can be prepared by stirring 1.5% by weight of active ingredient in 10% by volume propylene glycol and water. The solution is sterilized by commonly used techniques.

Combination Administration of Therapeutic Agents

The present invention provides a method for the treatment of HIV infection which comprises administering, in combination, to a host in need thereof a therapeutically effective amount of the following:

(a) a compound of formula (I); and (b) at least one compound selected from the group consisting of HIV reverse transcriptase inhibitors and HIV protease inhibitors, in one or more sterile containers.

Each therapeutic agent component of this combination method (i.e., component (a) and (b) set forth above) can independently be administered in any separate dosage form, such as those described above, and can be administered in various ways, as described above. In the following description component (b) is to be understood to represent one or more agents as described previously. Each individual therapeutic agent comprising component (b) may also be independently be administered in any separate dosage form, such as those described above, and can be administered in various ways, as described above.

Components (a) and any one or more of the agents comprising component (b) of the combination method of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes or dosage forms (for example, one component of the combination method may be administered orally, and another component may be administered intravenously).

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the combination method of this invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b) may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

As will be appreciated by one of skill in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

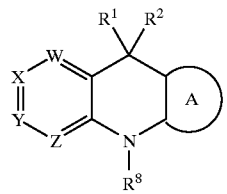

or a stereoisomeric form or mixture of stereoisomeric forms or a pharmaceutically acceptable salt form thereof, wherein:

A is a ring selected from:

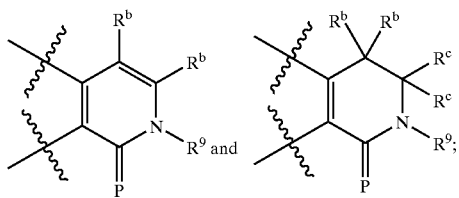

P is O or S;

$R^b$, at each occurrence, is independently selected from H, F, Cl, Br, I, CN, $C_{1-4}$ alkyl, $C_{1-4}$ alkenyl, $C_{1-4}$ alkynyl, $C_{1-4}$ alkyl-O—, or $C_{1-4}$ alkyl-NH—, $NH_2$;

$R^c$, at each occurrence, is independently selected from H, $C_{1-4}$ alkyl, $C_{1-4}$ alkenyl, and $C_{1-4}$ alkynyl;

W is $CR^3$;
X is $CR^{3a}$;
Y is $CR^{3b}$;
Z is $CR^{3c}$;

$R^1$ is selected from the group $C_{1-4}$ alkyl substituted with 0–9 halogen, cyclopropyl, hydroxymethyl, and CN;

$R^2$ is selected from the group $C_{1-6}$ alkyl substituted with 1–2 $R^4$, $C_{2-5}$ alkenyl substituted with 1–2 $R^4$, $C_{2-5}$ alkynyl substituted with 1 $R^4$, and a 6-membered heterocyclic system having 1 N atom substituted with 0–2 $R^{3d}$;

$R^3$ is selected from the group H, $C_{1-4}$ alkyl, —OH, $C_{1-4}$ alkoxy, $OCF_3$, $CF_3$, F, Cl, Br, I, —$(CH_2)_rNR^5R^{5a}$, —$NO_2$, —CN, —$C(O)R^6$, —$(CH_2)_rNHC(O)R^7$, —$(CH_2)_rNHC(O)NR^5R^{5a}$, —$NHSO_2R^{10}$, —S—$C_{1-4}$ alkyl, —$S(O)C_{1-4}$alkyl, —$S(O)_2C_{1-4}$alkyl, —$SO_2NR^5R^{5a}$, and a 5–6 membered heteroaromatic ring having 1–4 heteroatoms selected from the group O, N, and S;

$R^{3a}$ is selected from the group H, $C_{1-4}$ alkyl, —OH, $C_{1-4}$ alkoxy, $OCF_3$, $CF_3$, F, Cl, Br, I, —$(CH_2)_rNR^5R^{5a}$, —$NO_2$, —CN, —$C(O)R^6$, —$(CH_2)_rNHC(O)R^7$, —$(CH_2)_rNHC(O)NR^5R^{5a}$, —$NHSO_2R^{10}$, —S—$C_{1-4}$ alkyl, —$S(O)C_{1-4}$alkyl, —$S(O)_2C_{1-4}$alkyl, —$SO_2NR^5R^{5a}$, and a 5–6 membered heteroaromatic ring having 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, F, Cl, Br, I, C$_{1-4}$ alkyl, CN, —OH, —O—R$^{11}$, OCF$_3$, —O(CO)—R$^{13}$, —OS(O)$_2$C$_{1-4}$ alkyl, —NR$^{12}$R$^{12a}$, —C(O)R$^{13}$, —NHC(O)R$^{13}$, —SR$^{11}$, —S(O)R$^{11}$, —S(O)$_2$R$^{11}$, —NHSO$_2$R$^{10}$, and —SO$_2$NR$^{12}$R$^{12a}$;

R$^4$ is a 6-membered heterocyclic system having 1 N atom substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring having 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group H, C$_{1-3}$ alkyl and C$_{1-3}$ alkoxy;

R$^8$ is selected from the group H, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl)oxycarbonyl, (C$_{6-10}$ aryl)methylcarbonyl, (C$_{1-4}$ alkyl)carbonyloxy(C$_{1-4}$ alkoxy)carbonyl, C$_{6-10}$ arylcarbonyloxy(C$_{1-4}$ alkoxy)carbonyl, C$_{1-6}$ alkylaminocarbonyl, phenylaminocarbonyl, phenyl (C$_{1-4}$ alkoxy)carbonyl, and NR$^5$R$^{5a}$(C$_{1-6}$ alkyl)carbonyl;

R$^9$ is selected from H, C$_{1-4}$ alkyl, C$_{1-4}$ alkenyl, C$_{1-4}$ alkynyl, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl)oxycarbonyl, (C$_{6-10}$ aryl)methylcarbonyl, (C$_{1-4}$ alkyl)carbonyloxy(C$_{1-4}$ alkoxy)carbonyl, C$_{6-10}$ arylcarbonyloxy(C$_{1-4}$ alkoxy)carbonyl, C$_{1-6}$ alkylaminocarbonyl, phenylaminocarbonyl, phenyl (C$_{1-4}$ alkoxy)carbonyl, and NR$^5$R$^{5a}$(C$_{1-6}$ alkyl) carbonyl;

R$^{10}$ is selected from the group C$_{1-4}$ alkyl and phenyl;

R$^{11}$ is selected from C$_{1-6}$ alkyl, C$_{1-6}$ haloalkyl, C$_{1-6}$ alkyl substituted with C$_{3-6}$cycloalkyl substituted with 0–2 R$^{3e}$, C$_{2-6}$ alkenyl, C$_{2-6}$ alkynyl, C$_{3-6}$ carbocycle substituted with 0–2 R$^{3e}$;

R$^{12}$ and R$^{12a}$ are independently selected from H, C$_{1-6}$ alkyl, C$_{1-6}$ alkyl substituted with C$_{3-6}$cycloalkyl substituted with 0–2 R$^{3e}$, and C$_{3-6}$ carbocycle substituted with 0–2 R$^{3e}$;

alternatively, R$^{12}$ and R$^{12a}$ can join to form 4–7 membered heterocyclic ring;

R$^{13}$ is selected from the group H, C$_{1-6}$ alkyl, C$_{1-6}$ haloalkyl, C$_{1-6}$ alkoxy, C$_{2-6}$ alkenyl, C$_{2-6}$ alkynyl, —O—C$_{2-6}$ alkenyl, —O—C$_{2-6}$ alkynyl, NR$^{12}$R$^{12a}$, C$_{3-6}$carbocycle, and —O—C$_{3-6}$carbocycle; and t is selected from 0 and 1.

2. A compound of claim 1 or pharmaceutically acceptable salt forms thereof, wherein:

R$^2$ is selected from the group C$_{1-5}$ alkyl substituted with 1–2 R$^4$, C$_{2-5}$ alkenyl substituted with 1–2 R$^4$, C$_{2-5}$ alkynyl substituted with 1 R$^4$, and a 6-membered heterocyclic system having 1 N atom substituted with 0–2 R$^{3d}$, wherein the heterocyclic system is selected from 2-pyridyl, 3-pyridyl, and 4-pyridyl;

R$^3$ and R$^{3a}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring having 1–4 heteroatoms selected from the group O, N, and S;

alternatively, R$^3$ and R$^{3a}$ together form —OCH$_2$O—;

R$^{3b}$ and R$^{3c}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is a 6-membered heterocyclic system having 1 N atom substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, CH(CH$_3$)$_2$, OCH$_3$, OC$_2$H$_5$, and OCH(CH$_3$)$_2$.

3. A compound of claim 2, wherein:

P is O;

Ring A is:

R$^b$, at each occurrence, is selected from H, F, Cl, and Br, C$_{1-4}$ alkyl, CN, C$_{1-4}$ alkyl-NH—, NH$_2$;

R$^c$ is selected from H and methyl;

W is CR$^3$;

X is CR$^{3a}$;

Y is CR$^{3b}$;

Z is CR$^{3c}$;

R$^2$ is selected from the group C$_{1-3}$ alkyl substituted with 1–2 R$^4$, C$_{2-3}$ alkenyl substituted with 1–2 R$^4$; and C$_{2-3}$ alkynyl substitued with 1 R$^4$ R$^3$, R$^{3a}$, R$^{3b}$, and R$^{3c}$, at each occurrence, are independently selected from the group H, C$_{1-3}$ alkyl, OH, C$_{1-3}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^3$ and R$^{3a}$ together form —OCH$_2$O—;

R$^{3e}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;

R$^{3f}$, at each occurrence, is independently selected from the group H, F, Cl, Br, I, C$_{1-4}$ alkyl, CN, —OH, —O—R$^{11}$, —O(CO)—R$^{13}$, —SR$^{11}$, —S(O)R$^{11}$, —S(O)$_2$R$^{11}$, and —NR$^{12}$R$^{12a}$;

R$^4$ is and a 6-membered heterocyclic system having 1 N atom substituted with 0–1 R$^{3e}$, wherein the heterocyclic system is selected from 2-pyridyl, 3-pyridyl, and 4-pyridyl;

R$^5$ and R$^{5a}$ are independently selected from the group H, CH$_3$ and C$_2$H$_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H;

$R^9$ is H, methyl, ethyl, propyl, and i-propyl;

$R^{11}$ is selected from methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl; and $R^{12}$ and $R^{12a}$ are independently selected from H, methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

4. A compound of claim 3, or a pharmaceutically acceptable salt form thereof, wherein:

$R^2$ is selected from the group $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, $NR^5R^{5a}$, $NO_2$, —CN, $C(O)R^6$, NHC(O)$R^7$, and NHC(O)$NR^5R^{5a}$;

alternatively, $R^3$ and $R^{3a}$ together form —$OCH_2O$—;

$R^{3e}$, at each occurrence, is independently selected from the group $CH_3$, —OH, $OCH_3$, $OCF_3$, F, Cl, and —$NR^5R^{5a}$;

$R^{3f}$, at each occurrence, is independently selected from the group H, F, Cl, Br, I, $C_{1-4}$ alkyl, —OH, CN, —O—$R^{11}$, —O(CO)—$R^{13}$, and —$NR^{12}R^{12a}$, —$SR^{11}$, —$S(O)R^{11}$, —$S(O)_2R^{11}$, and —$OS(O)_2$methyl;

$R^4$ is a 6-membered heterocyclic system having 1 N atom substituted with 0–1 $R^{3e}$, wherein the heterocyclic system is selected from the group 2-pyridyl, 3-pyridyl, and 4-pyridyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and $R^9$ is selected from H and methyl.

5. A compound of claim 4, or a pharmaceutically acceptable salt form thereof, wherein:

$R^2$ is selected from the group methyl substituted with 1 $R^4$, ethyl substituted with 1 $R^4$, propyl substituted with 1 $R^4$, ethenyl substituted with 1 $R^4$, 1-propenyl substituted with 1 $R^4$, 2-propenyl substituted with 1 $R^4$, ethynyl substituted with 1 $R^4$, 1-propynyl substituted with 1 $R^4$, and 2-propynyl substituted with 1 $R^4$;

$R^{3e}$, at each occurrence, is independently selected from the group $CH_3$, —OH, $OCH_3$, $OCF_3$, F, Cl, and —$NR^5R^{5a}$;

$R^4$ is a 6-membered heterocyclic system having 1 N atom substituted with 0–1 $R^{3e}$, wherein the heterocyclic system is selected from the group 2-pyridyl, 3-pyridyl, and 4-pyridyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H.

6. A compound of claim 5, or a pharmaceutically acceptable salt form thereof, wherein:

$R^1$ is selected from methyl, ethyl, propyl, i-propyl, butyl, cyclopropyl, $CF_3$, $CF_2CH_3$, CN, and hydroxymethyl;

$R^2$ is selected from the group methyl substituted with 1 $R^4$, ethyl substituted with 1 $R^4$, propyl substituted with 1 $R^4$, ethenyl substituted with 1 $R^4$, 1-propenyl substituted with 1 $R^4$, 2-propenyl substituted with 1 $R^4$, ethynyl substituted with 1 $R^4$, 1-propynyl substituted with 1 $R^4$;

$R^3$, $R^{3b}$, and $R^{3c}$ are H;

$R^{3e}$ is $CH_3$;

$R^{3f}$, at each occurrence, is independently selected from the group H, F, Cl, Br, I, $C_{1-4}$ alkyl, CN, —OH, —O—$R^{11}$, —$SR^{11}$, —$S(O)R^{11}$, —$S(O)_2R^{11}$, and —$NR^{12}R^{12a}$;

$R^4$ is a 6-membered heterocyclic system having 1 N atom wherein the heterocyclic system is selected from the group 2-pyridyl, 3-pyridyl, and 4-pyridyl;

$R^{12}$ and $R^{12a}$ are independently selected from H, methyl, ethyl, propyl, and i-propyl, and $C_{3-6}$ carbocycle substituted with 0–2 $R^{3e}$ wherein the $C_{3-6}$ carbocycle is selected from cyclopropyl.

7. A compound of claim 6, or a pharmaceutically acceptable salt form thereof, wherein the compound is of formula (Ic):

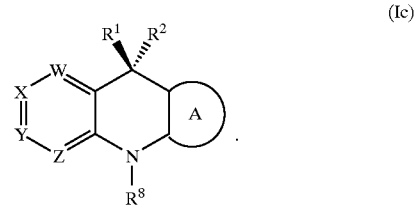

(Ic)

8. A compound of claim 1, or a pharmaceutically acceptable salt form thereof, wherein the compound of formula (I) is selected from:

7-fluoro-2-methyl-5-[(6-methyl-2-pyridinyl)methyl]-5-(trifluoromethyl)-5,10-dihydrobenzo[b]-1,7-naphthyridin-1(2H)-one;

7-fluoro-5-(2-pyridylmethyl)-5-(trifluoromethyl)-5,10-dihydrobenzo[b]-1,7-naphthyridin-1(2H)-one;

7-fluoro-5-(3-pyridylmethyl)-5-(trifluoromethyl)-5,10-dihydrobenzo[b]-1,7-naphthyridin-1(2H)-one;

7-fluoro-5-(4-pyridylmethyl)-5-(trifluoromethyl)-5,10-dihydrobenzo[b]-1,7-naphthyridin-1(2H)-one;

7-fluoro-5-(2-pyridylethynyl)-5-(trifluoromethyl)-5,10-dihydrobenzo[b]-1,7-naphthyridin-1(2H)-one;

7-fluoro-5-(2-(2-pyridyl)ethyl)-5-(trifluoromethyl)-5,10-dihydrobenzo[b]-1,7-naphthyridin-1(2H)-one;

7-Chloro-5-(2-pyridylmethyl)-5-trifluoromethyl-5,10-dihydrobenzo[b]-1,7-naphthyridin-1(2H)-one; and 7-Chloro-3-methyl-5-(2-pyridylmethyl)-5-trifluoromethyl-5,10-dihydrobenzo[b]-1,7-naphthyridin-1(2H)-one.

9. A pharmaceutical composition comprising a pharmaceutically acceptable carrier and a therapeutically effective amount of a compound according to claim 1 or pharmaceutically acceptable salt form thereof.

10. A method for treating HIV infection which comprises administering to a host in need of such treatment a therapeutically effective amount of a compound according to claim 1 or pharmaceutically acceptable salt form thereof.

11. A compound of formula (I):

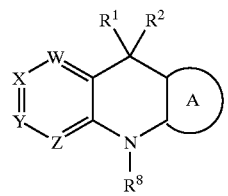

or a stereoisomeric form or mixture of stereoisomeric forms or a pharmaceutically acceptable salt form thereof, wherein:

A is a ring selected from:

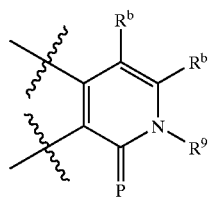

P is O or S;

$R^b$ is H, F, Cl, Br, I, $C_{1-4}$ alkyl, $C_{1-4}$ alkenyl, $C_{1-4}$ alkynyl, $C_{1-4}$ alkyl-O—, or $C_{1-4}$ alkyl-NH—;

W is $CR^3$;

X is $CR^{3a}$;

Y is $CR^{3b}$;

Z is $CR^{3c}$;

$R^1$ is selected from the group $C_{1-3}$ alkyl substituted with 0–7 halogen and cyclopropyl;

$R^2$ is —$R^{2c}$;

$R^{2c}$ is selected from the group $C_{1-6}$ alkyl substituted with 1–2 $R^4$, $C_{2-5}$ alkenyl substituted with 1–2 $R^4$, $C_{2-5}$ alkynyl substituted with 1 $R^4$, and a 6-membered heterocyclic system having 1 N atom substituted with 0–2 $R^{3d}$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$—$NHC(O)NR^5R^{5a}$, —$NHSO_2R^{10}$, —$SO_2NR^5R^{5a}$, and a 5–6 membered heteroaromatic ring having 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring having 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3f}$, at each occurrence, is independently selected from the group H, F, Cl, Br, I, $C_{1-4}$ alkyl, —OH, —O—$R^{11}$, —O—$C_{3-10}$ carbocycle substituted with 0–2 $R^{3e}$, $OCF_3$, —$O(CO)$—$R^{13}$, —$OS(O)_2C_{1-4}$alkyl, —$NR^{12}R^{12a}$, —$C(O)R^{13}$, —$NHC(O)R^{13}$, —$NHSO_2R^{10}$, and —$SO_2NR^{12}R^{12a}$;

$R^4$ is a 6-membered heterocyclic system having 1 N atom substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring having 0–1 O or N atoms;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, ($C_{1-6}$ alkyl)carbonyl, $C_{1-6}$ alkoxy, ($C_{1-4}$ alkoxy)carbonyl, $C_{6-10}$ aryloxy, ($C_{6-10}$ aryl)oxycarbonyl, ($C_{6-10}$ aryl)methylcarbonyl, ($C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl ($C_{1-4}$ alkoxy)carbonyl, and $NR^5R^{5a}$($C_{1-6}$ alkyl)carbonyl;

$R^9$ is selected from H, $C_{1-4}$ alkyl, $C_{1-4}$ alkenyl, and $C_{1-4}$ alkynyl;

$R^{10}$ is selected from the group $C_{1-4}$ alkyl and phenyl;

$R^{11}$ is selected from $C_{1-6}$ alkyl, $C_{1-6}$ haloalkyl, $C_{1-6}$ alkyl substituted with $C_{3-6}$cycloalkyl, $C_{2-6}$ alkenyl, $C_{2-6}$ alkynyl, $C_{3-6}$ carbocycle substituted with 0–2 $R^{3e}$;

$R^{12}$ and $R^{12a}$ are independently selected from H, $C_{1-6}$ alkyl, and $C_{3-6}$ carbocycle substituted with 0–2 $R^{3e}$;

alternatively, $R^{12}$ and $R^{12a}$ can join to form 4–7 membered ring; and $R^{13}$ is selected from the group H, $C_{1-6}$ alkyl, $C_{1-6}$ haloalkyl, $C_{1-6}$ alkoxy, $C_{2-6}$ alkenyl, $C_{2-6}$ alkynyl, —O—$C_{2-6}$ alkenyl, —O—$C_{2-6}$ alkynyl, $NR^{12}R^{12a}$, $C_{3-6}$carbocycle, and —O—$C_{3-6}$carbocycle.

12. A compound of formula (I):

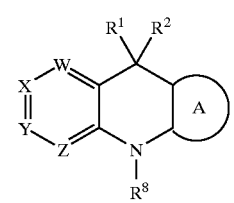

or a stereoisomeric form or mixture of stereoisomeric forms or a pharmaceutically acceptable salt form thereof, wherein:

A is a ring selected from:

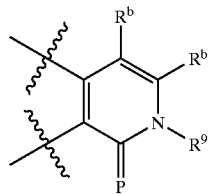

P is O or S;

$R^b$ is H, F, Cl, Br, I, $C_{1-4}$ alkyl, $C_{1-4}$ alkenyl, $C_{1-4}$ alkynyl, $C_{1-4}$ alkyl-O—, or $C_{1-4}$ alkyl-NH—;

W is $CR^3$;

X is $CR^{3a}$;

Y is $CR^{3b}$;

Z is $CR^{3c}$;

$R^1$ is selected from the group $C_{1-3}$ alkyl substituted with 0–7 halogen and cyclopropyl;

$R^2$ is —$R^{2c}$;

$R^{2c}$ is selected from the group $C_{1-6}$ alkyl substituted with 1–2 $R^4$, $C_{2-5}$ alkenyl substituted with 1–2 $R^4$, $C_{2-5}$ alkynyl substituted with 1 $R^4$, and a 6-membered heterocyclic system having 1 N atom substituted with 0–2 $R^{3d}$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring having 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring having 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, $NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^4$ is a 6-membered heterocyclic system having 1 N atom substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring having 0–1 O or N atoms;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, ($C_{1-6}$ alkyl)carbonyl, $C_{1-6}$ alkoxy, ($C_{1-4}$ alkoxy)carbonyl, $C_{6-10}$ aryloxy, ($C_{6-10}$ aryl)oxycarbonyl, ($C_{6-10}$ aryl)methylcarbonyl, ($C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl ($C_{1-4}$ alkoxy)carbonyl, and $NR^5R^{5a}$($C_{1-6}$ alkyl)carbonyl;

$R^9$ is selected from H, $C_{1-4}$ alkyl, $C_{1-4}$ alkenyl, and $C_{1-4}$ alkynyl; and $R^{10}$ is selected from the group $C_{1-4}$ alkyl and phenyl.

* * * * *